(12) United States Patent
Cucin

(10) Patent No.: US 8,574,223 B2
(45) Date of Patent: Nov. 5, 2013

(54) METHOD OF COLLECTING AND IN SITU PROCESSING OF ASPIRATED FAT TISSUE SAMPLED FROM A HUMAN PATIENT DURING TISSUE ASPIRATION OPERATIONS

(75) Inventor: Robert L. Cucin, West Palm Beach, FL (US)

(73) Assignee: Rocin Laboratories, Inc., West Palm Beach, FL (US)

( * ) Notice: Subject to any disclaimer, the term of this patent is extended or adjusted under 35 U.S.C. 154(b) by 0 days.

(21) Appl. No.: 13/315,228

(22) Filed: Dec. 8, 2011

(65) Prior Publication Data

US 2012/0277624 A1 Nov. 1, 2012

Related U.S. Application Data

(63) Continuation of application No. 12/850,786, filed on Aug. 5, 2010, which is a continuation-in-part of application No. 12/462,596, filed on Aug. 5, 2009, and a continuation-in-part of application No. 12/813,067, filed on Jun. 10, 2010.

(51) Int. Cl.
*A61M 1/00* (2006.01)

(52) U.S. Cl.
USPC .......................................................... 604/542

(58) Field of Classification Search
USPC ...................... 604/319, 540–544; 606/32, 40; 600/109, 110, 204, 425
See application file for complete search history.

(56) References Cited

U.S. PATENT DOCUMENTS

| | | | |
|---|---|---|---|
| 2,768,754 A | 10/1956 | Briggs | |
| 2,895,162 A | 7/1959 | Harris | |
| 3,938,505 A | 2/1976 | Jamshidi | |
| 4,083,706 A | 4/1978 | Wiley | |

(Continued)

FOREIGN PATENT DOCUMENTS

WO 2011017517 A 2/2011

OTHER PUBLICATIONS

Effect of potentially modifiable risk factors associated with myocardial infarction in 52 countries (the INERHEART study): case-control study. Salim Yusuf, Steven Hawken, Stephanie Ounpuu, Tony Dans, Ahivaro Avezum, Fernando Lanas, Matthew McQueen, Andrzej Budaj, Prem Pais, John Varigos, Liu Lisheng on behalf of the INTERHEART Study Investigators. Lancet 2004; vol. 364; 937-52. Published Online Sep. 3, 2004, Http://Image;thelancet.com/extras/04art8001web.Pdf. 16 pages.

(Continued)

*Primary Examiner* — Melanie Hand
(74) *Attorney, Agent, or Firm* — Thomas J. Perkowski, Esq., PC

(57) ABSTRACT

A method of collecting and in situ processing of aspirated fat tissue sampled from a human patient. The method involves providing a surgeon with a powered-assisted hand-held fat tissue aspiration instrument having a cannula, and a fat tissue sampling, processing and collection device installed between the power-assisted fat aspiration instrument and a vacuum source. The fat tissue sampling, collection and processing device includes a suction plate, mounted within a collection chamber, and having multiple hollow projections for supporting the open proximal ends of a plurality of tissue collection and processing tubes, wherein each tissue collection and processing tube has micro-pores formed in the side walls thereof, and its distal end opening is capped. Aspirated fat tissue is collected in a selected tissue collection and processing tube, while allowing fluid to flow and filter through the micro-pores as aspirated fat tissue flows through the cannula of the fat aspiration instrument.

11 Claims, 62 Drawing Sheets

(56) References Cited

U.S. PATENT DOCUMENTS

| | | |
|---|---|---|
| 4,568,332 A | 2/1986 | Shippert |
| 4,651,753 A | 3/1987 | Lifton |
| 4,710,162 A | 12/1987 | Johnson |
| 4,714,595 A | 12/1987 | Anthony et al. |
| 4,744,789 A | 5/1988 | Johnson |
| 4,792,327 A | 12/1988 | Swartz |
| 4,834,703 A | 5/1989 | Dubrul et al. |
| 4,886,492 A | 12/1989 | Brooke |
| 5,013,300 A | 5/1991 | Williams |
| 5,027,827 A | 7/1991 | Cody et al. |
| 5,052,999 A | 10/1991 | Klein |
| 5,095,901 A | 3/1992 | Davitashvili et al. |
| 5,102,410 A | 4/1992 | Dressel |
| 5,106,364 A | 4/1992 | Hayafuji et al. |
| 5,112,302 A | 5/1992 | Cucin |
| 5,171,660 A | 12/1992 | Carpenter et al. |
| 5,304,207 A | 4/1994 | Stromer |
| 5,348,022 A | 9/1994 | Leigh et al. |
| 5,348,535 A | 9/1994 | Cucin |
| 5,358,638 A | 10/1994 | Gershenson |
| 5,372,945 A | 12/1994 | Alchas et al. |
| 5,520,685 A | 5/1996 | Wojciechowicz |
| 5,643,198 A | 7/1997 | Cucin |
| 5,697,383 A | 12/1997 | Manders et al. |
| 5,792,603 A | 8/1998 | Dunkelman et al. |
| 5,865,803 A | 2/1999 | Major |
| 5,911,699 A | 6/1999 | Anis et al. |
| 5,944,748 A | 8/1999 | Mager et al. |
| 5,980,469 A | 11/1999 | Burbank et al. |
| 6,033,375 A | 3/2000 | Brumbach |
| 6,121,042 A | 9/2000 | Peterson et al. |
| 6,139,518 A | 10/2000 | Mozsary et al. |
| 6,152,142 A | 11/2000 | Tseng |
| 6,162,187 A | 12/2000 | Buzzard et al. |
| 6,190,364 B1 | 2/2001 | Imbert |
| 6,203,518 B1 | 3/2001 | Anis et al. |
| 6,204,375 B1 | 3/2001 | Lader |
| 6,213,971 B1 | 4/2001 | Poole |
| 6,270,471 B1 | 8/2001 | Hechel et al. |
| 6,316,247 B1 | 11/2001 | Katz et al. |
| 6,346,107 B1 | 2/2002 | Cucin |
| 6,394,973 B1 | 5/2002 | Cucin |
| 6,450,941 B1 | 9/2002 | Larsen |
| 6,468,225 B1 | 10/2002 | Lundgren |
| 6,471,069 B2 | 10/2002 | Lin et al. |
| 6,471,716 B1 | 10/2002 | Pecukonis |
| 6,478,681 B1 | 11/2002 | Overaker et al. |
| 6,494,876 B1 | 12/2002 | Fowler et al. |
| 6,520,935 B1 | 2/2003 | Jansen et al. |
| 6,544,211 B1 | 4/2003 | Andrew et al. |
| 6,544,246 B1 | 4/2003 | Niedospial, Jr. |
| 6,554,803 B1 | 4/2003 | Ashman |
| 6,632,182 B1 | 10/2003 | Treat |
| 6,638,235 B2 | 10/2003 | Miller et al. |
| 6,638,238 B1 | 10/2003 | Weber et al. |
| 6,652,522 B2 | 11/2003 | Cucin |
| 6,663,659 B2 | 12/2003 | McDaniel |
| 6,676,629 B2 | 1/2004 | Andrew et al. |
| 6,761,701 B2 | 7/2004 | Cucin |
| 6,786,405 B2 | 9/2004 | Wiedenhoefer |
| 6,795,728 B2 | 9/2004 | Chornenky et al. |
| 6,835,202 B2 | 12/2004 | Harth et al. |
| 6,872,199 B2 | 3/2005 | Cucin |
| 6,875,207 B2 | 4/2005 | Weber et al. |
| 6,899,723 B2 | 5/2005 | Chen |
| 6,951,611 B2 | 10/2005 | Dannenmaier et al. |
| 6,992,233 B2 | 1/2006 | Drake et al. |
| 7,018,395 B2 | 3/2006 | Chen |
| 7,041,217 B1 | 5/2006 | Close et al. |
| 7,081,128 B2 | 7/2006 | Hart et al. |
| 7,166,576 B2 | 1/2007 | Cicardi et al. |
| 7,175,081 B2 | 2/2007 | Andreasson et al. |
| 7,181,271 B2 | 2/2007 | Berg et al. |
| 7,241,616 B2 | 7/2007 | Ohno et al. |
| 7,258,674 B2 | 8/2007 | Cribbs et al. |
| 7,295,872 B2 | 11/2007 | Kelly et al. |
| 7,306,740 B2 | 12/2007 | Freund |
| 7,311,722 B2 | 12/2007 | Larsen |
| 7,381,206 B2 | 6/2008 | Cucin |
| 7,384,417 B2 | 6/2008 | Cucin |
| 7,390,484 B2 | 6/2008 | Fraser et al. |
| 7,473,420 B2 | 1/2009 | Fraser et al. |
| 7,488,427 B2 | 2/2009 | Freund |
| 7,501,115 B2 | 3/2009 | Fraser et al. |
| 7,514,075 B2 | 4/2009 | Hedrick et al. |
| 7,595,043 B2 | 9/2009 | Hedrick et al. |
| 7,639,136 B1 | 12/2009 | Wass et al. |
| 7,651,684 B2 | 1/2010 | Hedrick et al. |
| 7,687,059 B2 | 3/2010 | Fraser et al. |
| 7,712,674 B1 | 5/2010 | Warner et al. |
| 7,718,617 B2 | 5/2010 | Cicardi et al. |
| 7,740,605 B2 | 6/2010 | Cucin |
| 7,767,208 B2 | 8/2010 | Chen |
| 7,771,716 B2 | 8/2010 | Hedrick et al. |
| 7,780,649 B2 | 8/2010 | Shippert |
| 7,789,872 B2 | 9/2010 | Shippert |
| 7,794,449 B2 | 9/2010 | Shippert |
| 7,824,848 B2 | 11/2010 | Owen et al. |
| 7,887,795 B2 | 2/2011 | Fraser et al. |
| 7,901,672 B2 | 3/2011 | Fraser et al. |
| 7,951,590 B2 | 5/2011 | Gen |
| 7,988,633 B2 | 8/2011 | Hossack et al. |
| 7,990,272 B2 | 8/2011 | Wass et al. |
| 8,062,286 B2 | 11/2011 | Shippert |
| 8,099,297 B2 | 1/2012 | Brevnova et al. |
| 8,105,580 B2 | 1/2012 | Fraser et al. |
| 8,113,424 B2 | 2/2012 | Philippe |
| 8,119,121 B2 | 2/2012 | Fraser et al. |
| 8,133,389 B2 | 3/2012 | Dorian et al. |
| 8,152,821 B2 | 4/2012 | Gambale et al. |
| 8,182,450 B2 | 5/2012 | Moosheimer et al. |
| 8,268,612 B2 | 9/2012 | Owen et al. |
| 2001/0014785 A1 | 8/2001 | Sussman et al. |
| 2001/0031976 A1 | 10/2001 | Lobdell |
| 2002/0128632 A1 | 9/2002 | Cucin |
| 2002/0138047 A1 | 9/2002 | Lopez |
| 2002/0151874 A1 | 10/2002 | Kolster et al. |
| 2002/0173814 A1 | 11/2002 | Jung et al. |
| 2003/0078609 A1 | 4/2003 | Finlay et al. |
| 2003/0088235 A1 | 5/2003 | Tazi |
| 2003/0105454 A1 | 6/2003 | Cucin |
| 2003/0125639 A1 | 7/2003 | Fisher et al. |
| 2003/0144606 A1 | 7/2003 | Kadziauskas et al. |
| 2003/0187383 A1 | 10/2003 | Weber et al. |
| 2004/0073195 A1 | 4/2004 | Cucin |
| 2004/0222137 A1 | 11/2004 | Hashimoto |
| 2004/0267562 A1 | 12/2004 | Fuhrer et al. |
| 2005/0004632 A1 | 1/2005 | Benedict |
| 2005/0049521 A1 | 3/2005 | Miller et al. |
| 2005/0054995 A1 | 3/2005 | Barzell et al. |
| 2005/0075703 A1 | 4/2005 | Larsen |
| 2005/0197648 A1 | 9/2005 | Cucin |
| 2005/0233298 A1 | 10/2005 | Farsedakis |
| 2005/0256445 A1 | 11/2005 | Cucin |
| 2005/0266494 A1 | 12/2005 | Hodge |
| 2005/0267446 A1 | 12/2005 | Cucin |
| 2006/0093527 A1 | 5/2006 | Buss |
| 2007/0239176 A1 | 10/2007 | Stokes et al. |
| 2008/0033758 A1 | 2/2008 | Keeley |
| 2008/0154240 A1 | 6/2008 | Shippert |
| 2008/0154292 A1 | 6/2008 | Huculak et al. |
| 2009/0076486 A1 | 3/2009 | Cucin |
| 2009/0093790 A1 | 4/2009 | Massengale |
| 2009/0192498 A1 | 7/2009 | Andrew et al. |
| 2009/0192854 A1 | 7/2009 | Pietrucha, Jr. et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2011/0034905 A1 | 2/2011 | Cucin |
| 2011/0118542 A1 | 5/2011 | Cucin |
| 2011/0213336 A1 | 9/2011 | Cucin |
| 2012/0101479 A1 | 4/2012 | Paspaliaris et al. |

OTHER PUBLICATIONS

(56) References Cited

OTHER PUBLICATIONS

Adipokines: the missing link between insulin resistance and obesity by Antuna-Puente B., Feve B., Fellahi S., Bastard J.P.; Inserm U680, faculte de medecine Saint-Antoine, university Pierre-et Marie Curie, Paris 6, 75012, Paris, France; Diabetes Metab, Feb. 2008, 34(1):2-11. 10 page.
Adipose expression of tumor necrosis factor-alpha: direct role in obesity-linked insulin resistance (Abstract). Hotamisligil GS, Shargill N.S, Spiegelman BM; Dana-Farber Cancer Institute, Boston MA; Science Jan. 1, 1993; 259(509) 87-91. 1 page.
Adipose Tissue as an Endocrine Organ, by Erin E. Kershaw and Jeffrey S. Flier; Division of Endocrinology, Dept. of Medicine Beth israel Deaconess Medical Center, Boston MA 02215; Journal of Clinical Endocrinology & Metabolism 89(6): pp. 2548-2556, Copyright 2004 by the Endocrine Society, 9 pages.
Amelioration of diet-induced diabetes mellitus by removal of visceral fat by Cid Pitombo, Eliana P. Araujo, Claudio T. De Souza, Jose C. Pareja, Bruno Geloneze and Licio A. Velloso. Journal of Endocrinology (2006) 191, 699-706, Society for Endocrinology, printed in Great Britain, 8 pages.
Diabetes: insulin resistance and derangements in lipid metabolism. Cure through intercention in fat transport and storage. Raz I., Eldor R., Cemea S., Shafrir E.; Dept. of Medicine, Diabetes Ctr., Hadassah University Hospital, Jerusalem 91120, Israel, ntv502@netcision.net. il. Diabetes Metab Res Rev. Jan.-Feb. 2005; 21(1) 3-14. 12 pages.
Effect of multidisciplinary program of weight reduction on andothelial functions in obese women (Abstract). Nocoletti G., Giugliano G., Pontillo A. Cioffi M., D'Andea F., Giuglianoo D., Esposito K., Chair of Plastic and Reconstructive Surgery, Second University of Naples, Naples Italy. J. Endocrinol Invest Mar. 2003; 26(3): RC5-88. 1 page.
Effect of Liposuction on insulin resistance and vascular inflammatory markers in obese women by G. Giugliano, G. Nicolletti, E. Grelia, F. Giugliano, K. Esposito, N. Scuderi, F. D'Andrea; British Journal of Plastic Surgery, of. vol. 57, Issue 3, pp. 190-194, Apr. 2004, 5 pagess.
Guidelines on Laparoscopy, European Association of Urology, J.D. Doublet, G. Janetshek, A. Joyce, A. Mandressi, J. Rasswerller, D. Tolley, 2002, 38 pages.
Historical perspective: visceral obesity and related comorbidity in Joannes Bapista Morgagni's 'De sedibus et causis morborum per anatomen indagata' by Enzi G. Busetto L., Inelmen EM, Coin A., Sergi G.; Dept. of Medical and Surgical Sciences, Univ. of Padova, Italy, Int J Obes Relat Metab Disord. Apr. 2003; 534-5. 2 pages.
Human mesenteric adipose tissue plays unique role versus subcutaneous and omental fat in obesity related diabetes (Abstract). Yang YK, Chen M, Clements RH, Abrams GA, Aprahamian CJ, Harmon CM; Dept. of Surgery, Univ. of Alabama at Birmingham, USA, Cell Physiol Biochem. 2008;22(5-6): 531-8. Epub Dec. 9, 2008. 1 page.
Improvements in cardiovascular risk profile ater large-volume lipoplasty: a 1-year follow-up study by Giese SY, Neborsky R, Bulan EJ, Spear SL, Yankvski, JA; Aesthet Surg J Nov. 21, 2001(6): 527-31. 5 pages.
International Search Report in International Application No. PCT/US 11/62346 dated Jul. 2, 2012.
International Search Report, International Application No. PCT/US 10/44543, Jan. 6, 2011.
Large-Volume Liposuction and Extensive Abdominoplasty: a feasible alternative for improving bod shape by Carenas-Camarena, Lazaro M.D.; Gonzalez, Luis M.D.; Plastic & Reconstructive Surgery: Oct. 1998—vol. 102—Issue 5—pp. 168-1707. 9 pages.
Leptin and the Regulation of Body Weight by Jeffrey M. Friedman, Rockefekker University, new York NY 10065 USA fried@mail.rockefeller.edu; Copyright 2011 by the Keo Journal of Medicine. 9 pages.
Mechanism of the Postreceptor Defect in Insulin Action in Human Obesity: Decrease in Glucose Transport System Activity; Theodore P. Ciaraldi, Orville G. Kolterman, and Jerrold M. Olefsky, Dept. of Medicine, University of Colorado Health Sciences Ctr., Div. of Ensocrinology/Metabolism, Denver CO 80262; J. Clin. Invest. The American Soc. Or Clinical Investigation, Inc., 0021-9738/81/10/0875/06, vol. 68, Oct. 1981, pp. 875-880. 6 pages.
Mediastinal Fat, Insulin Resistance, and Hypertension by Arya M. Shara; Hypertension 2004, 44:117-118: originally published online Jul. 12, 2004 doi: 10.1161/01.HYP.0000137993.7045.82: Copyright 2004 American Heart Assn., ISN: 0194-911X. Online SSSN: 1524-4563. http://hyper.ahajournals.org/content/44/2/117. 3 pages.
Modification of Insulin, glucose and cholesterol levels in nonobese women undergoing liposuction, is liposuction metabolically safe? Robles-Cervantes JA, Yanez-Diaz S., Cardenas-Camarena L.; Ann Plast Surg. Jan. 2004 ; 52(1): 64-7. 4 pages.
Novel Interactions of Adiponectin with the Endocrine System and Inflammatory Parameters by Jose Manuel Fernandez-Real, Abel Lopez-Bermejo, Roser Casamitjana and Wifredo Ricart; Unit of Diabetes, Endocrinology and Nutrition, Dept. of Internal Medicine, University Hospital of Girona "Dr. Josep Trueta," 17007 Girona, Spain; The Journal of Clinical Endocrinology & Metabolism 88(6): 2714-2718; Copyright 2003 by The Endocrine Society doi: 10.1210/jc.2002-021583. 5 pages.
Obesity and the Risk of Cardiovascular Disease, Mitchell N. Rashid, MD; Francisco Fuetes, MD; Robert C. Tonchon; MD, Paulette S. Wehner MD; Dept. Of Internal Medicine, Marshall University School of Medicine, Huntington WV; University of Texas, and the Dept. of Cardiovascular Medicine, Marshall University, Huntington WV. Preventive Cardiology Winter 2003. 6 pages.
Obesity in the new millennium (Abstract). Friedman JM. The Rockefeller University, New York NY 10021-6399 USA; Nature Apr. 6, 2000, 404 (6778)632-4. 1 page.
Omentectomy and Metabolic Syndrome. ClinicalTrialsFeeds.org, U.S. National Institutess of Health Clinical Trials Search Delivered via RSS. Last Updated: Nov. 24, 2009, Verified by Instituto Nacional de Ciencias Medicas y Nutricion Salvador Zubrian, No. 2009. 10 pages.
Surgical removal of visceral adipose tissue: effects on insulin action. Gabriely I, Barzaila N.; Institute for Aging Research, Belfer Bldg. #701, Albert Einstein College of Medicine, 1300 Morris Park Avenue, Bronx NY 10461 USA. 6 pages.
The effects of surgically removing subcutaneous fat on the metabolic profile and insulin sensitivity in obese women after large-volume liposuction treatment (Abstract). Gonzalez-Ortiz M., Robles-Cervantes JA, Cardenas-Camarena L., Bustos-Saldana R., Martinez-Abundis E.; Medial Research Unit in Clinical Epidemiology, West National Medical Center, Mexican Institute of Social Security, Guadalajara, Mexico. uiec@prodigy.net.mx. Horn Metab Res. Aug. 2002; 34(8): 446-9. 1 page.
The role of TNF-alpha in insulin resistance. Borst SE. Dept. of Excercise & Sport Sciences, University of Florida, Malcolm Randall VA Medical Center, Gainesville FL 32608-1197, USA seborst@ufi.edu; Endocrine Mar.-Apr. 2004; 23(2-3) 177-82. 6 pages.

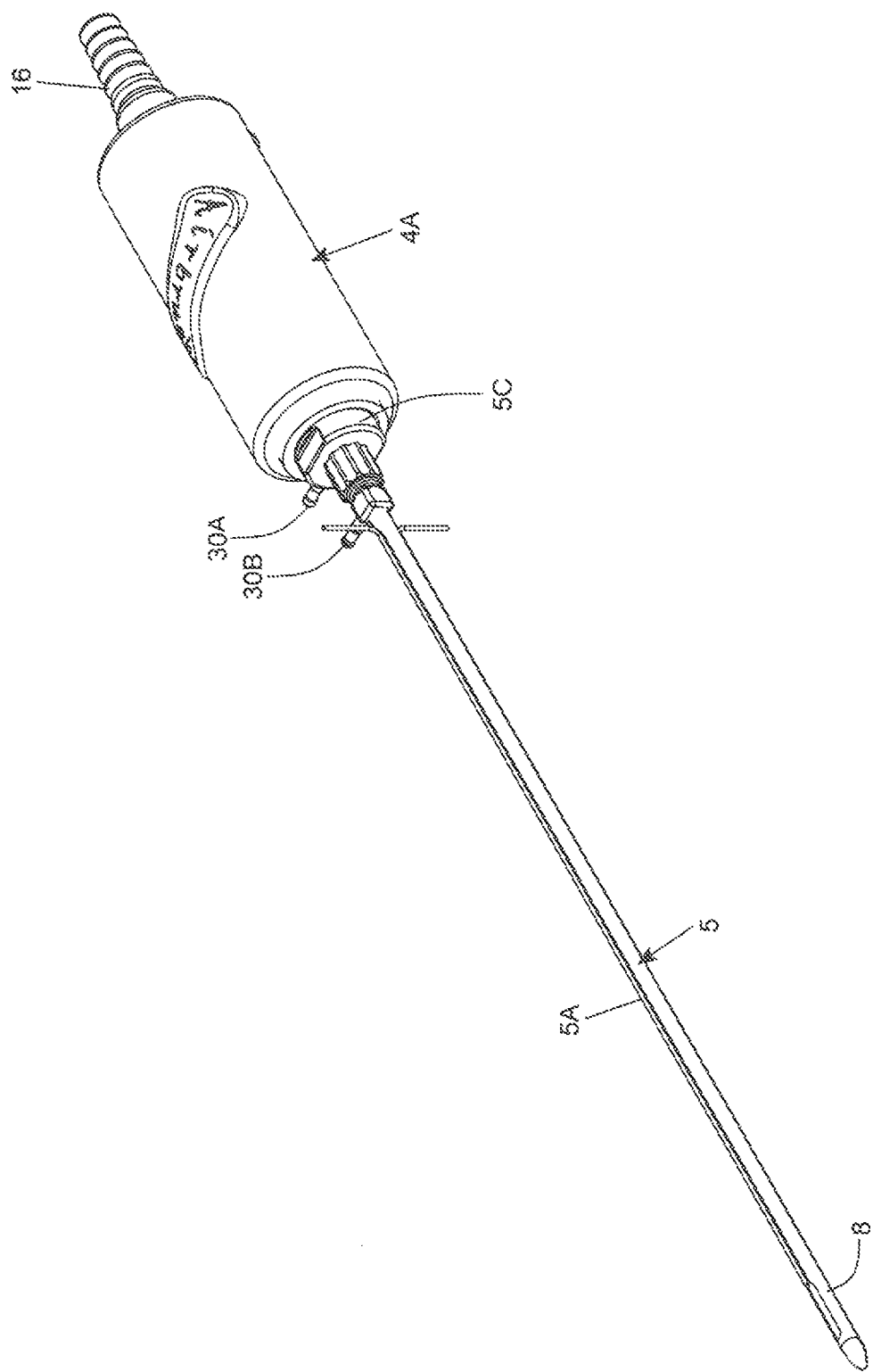
FIG. 2A1

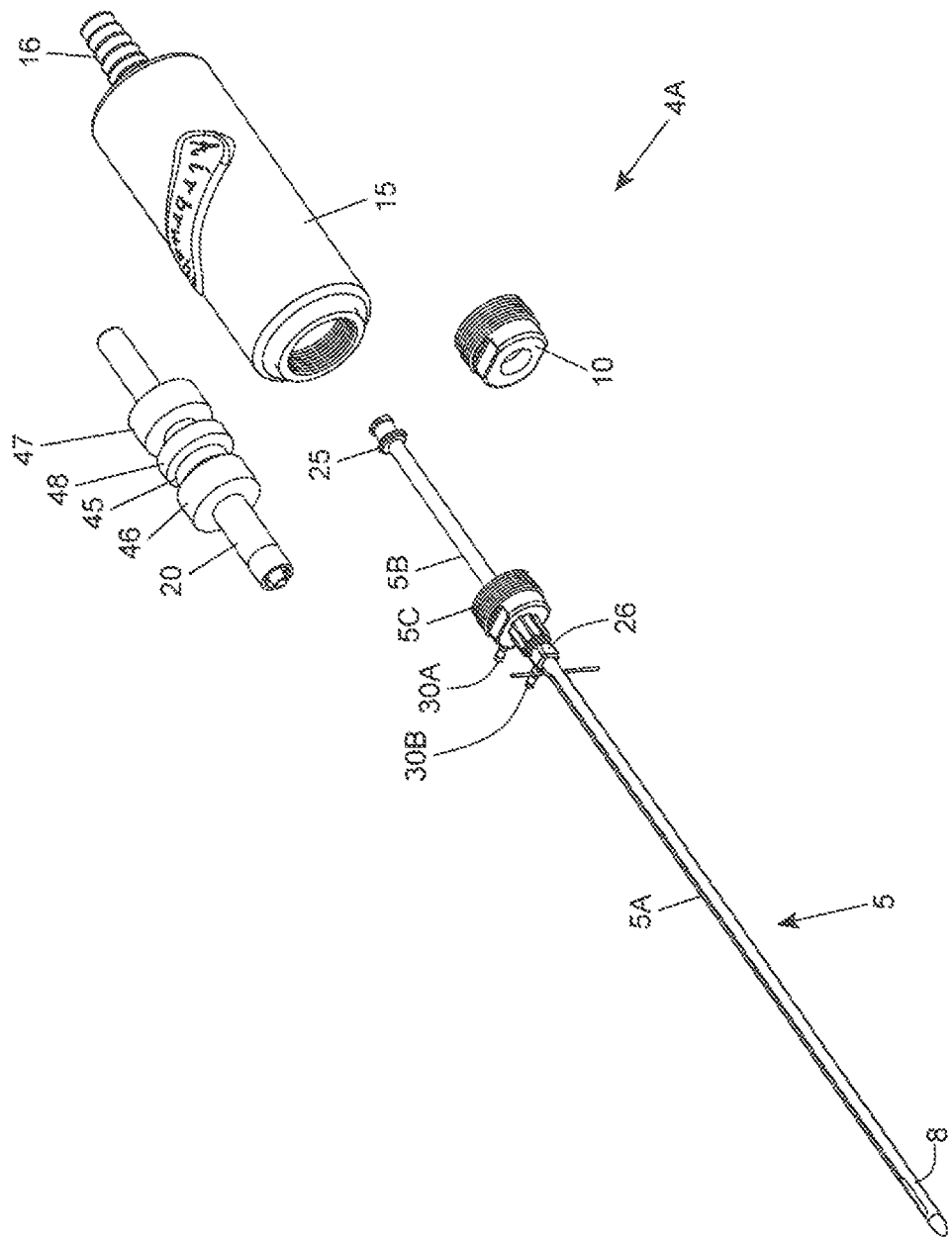
FIG. 2A2

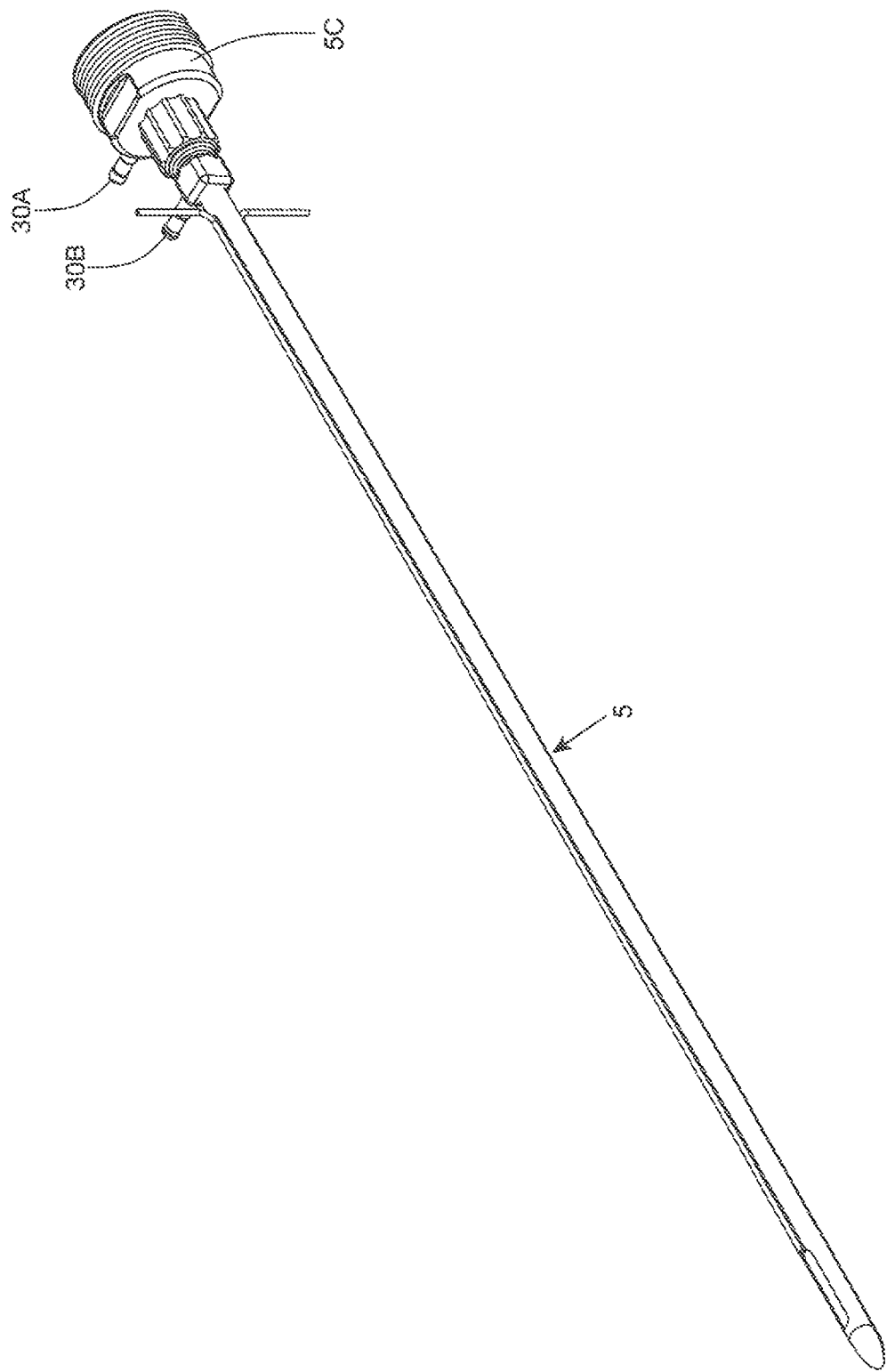

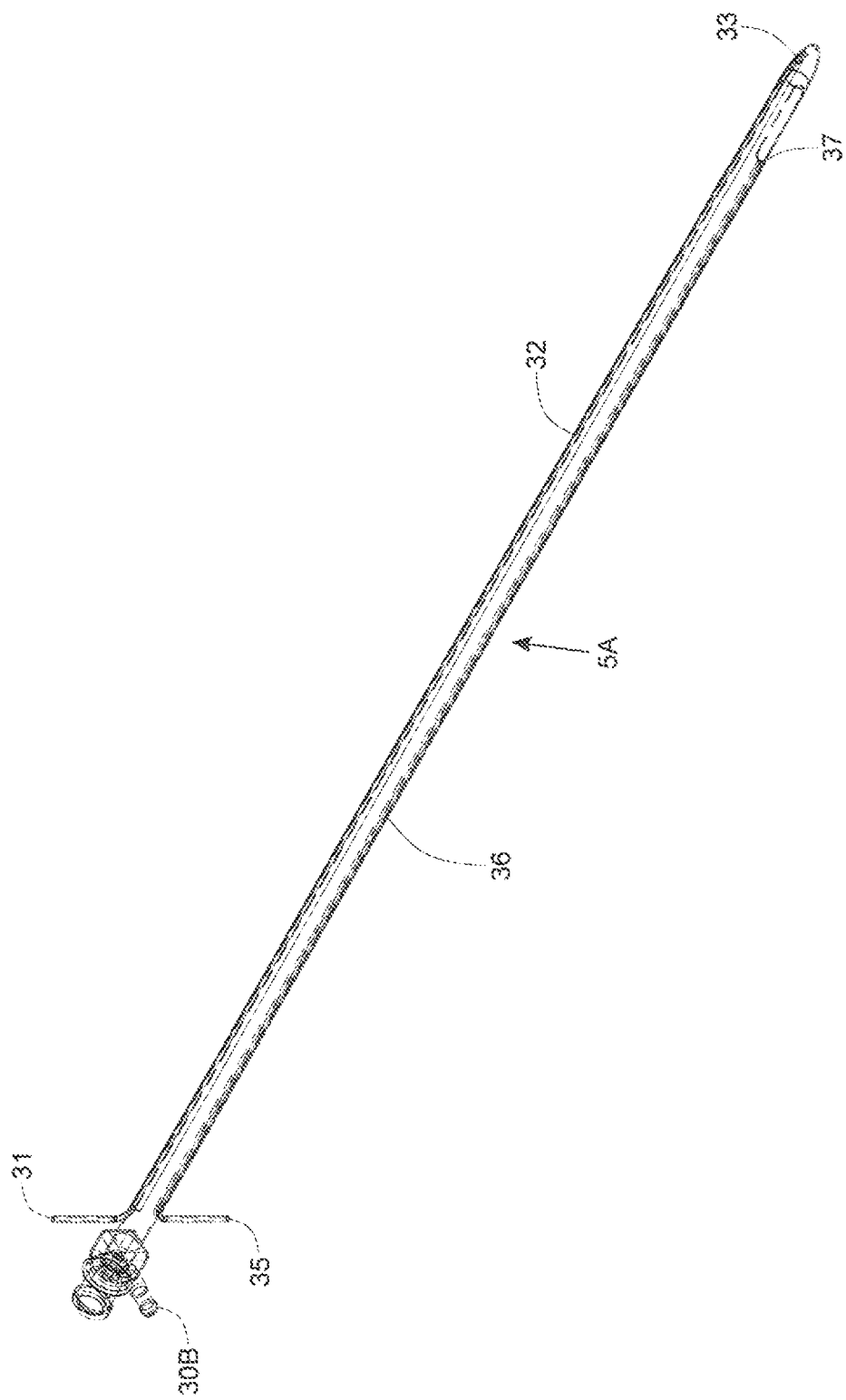
FIG. 2D1

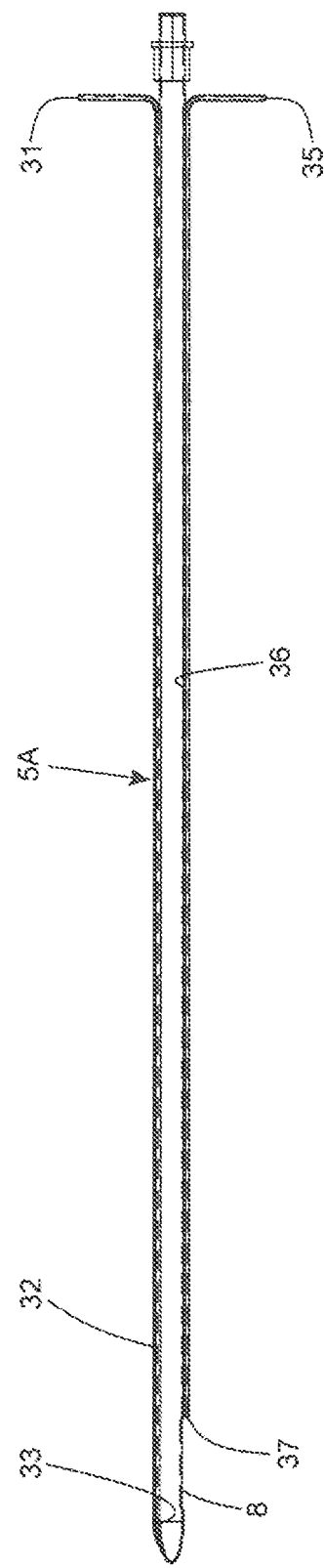
FIG. 2D2

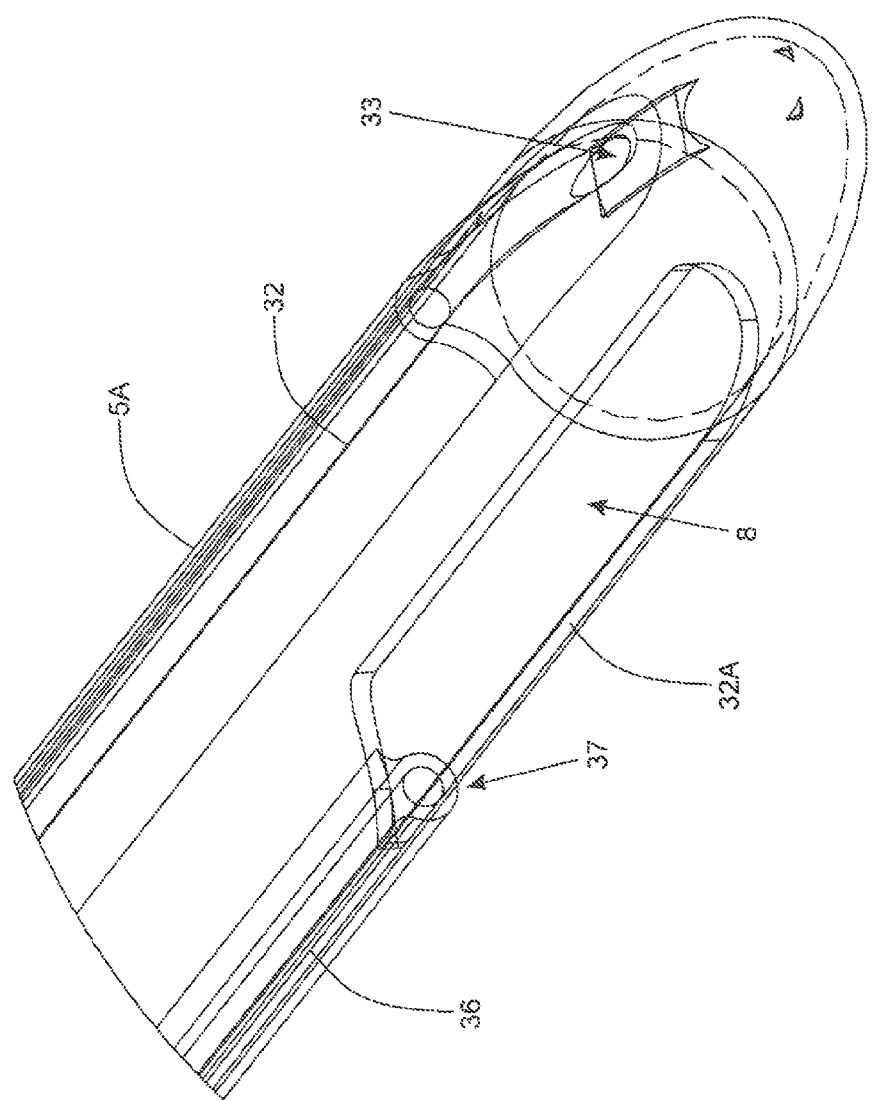
FIG. 2D3

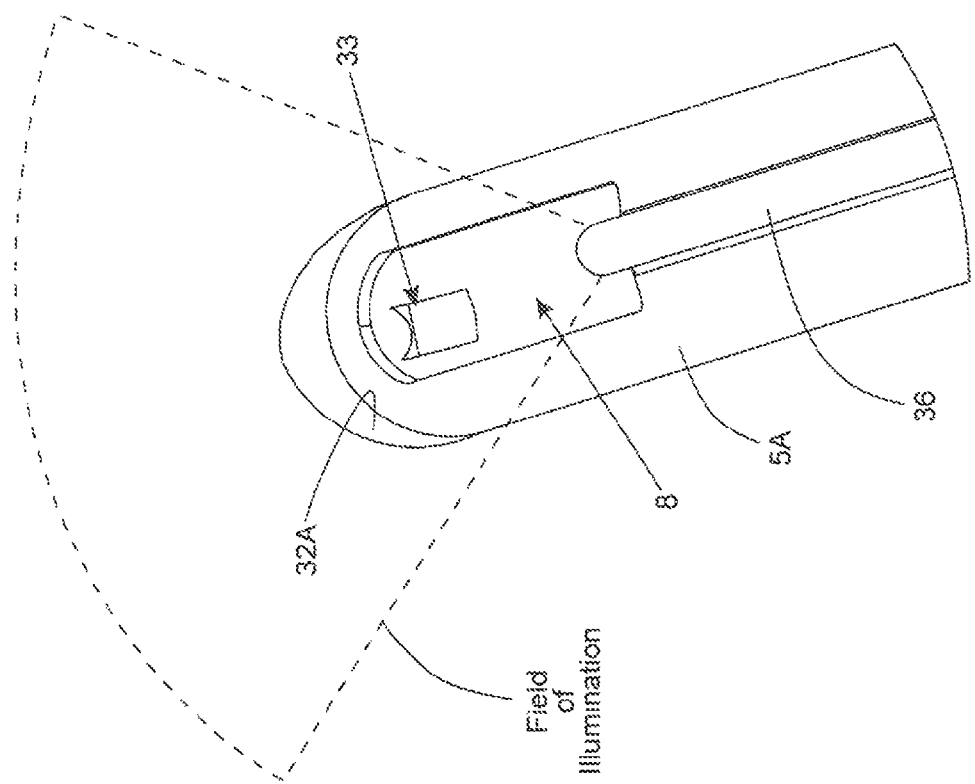

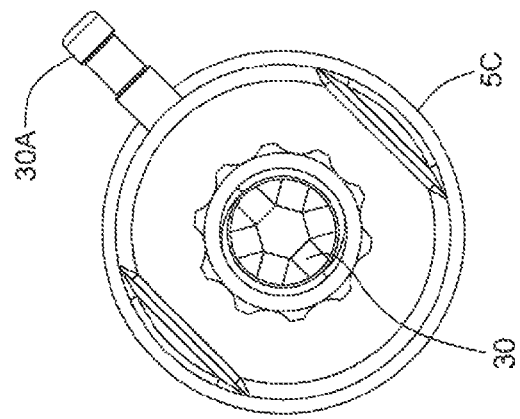
FIG. 2E3
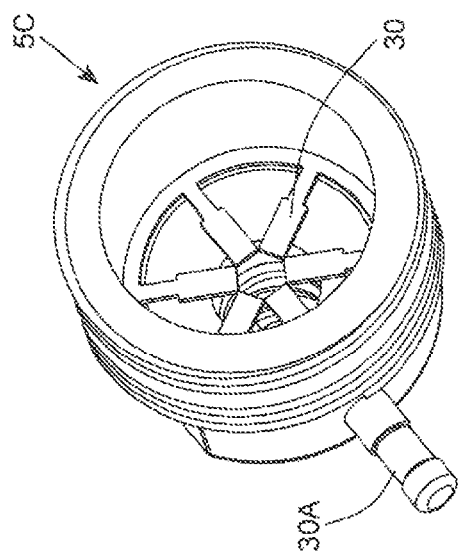
FIG. 2E2
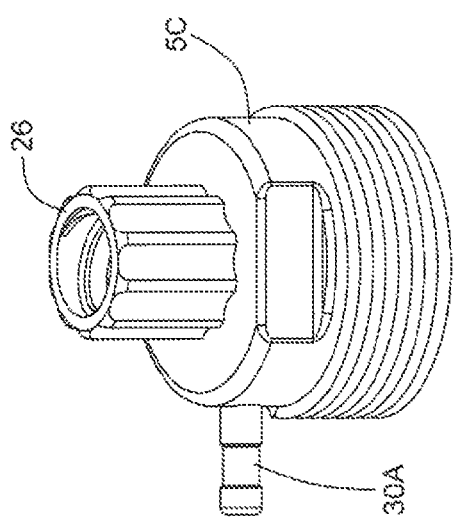
FIG. 2E1

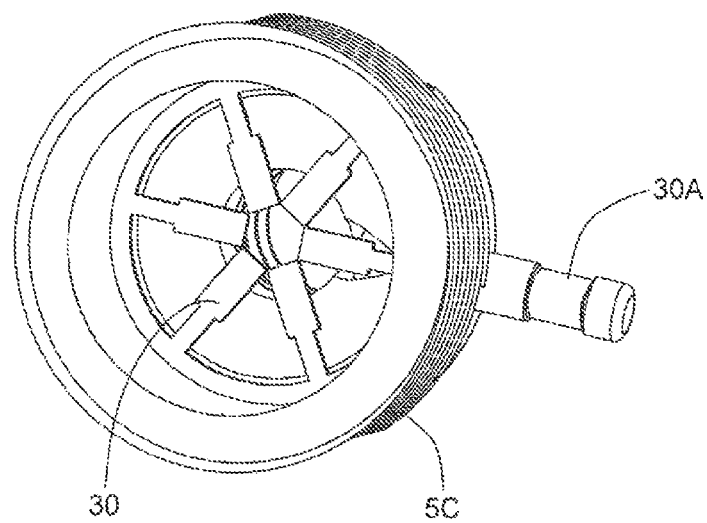
FIG. 2E4
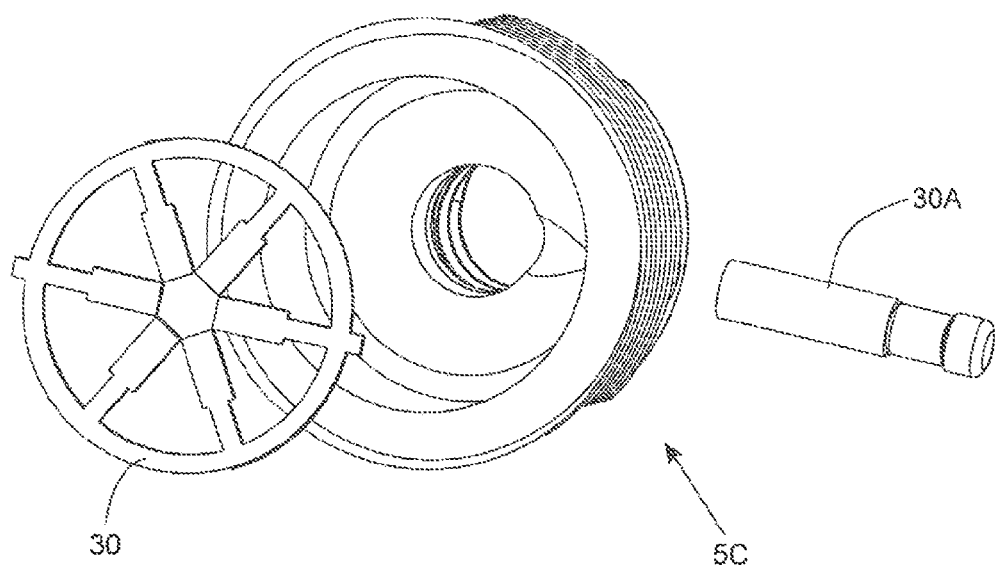
FIG. 2E5

```
'enable cautery if appropriate on forward stroke
IF VR(14)=1 THEN
  IF VR(11)=1 THEN
    WDOG=ON 'close cautery relay
  ELSE
    WDOG=OFF 'open cautery relay
  ENDIF
ENDIF
```

VR(14) Doc enabled cautery by pushing console button

VR(11) Cannula is not in the same position on this loop (2ms later) as last time

FIG. 2H

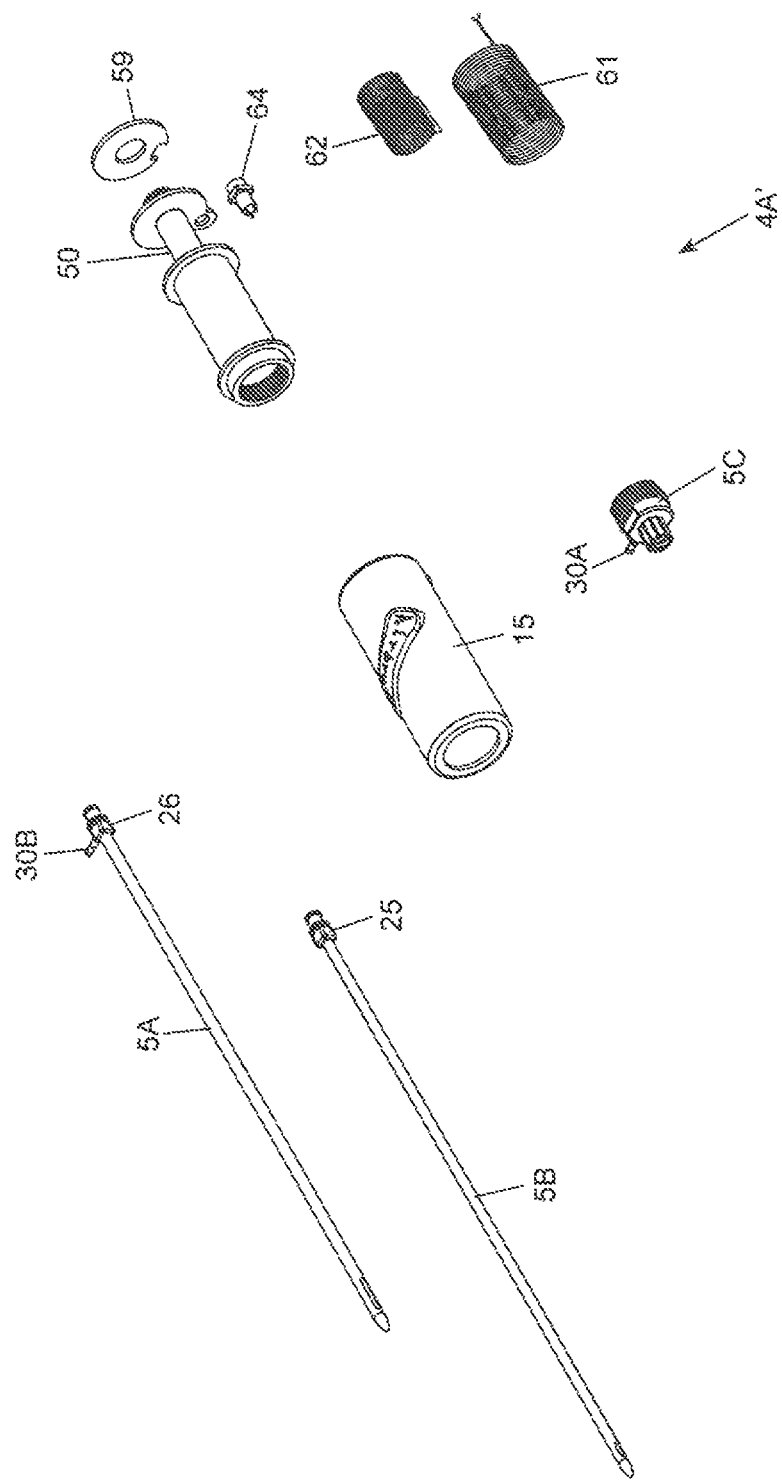
FIG. 3D1

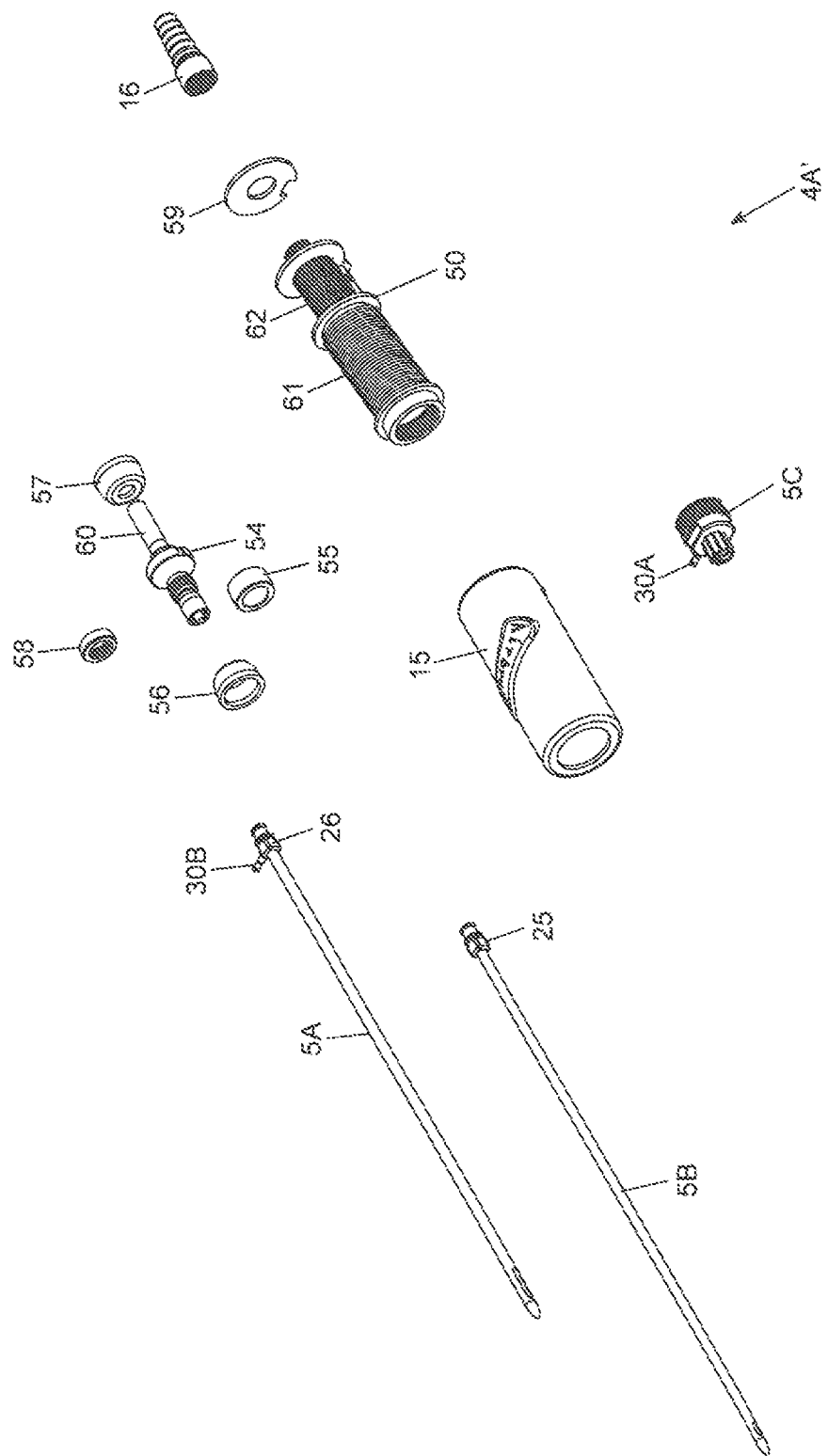
FIG. 3D2

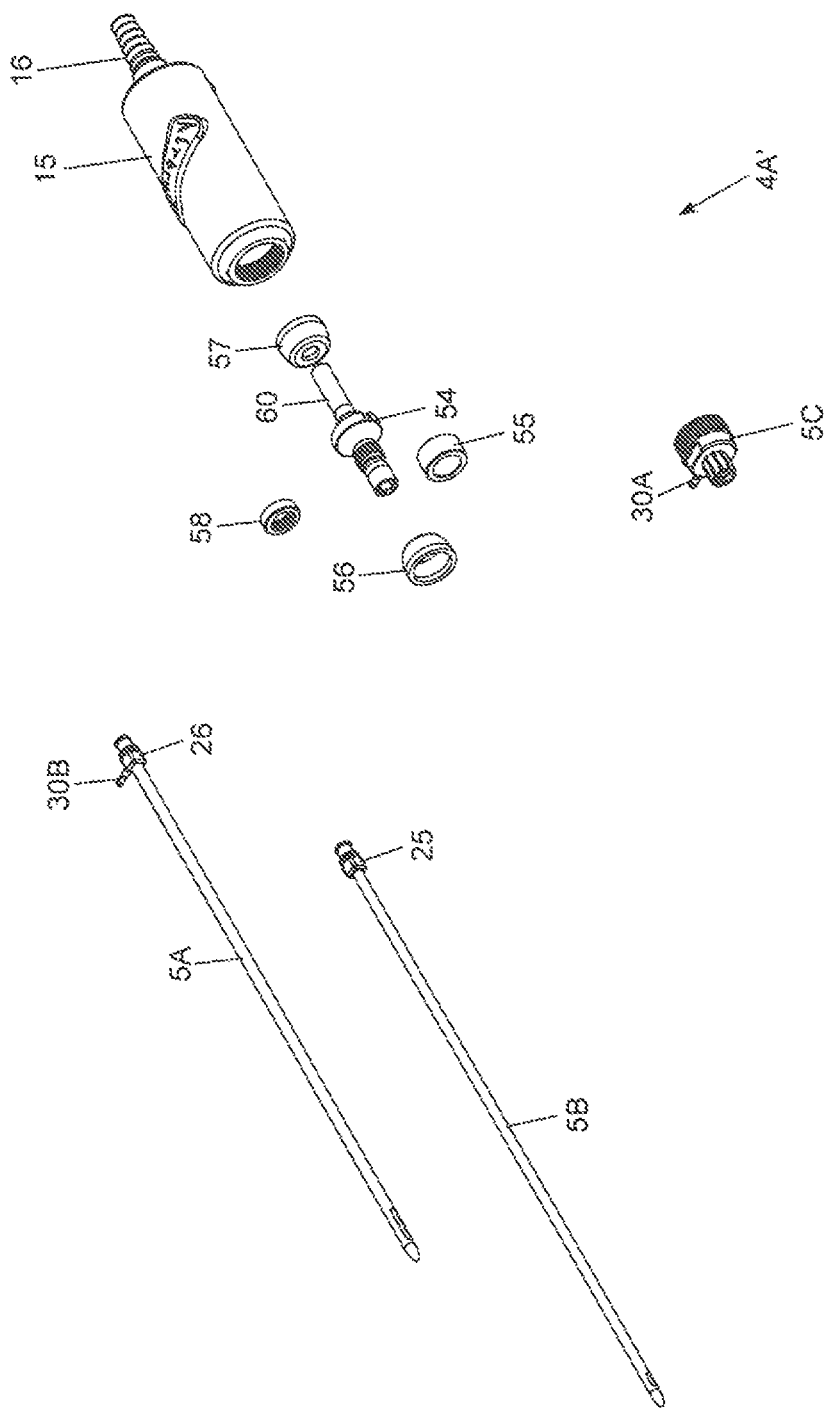
FIG. 3D3

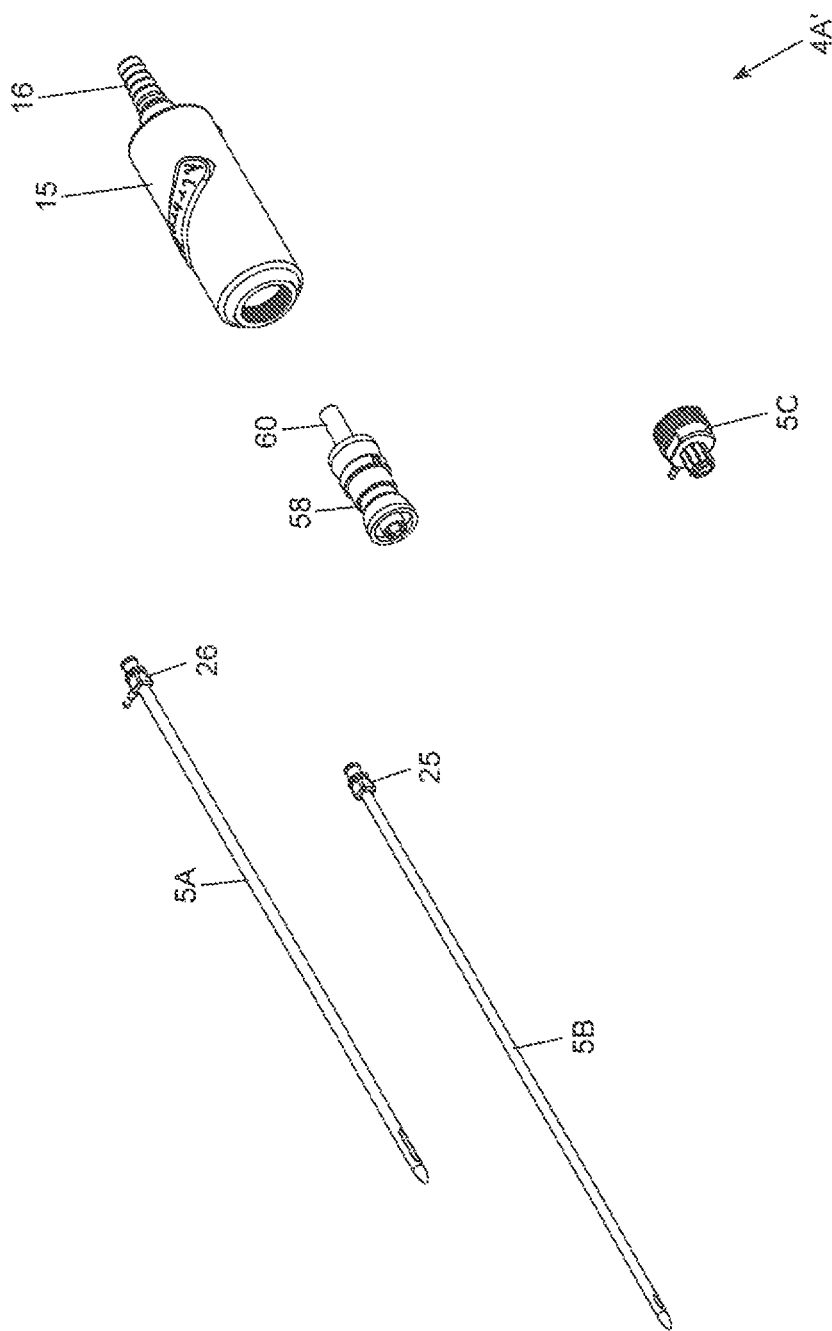
FIG. 3D4

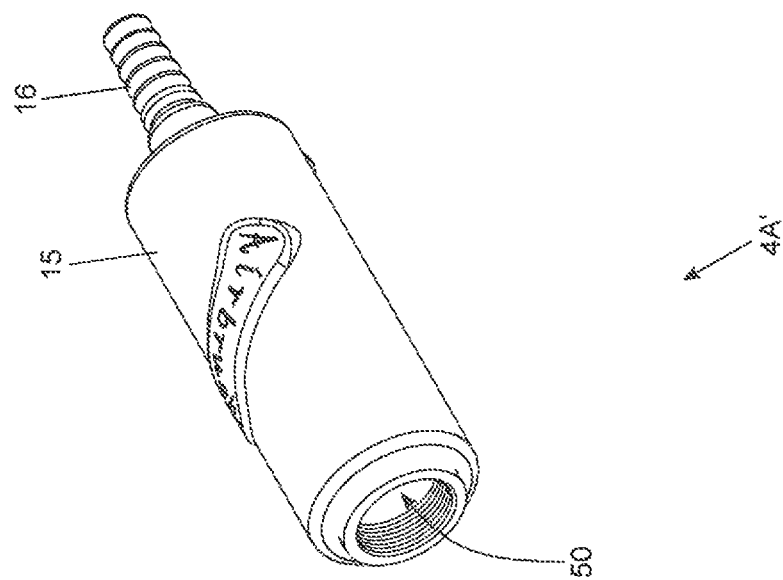
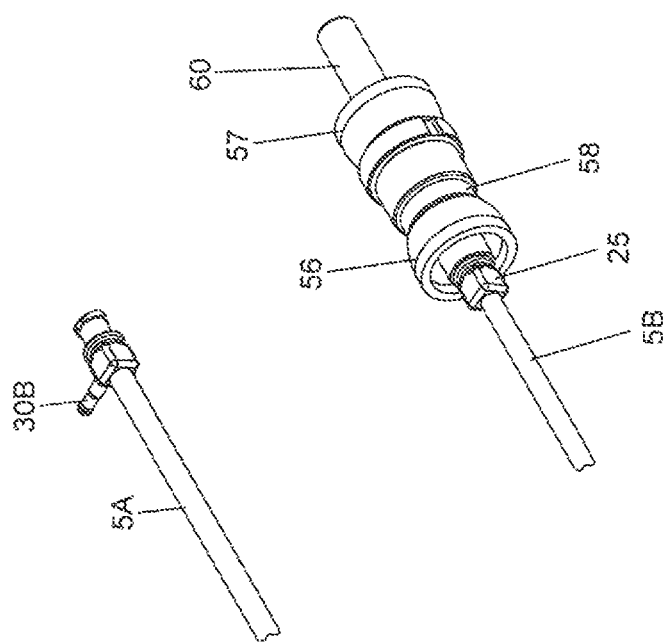
FIG. 3D5

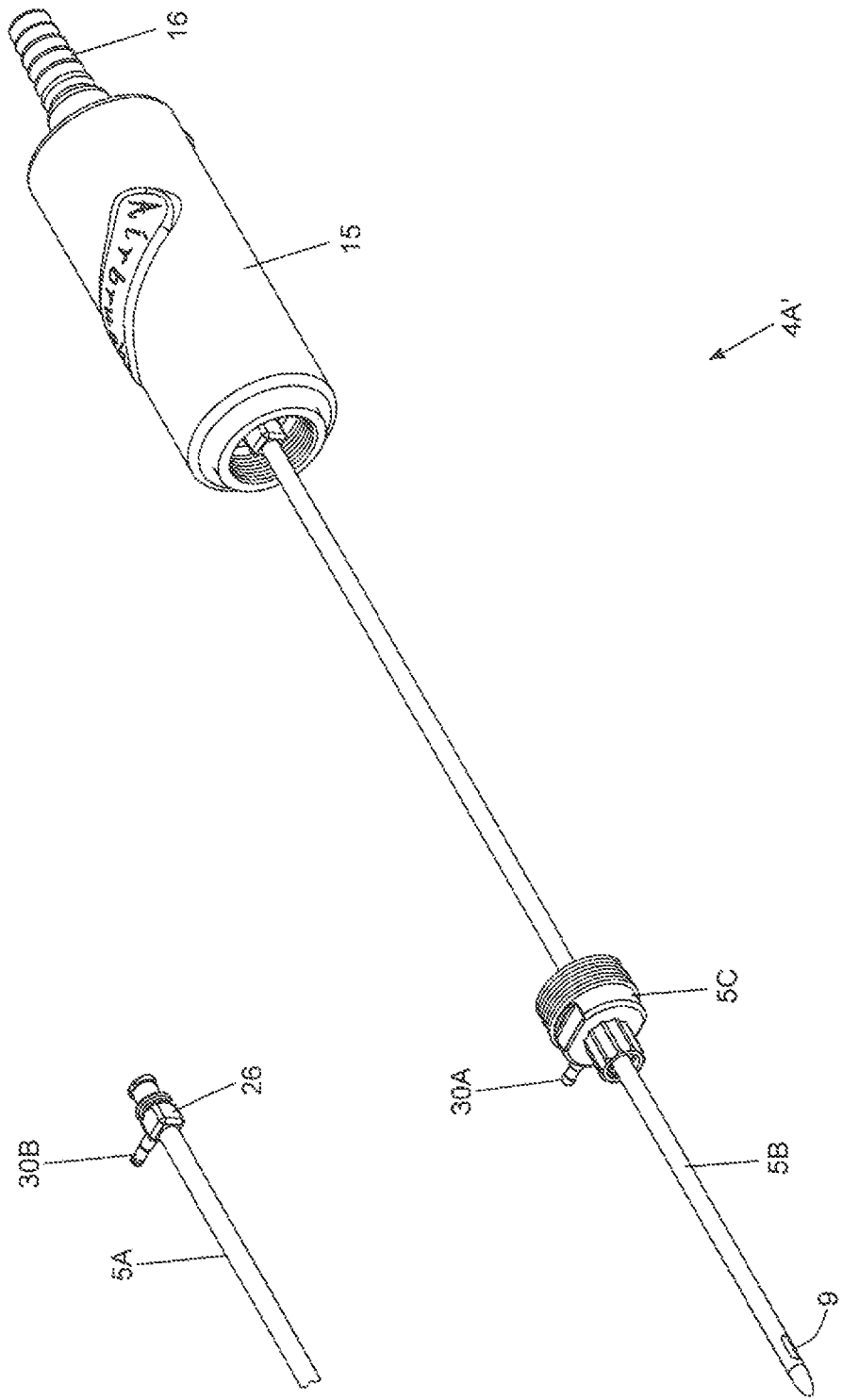
FIG. 3D6

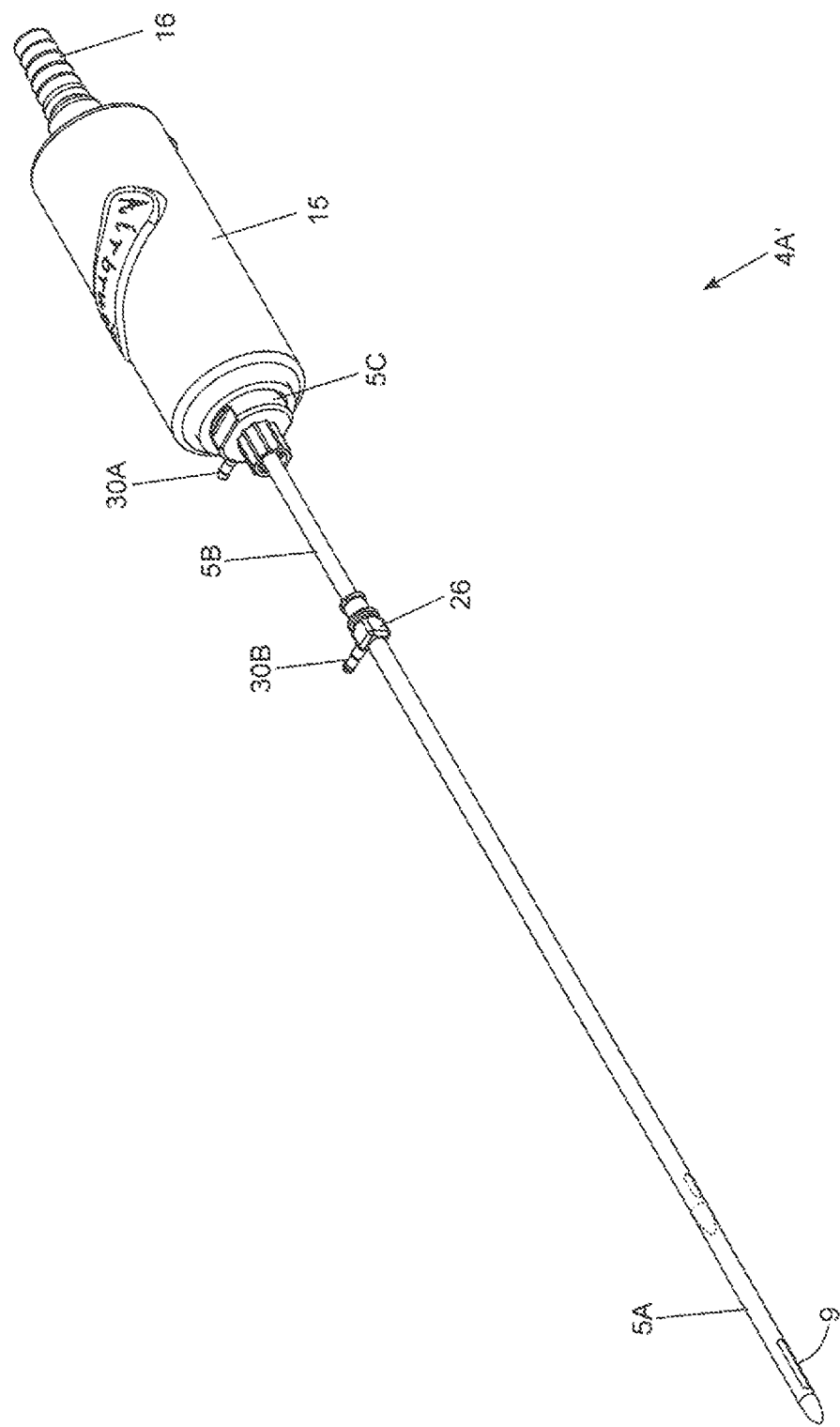
FIG. 3D7

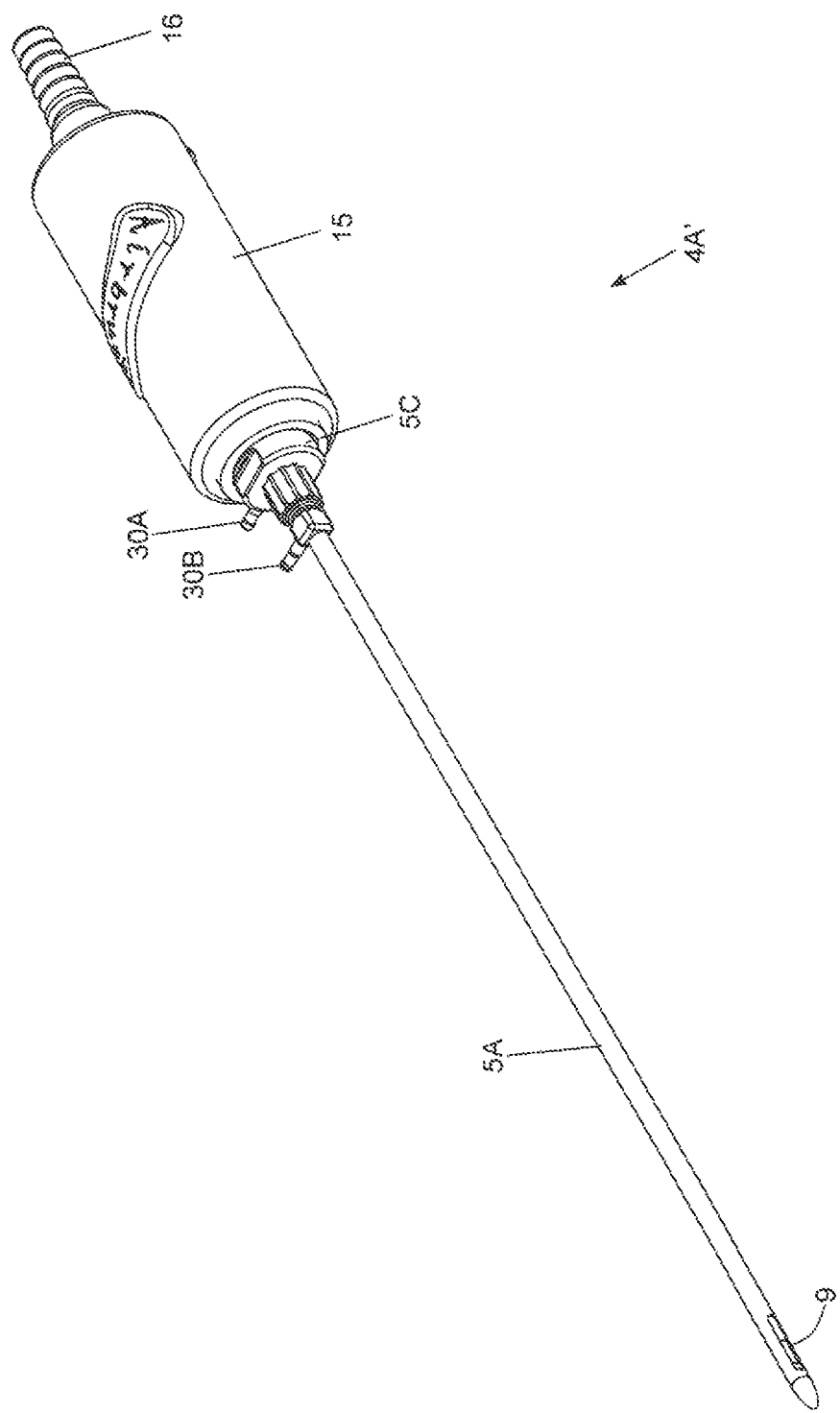
FIG. 3D8

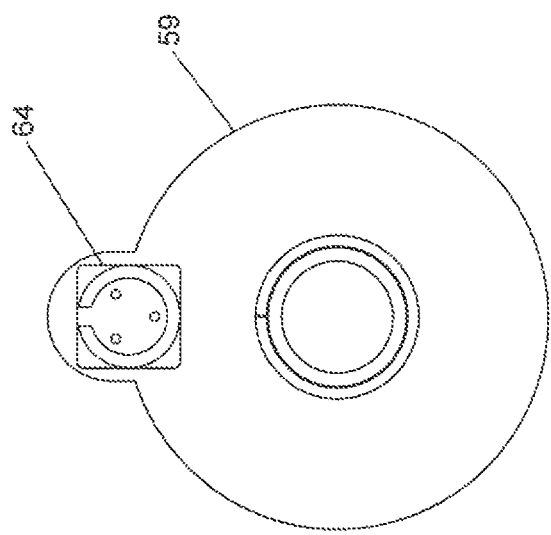
FIG. 3F1

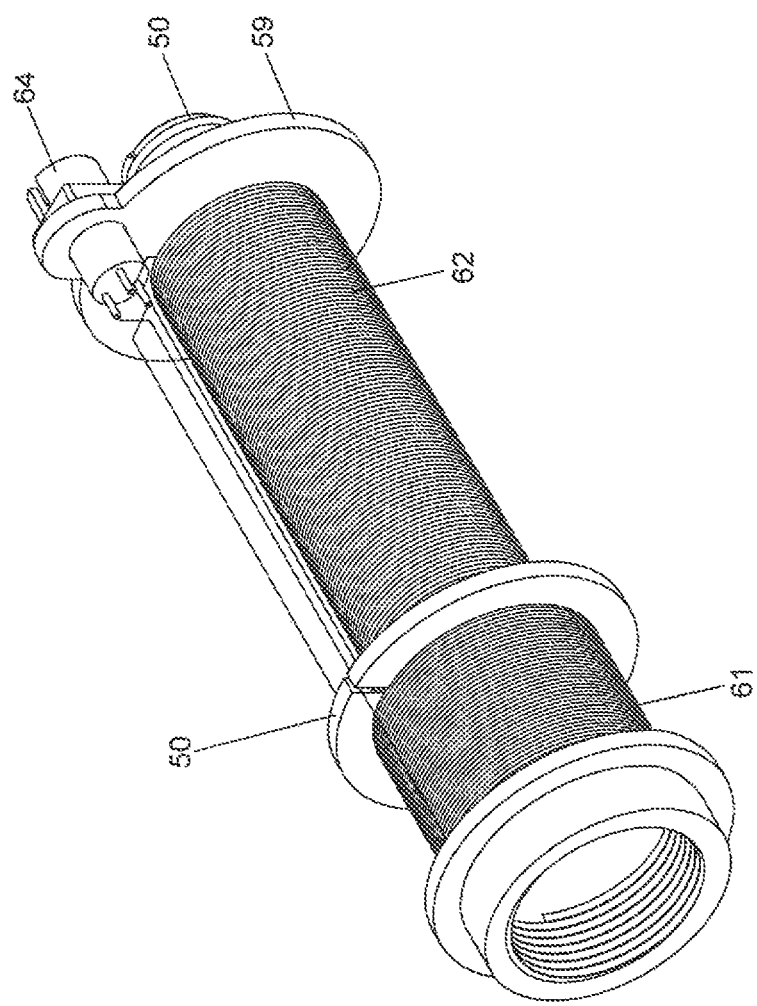
FIG. 3F2

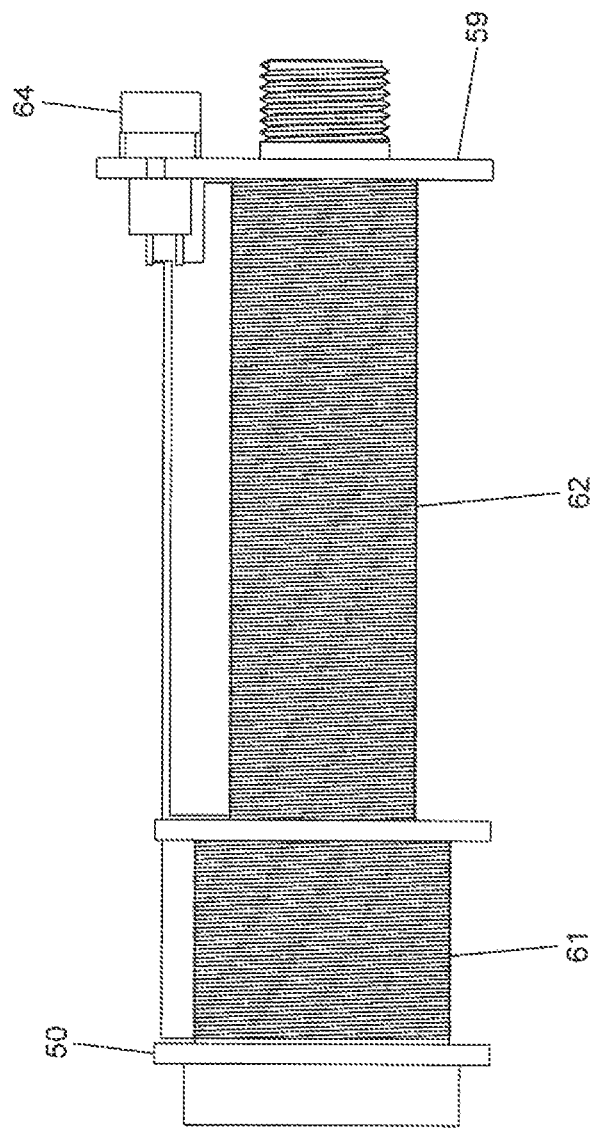
FIG. 3F3

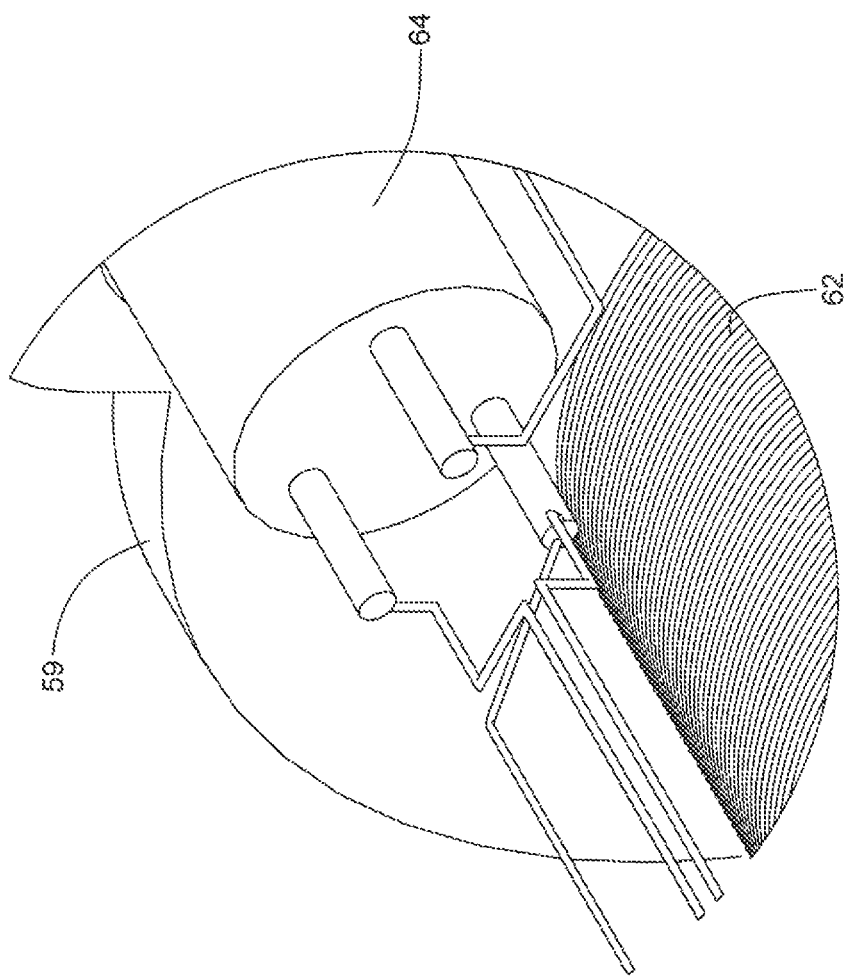
FIG. 3F4

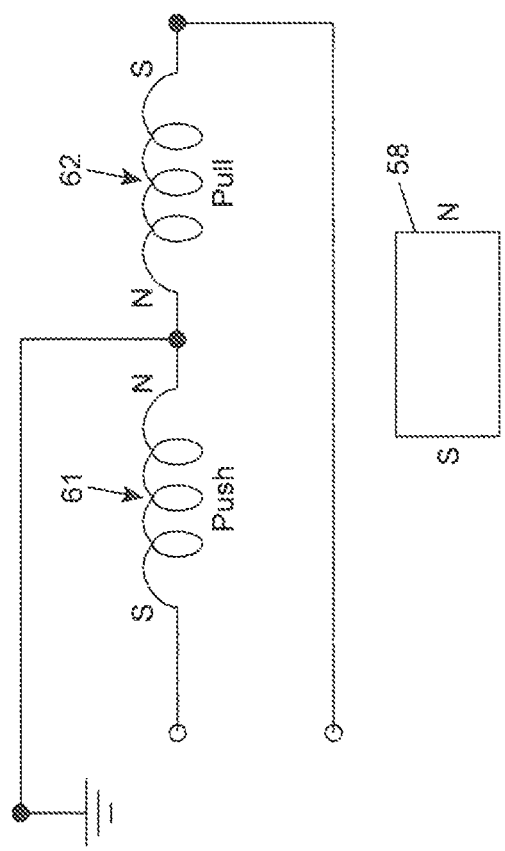
FIG. 3F5

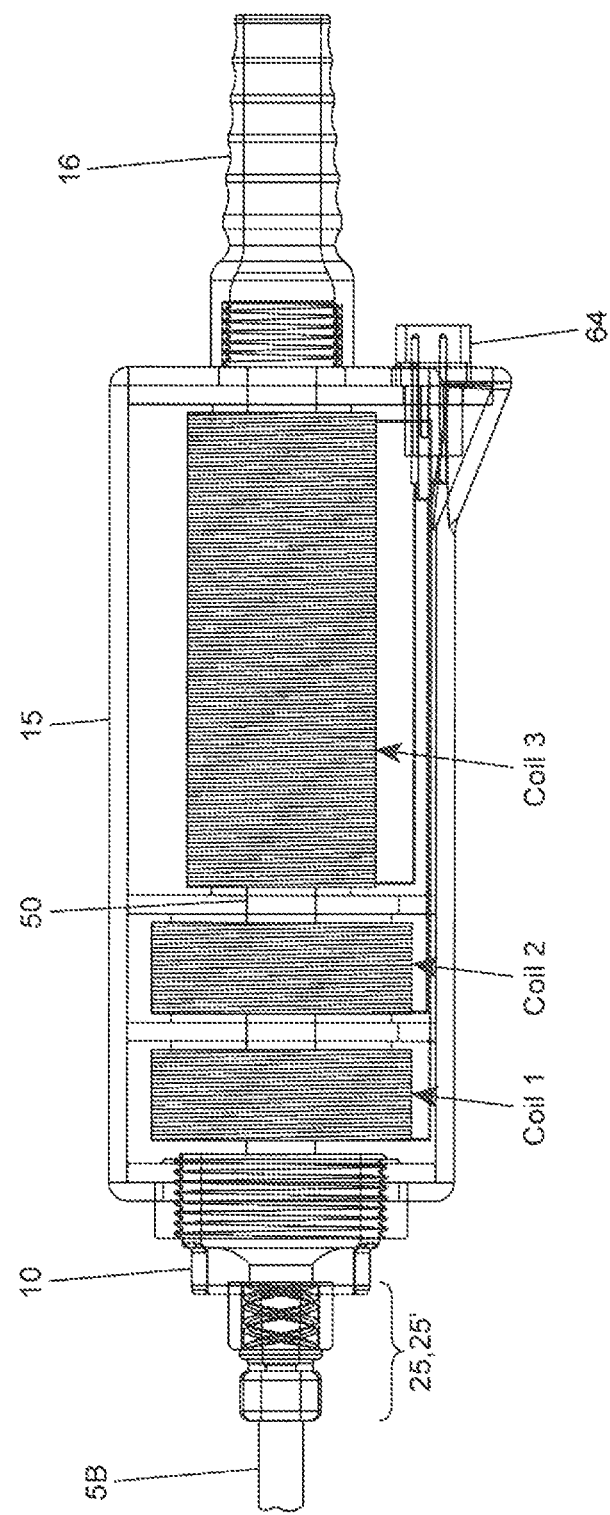
FIG. 3G1

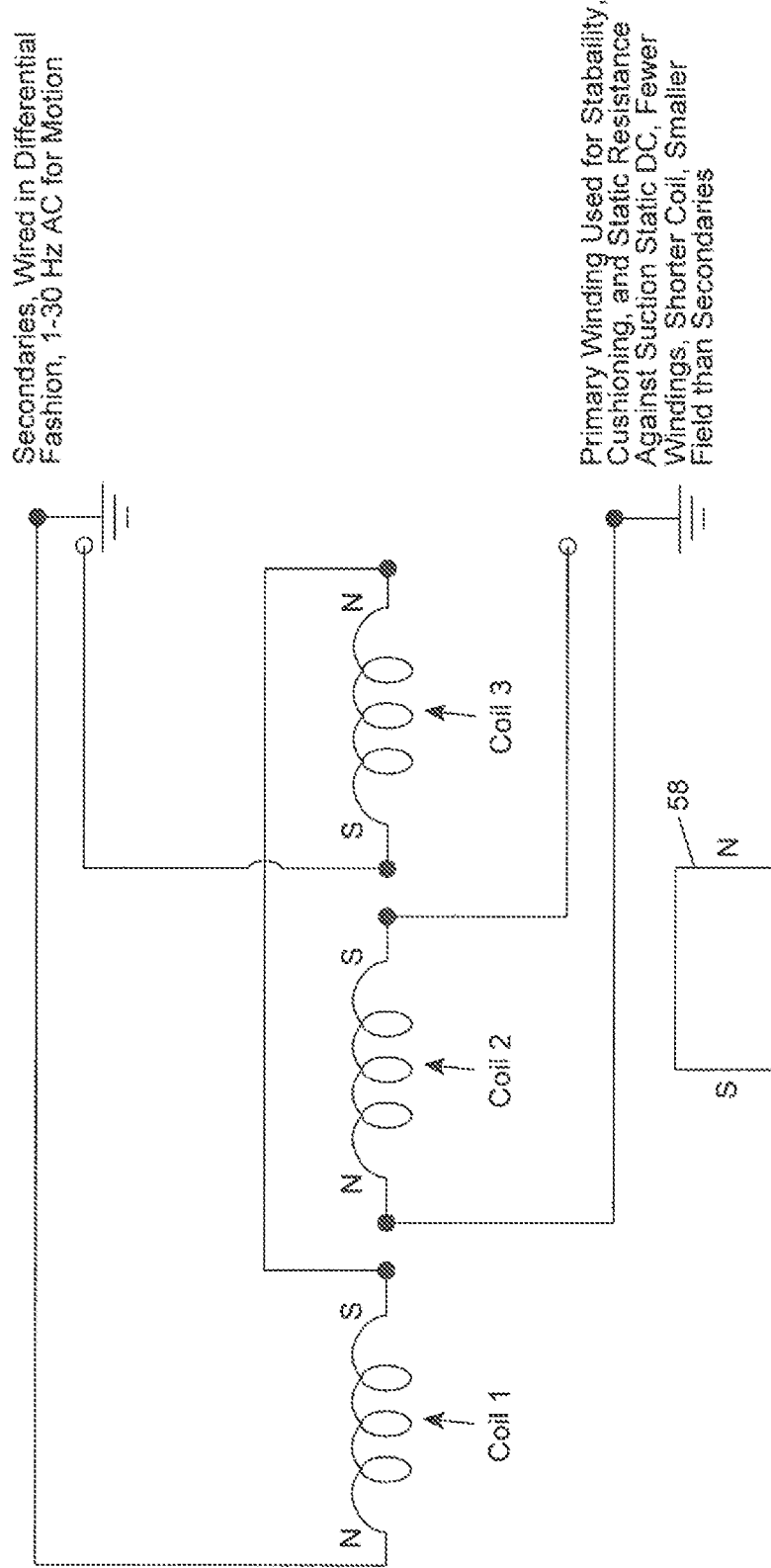
FIG. 3G2

```
'enable cautery if appropriate on forward stroke
IF VR(14)=1 THEN
  IF VR(11)=1 THEN
    WDOG=ON 'close cautery relay
  ELSE
    WDOG=OFF 'open cautery relay
  ENDIF
ENDIF
```

VR(14) Doc enabled cautery by pushing console button

VR(11) Cannula is not in the same position on this loop (2ms later) as last time

FIG. 3I

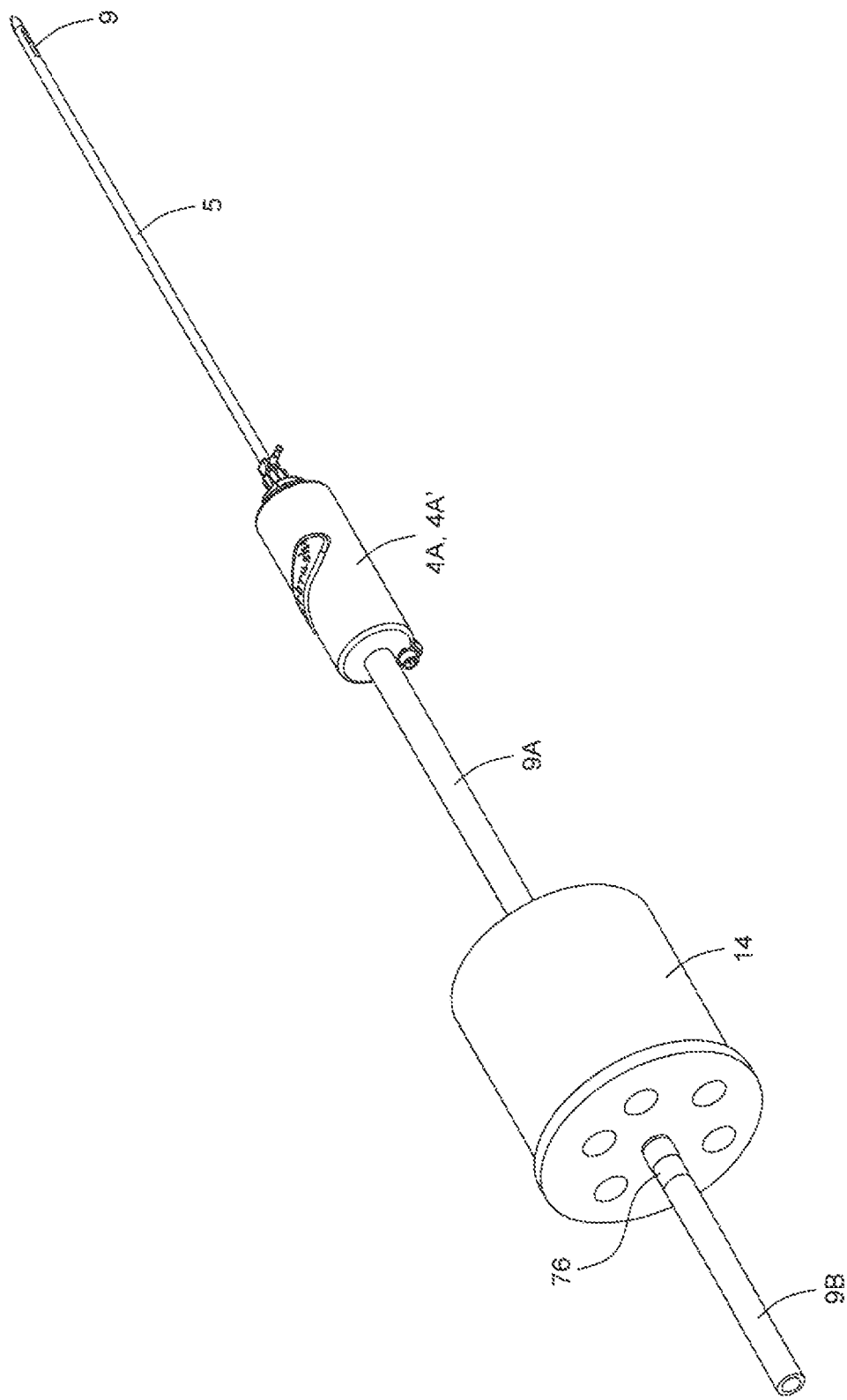

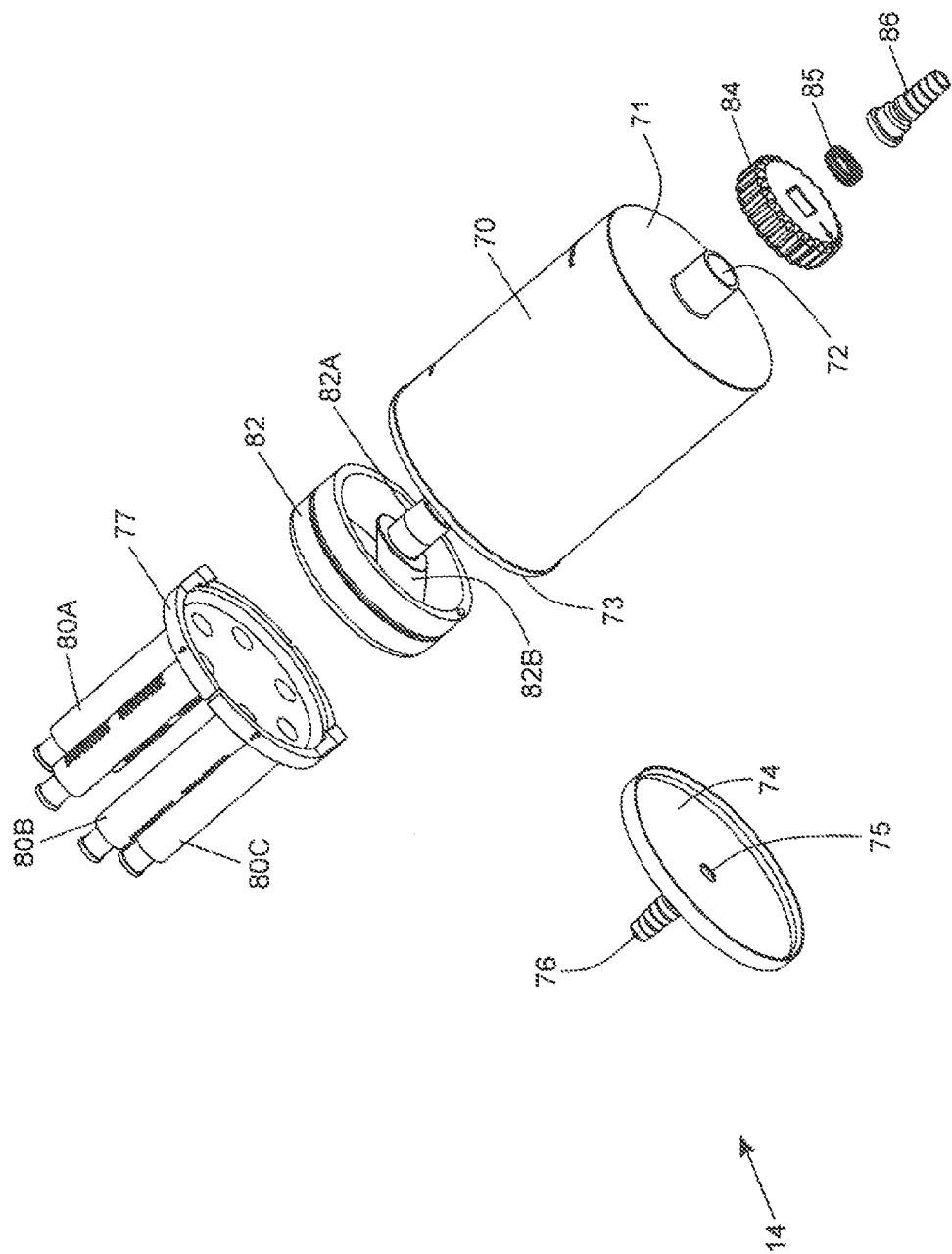

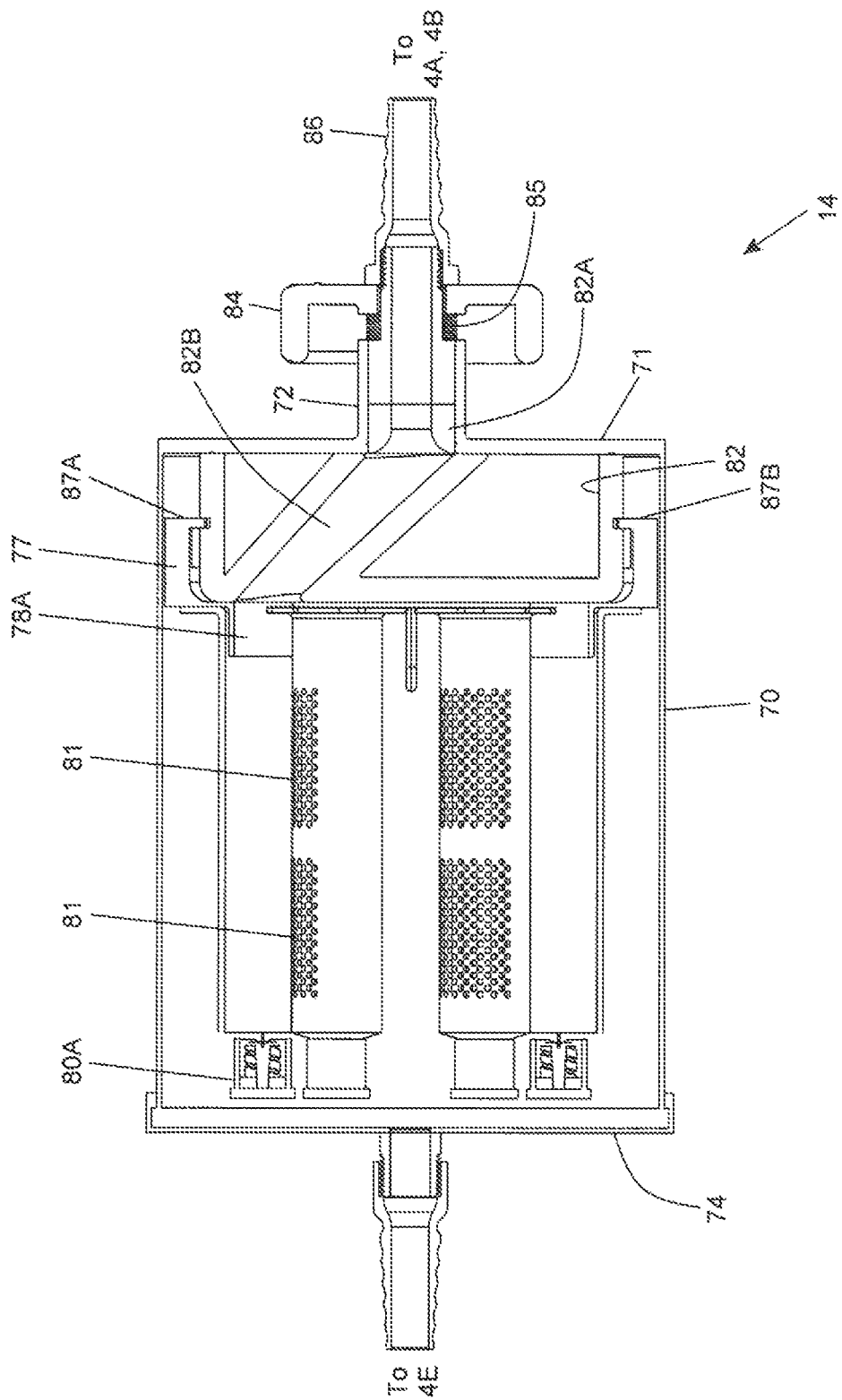
FIG. 4F1

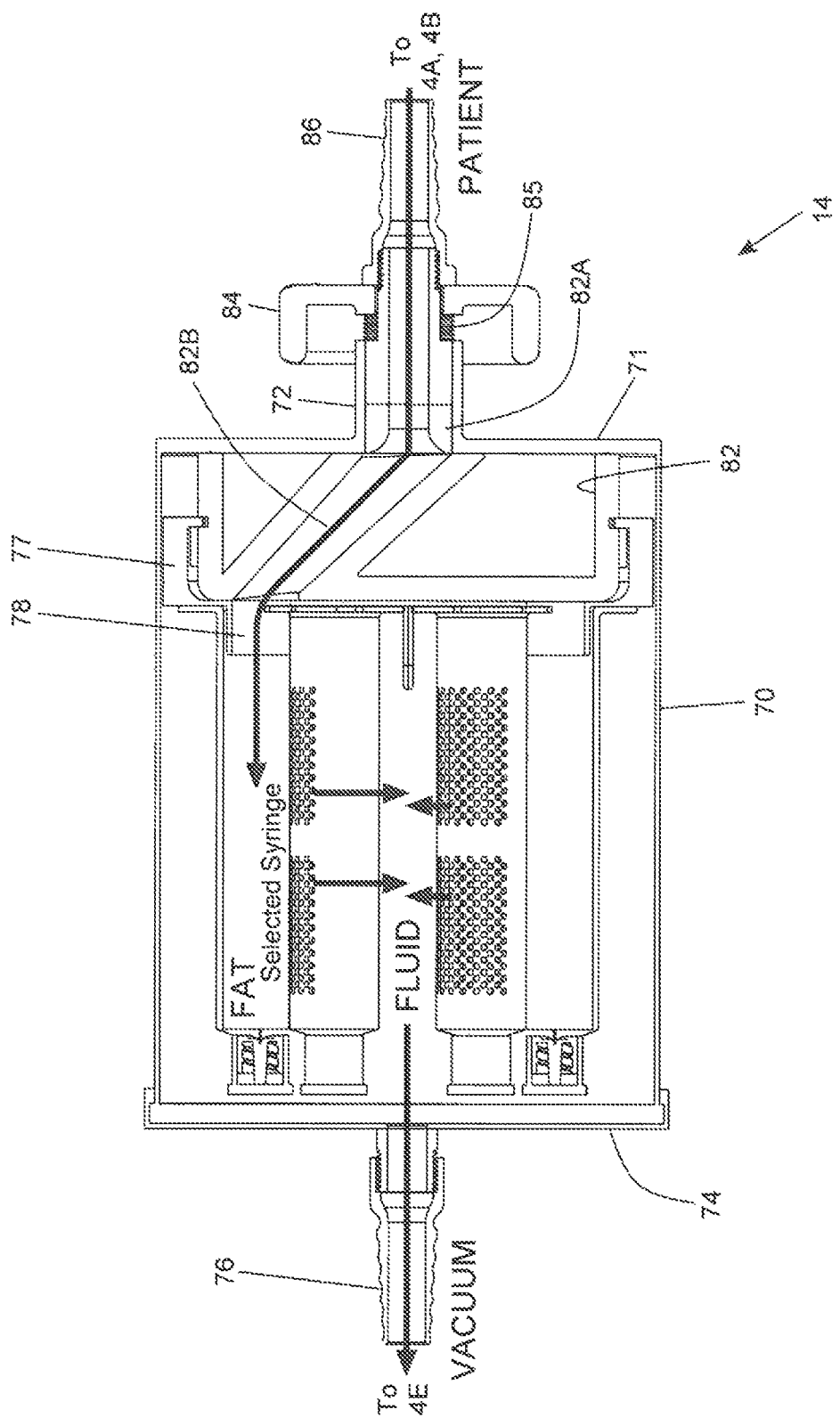

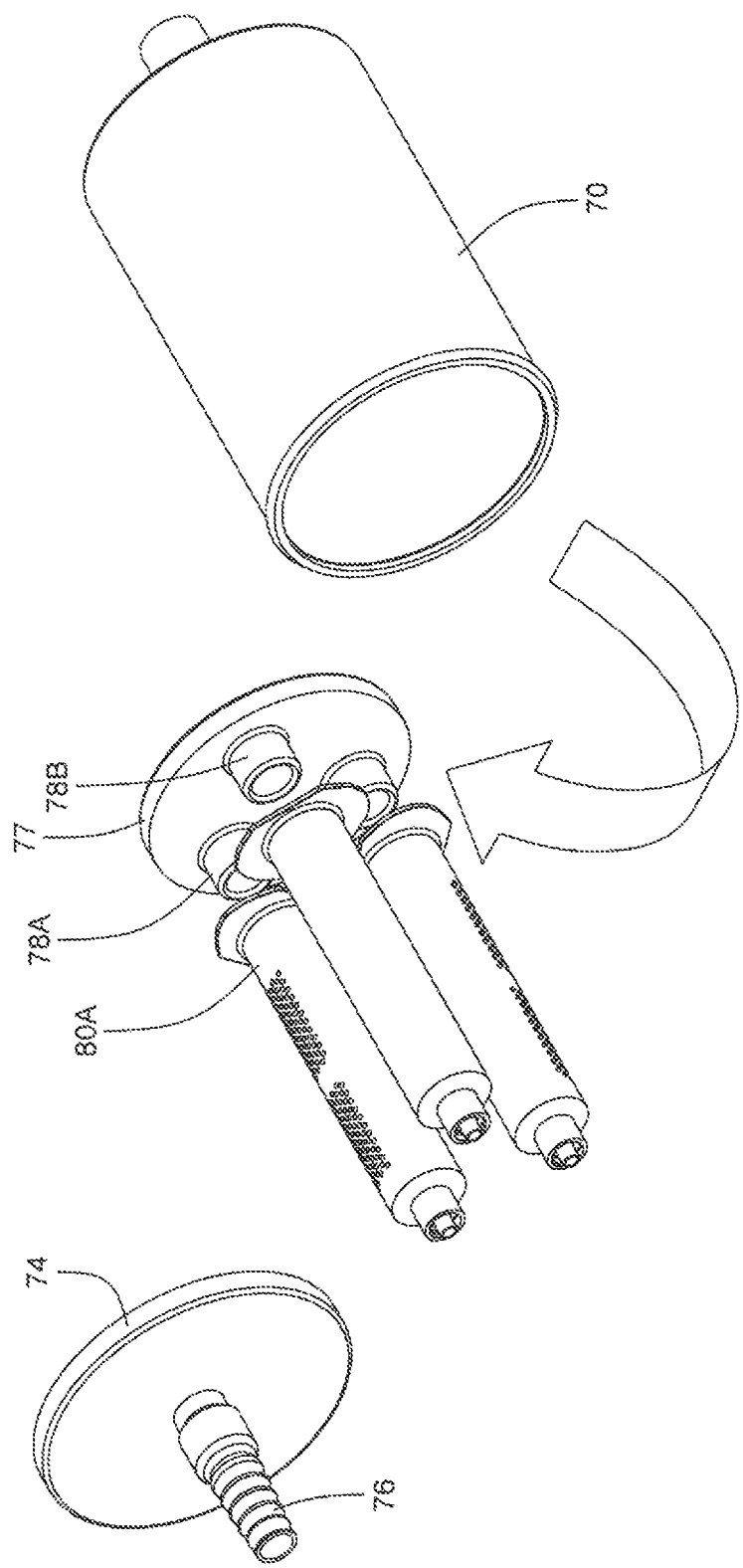

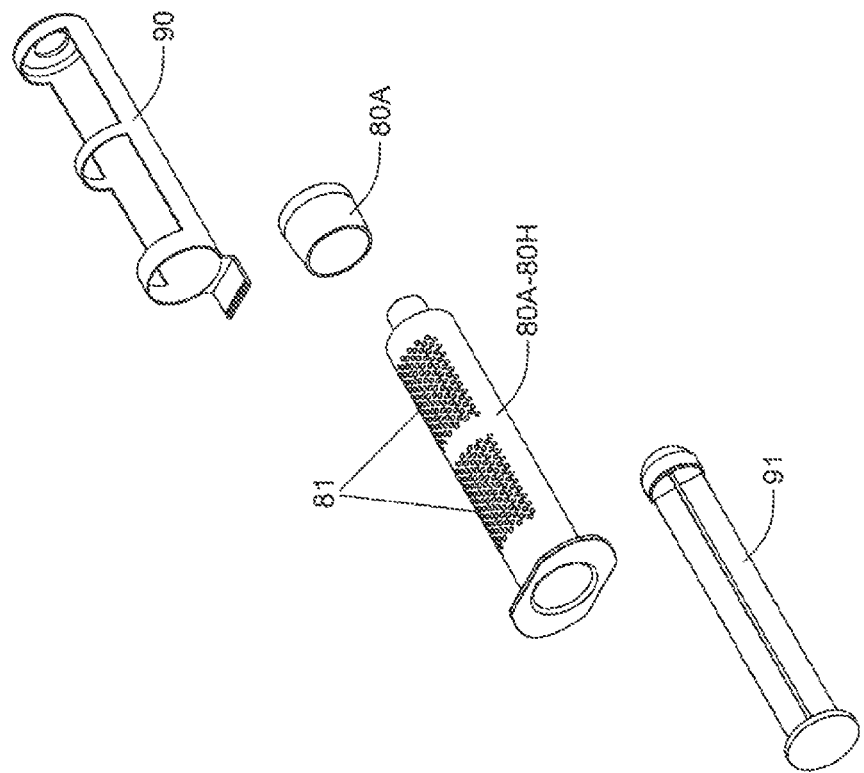

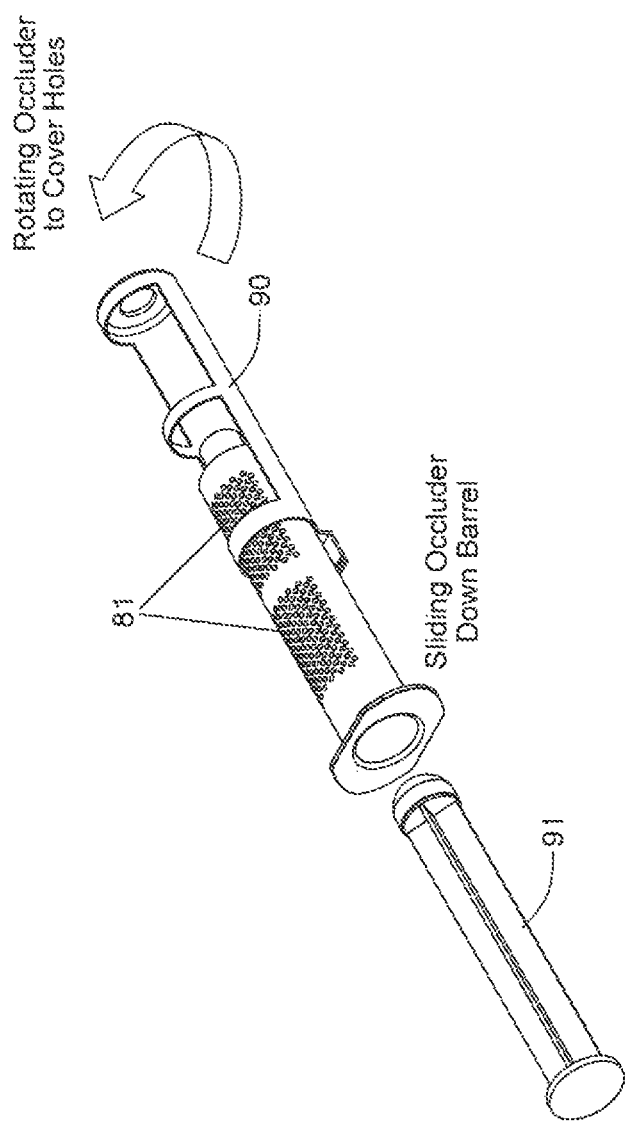

METHOD OF COLLECTING AND IN SITU PROCESSING OF ASPIRATED FAT TISSUE SAMPLED FROM A HUMAN PATIENT DURING TISSUE ASPIRATION OPERATIONS

RELATED CASES

This Application is a Continuation of application Ser. No. 12/850,786 filed Aug. 5, 2010; which is a Continuation-in-Part (CIP) of copending application Ser. No. 12/462,596 filed Aug. 5, 2009, and copending application Ser. No. 12/813,067 filed Jun. 10, 2010; wherein each said Application is owned by Rocin Laboratories, Inc., and incorporated herein by reference in its entirety.

BACKGROUND OF THE INVENTION

1. Field of the Invention

The present invention relates to a novel way of and means for treating abdominal obesity, metabolic syndrome and Type II diabetes mellitus in human patients.

2. Brief Description of the State of Knowledge in the Art

In general, there are three kinds of fat in the human body: subcutaneous fat, intramuscular fat, and visceral fat.

Subcutaneous fat is found underneath the skin, and intramuscular fat is found interspersed in skeletal muscle. Fat in the lower body, e.g. in thighs and buttocks, is subcutaneous. Visceral fat, also known as organ fat or intra-abdominal fat, is located inside the peritoneal cavity, packed in between the internal organs and torso of the abdomen. There are several adipose tissue deposits of visceral fat in the human body, namely: mesenteric, epididymal white adipose tissue, and perirenal deposits. [Adipose tissue as an endocrine organ Kershaw E E, Flier J S. J. Clin. Endocrinol. Metab. 89 (6): 2548-56 (2004).] An excess of visceral fat is known as central obesity, "belly fat," the "pot belly" or "beer belly," where the abdomen protrudes excessively.

Over 250 years ago, Johannes Baptista Morgagni described android obesity as increased intra-abdominal and mediastinal fat accumulation. Back then, he recognized the association between visceral obesity, hypertension, hyperuricemia, atherosclerosis, and obstructive sleep apnea syndrome. [Historical perspective: visceral obesity and its relation to morbidity in Johannes Baptista Morgagni's 'De sedibus et causis morborum per anatomen indagata' Enzi G, Busetto L, Inelmen E M, Coin A, Sergi G Int. J. Obes Relat Metab Disord 27: 534-535 (2003)]

Today, Morgagni's android obesity condition is now described as metabolic syndrome, and is associated with insulin resistance and increased risk of Coronary Heart Disease. The Metabolic syndrome is a condition defined by any three of five risk factors, one of which is waist circumference (female waist >88 cm (>35"), male waist >102 cm.(>40"). The others are triglycerides: (men <40 mg/dl; women <50 mg/dl), HDL cholesterol (≥110 mg/dl), blood pressure (≥130/≥85 mm Hg), and FBS (>150 ml/dl). [Dyslipidemia of central obesity and insulin resistance. Brunzell, J D, Hokanson, J E Diabetes Care: 22(3); Mediastinal fat, insulin resistance and hypertension. Sharma AM Hypertension: 44:117 (2004)].

Over the past 40 years, the prevalence of obesity in the US increased from 13% to 32%. In 2003-2004, 66% of U.S. adults were overweight or obese.

Abdominal obesity as measured by waist circumference and waist hip ratio (WHR) is an independent predictor of mortality. Marginally increased waist circumference is strongly associated with prevalent hypertension in normal-weight and overweight adults. Also, there is a strong correlation between central (i.e. abdominal) obesity and cardiovascular disease. [Effect of potentially modifiable risk factors associated with myocardial infarction in 52 countries. Yusuf S, Hawken S, Ounpu S, Dans T, Avezum A, Lanas F, McQueen M, Budaj A, Pais P, Varigos J, Lisheng L, Lancet 364: 937-52 (2004).] Because of this, the WHR ratio has been used as a measure of obesity and is an indicator or measure of the health of a person, and the risk of developing serious health conditions. Research shows that people with "apple-shaped" bodies (with more weight around the waist) face more health risks than those with "pear-shaped" bodies who carry more weight around the hips. [Waist-hip ratio should replace Body Mass Index as an indicator of mortality risk in older people. Am. J. Clin. Nutrition (Aug. 12, 2006).]

A WHR of 0.7 for women and 0.9 for men have been shown to correlate strongly with general health and fertility. Women within the 0.7 range have optimal levels of estrogen and are less susceptible to major diseases such as diabetes, cardiovascular disorders and ovarian cancers. Men with WHR's around 0.9, similarly, have been shown to be more healthy and fertile with less prostate cancer and testicular cancer. Studies show that 80 percent of women over the age of 18 have a WHR of at least 0.9. This is a 40 percent increase since 2002, and it keeps increasing.

Although maintaining a healthy weight is a cornerstone in the prevention of chronic diseases and premature death, maintaining a healthy waist size should also be an important goal.

Markedly obese patients are typically directed towards diet and exercise programs, and failing that, presented with the option of bariatric surgery or living with and dying from the increased morbidity of obesity. After bariatric surgery, plastic surgeons perform skin excisions of the redundant folds of tissue remaining on patients who had lost 50-200 lbs. These post-bariatric surgery patients are frequently nutritional cripples with hypoalbuminemia, cirrhosis, and renal stones and suffer increased complications reflecting their impaired nutritional status.

Traditional plastic surgical approaches have been cosmetic, targeted only at removing (i) localized subcutaneous fat deposits in non-obese or modestly obese patients, and (ii) the redundant folds of abdominal wall or pannus that remain after massive weight loss from gastric banding or intestinal bypass procedures.

Before subcutaneous visceral fat aspiration, combined hemostasis and analgesia is achieved in the patient by infusing tumescent solutions of lactated Ringer's solution, containing dilute amounts of xylocaine and epinephrine. Performing tumescent visceral fat aspiration in this manner allows increased volumes of fat to be removed and obviates the need for general anaesthesia which, in turn, facilitates outpatient surgery in office-based facilities. [Tumescent Technique Klein, J. Mosby (2000).]

Studies have now shown large volume subcutaneous fat aspiration and abdominoplasty as feasible alternatives for improving body shape. [Large-volume visceral fat aspiration and extensive abdominoplasty: a feasible alternative for improving body shape. Cardenas-Camarena L, Gonzalez L E Plast Reconstr Surg. 102: 1698-707 (1998).]

Clinical studies have shown large volumes of fat can be safely removed in serial visceral fat aspiration procedures performed at safe intervals. Pilot studies have also shown improvement in the cardiovascular risk profile with large volume subcutaneous visceral fat aspiration. [Improvements in cardiovascular risk profile with large-volume visceral fat aspiration: a pilot study. Giese S Y, Bulan E J, Commons G W, Spear S L, Yanovski J A. Plastic Reconstr Surg. 108 510-21 (2001).]

However, it should be noted that such large volume subcutaneous fat aspiration approaches are still mainly cosmetic, as only the less metabolically active, subcutaneous fat is addressed and removed during such procedures.

Recently, animal research has discovered that only the removal of visceral fat in mice has been shown to stop insulin resistance. [Visceral fat removal stops insulin resistance. Barzilai N. Diabetes 51: 2951-2958 (2002).] Increased visceral fat shortens mammalian longevity and its removal lengthens it. [Visceral adipose tissue modulates mammalian longevity. Muzumdar R., Allison D B, Huffman, D M, Xiaohui M, Einstein, F H, Fishman S, Poduval A D, McVei T, Keith, S W, Barzilai, N. Aging Cell 7(3) 438-440 (2008).] [The effect of fat removal on glucose tolerance is depot specific in male and female mice. Haifei S, Strader A D, Woods, S C, Seeley, R J Am. J. Physiol Endocrinol Metab 293: E1012-1020 (2007).]

Adipose tissue is a metabolically active tissue and serves as an important endocrine organ. The hypertrophic fat cells of adipose tissue in obese patients produce increased quantities of leptin and tumor necrosis factor-a (TNF-a) and are less sensitive to insulin. Studies have revealed effect of visceral fat aspiration on insulin resistance and vascular inflammatory markers in obese women. Giugliano G, Nicoletti G, Grella E, Giugliano F, Esposito K, Scuderi N, D'Andrea F. Br J Plast Surg. 2004 Apr; 57(3): 190-4.) The most important secreted products of fat cells are leptin, resistin, tumornecrosisfactor-a (TNF-a), and adiponectin. The first three products are increased in obese patients as a result of increased production by enlarged fatcells. In contrast, adiponectin, which improves glucose handling by peripheral tissues, is present at lower levels in obese patients [Bastard J P, MaachiM, van Nhieu J T, Jardel C, Bruckert E. Grimaldi A, Robert J J, Capeau J, Hainque B: Adipose tissue content correlates with resistance to insulin activation of glucose uptake both invivo and invitro. J Clin Endocrinol Metab 87:2084-2089, 2002; Borst S E: The role of TNF-alpha in insulinresistance. Endocrine23: 177, 2004; Fernandez-Real J M, Lopez-Bermejo A, Casamitjana R, et al.: Novel interactions of adiponectin with the endocrine system and inflammatory parameters. J Clin Endocrinol Metab 88:2714-2718, 2003; Rashid M N, Fuentes F, Touchon R C, Wehner P S:Obesity and the risk for cardiovascular disease. Prey Cardio 16: 42-47, 2003].

Hypertrophic fat cells present in the subcutaneous tissue of obese patients generally produce increased quantities of secreted products such as leptin [Friedman J M: Obesity in the new millennium. Nature 404: 632,2000] and TNF-a [Hotamisligil G S, Shargill N S, Spiegelman B M:Adi-pose expression of tumor necrosis factor-alpha: Direct role in obesity-linked insulin resistance. Science 259:87, 1993], but are less sensitive to insulin in vivo and in vitro [Chlouverakis C, Hojnicki D: Effect of fat cell size on its sensitivity to insulin measured by a new method. Steroids Lipids Res 5:351,1974; Olefsky J M: Mechanism of decreased responsiveness of large adipocytes. Endocrinology 100:1169, 1977].

Many studies assert that excising a large amount of subcutaneous fat by large-volume visceral fat aspiration (LVL) is metabolically safe [Giese S Y, Bulan E J, Commons G W, et al.: Improve-ments in cardiovascular risk profile with large-volume visceral fat aspiration: A pilot study. Plast Reconstr Surg 108:510, discussion 520, 2001; Gonzalez-Ortiz M, Robles-Cervantes J A, Cardenas-Camarena L, et al.: The effects of surgically removing subcutaneous fat on the metabolic profile and insulin sensitivity in obese women after large-volume liposuction treatment. Horm Metab Res 34:446,2002; Robles-Cervantes J A, Yanez-Diaz S, Cardenas-Camarena L: Modification of insulin, glucosa, and choles-terol levels in nonobese women undergoing visceral fat aspiration. Ann Plast Surg 52:64,2004] and associated with improvement in inflammatory markers and insulin sensitivity in obese women [Giugliano G, Nicoletti G, Grella E,et al.:Effect of visceral fat aspiration on insulin resistance and vascular inflammatory markers in obesewomen. Br J Plast Surg 57:190, 2004; Gonzalez-Ortiz M, Robles-Cervantes J A, Cardenas-Camarena L, et al.: The effects of surgically removing subcutaneous fat on the metabolic profile and insulin sensitivity in obese women after large-volume visceral fat aspiration treatment. Horm Metab Res 34:446,2002] and nonobese women [Robles-Cervantes J A, Yanez-Diaz S, Cardenas-Camarena L: Modification of insulin, glucose, and cholesterol levels in nonobese women undergoing visceral fat aspiration. Ann Plast Surg 5 2:64,2004]

Also, it is known that visceral fat cells within the abdomen have their secretions poured directly in to the portal blood circulation with a much more profound effect on metabolism. Human mesenteric adipose tissue in obese diabetic subjects has high basal glycerol release and impaired isoproterenol stimulated glycerol release. The obesity-related gene expressions in the mesenteric adipose tissue are up regulated, suggesting that the alterations of these genes in mesentery adipose depot may play a critical role in insulin resistance of type 2 diabetes and metabolic syndrome. [Cell Physiol Biochem. 2008; 22(5-6):531-8. Epub 2008 Dec 9. Human mesenteric adipose tissue plays unique role versus subcutaneous and omental fat in obesity related diabetes. Yang Y K, Chen M, Clements R H, Abrams G A, Aprahamian C J, Harmon C M.]

In Brazil, clinical trials are being carried out with partial omentectomy to determine the effect on insulin sensitivity. However, such studies have used direct surgical excision, posing high risk of vascular injury, with concomitant bleeding and vascular compromise of the intestine. [Surgical removal of visceral fat tissue (omentectomy) associated to bariatric surgery: effect on insulin sensitivity. Clinical Trials NCT00545805 University of Campinas, Brazil].

Thus, while there is great promise that the removal of visceral fat in the mesenteric region of human patients stands to ameliorate the metabolic syndrome and abdominal obesity, and reduce morbidity due to obesity, there is a great need in the art for a new and improved method of and apparatus for safely removing visceral fat in human patients, without employing conventional direct surgical excision techniques, and posing high risk of vascular injury with concomitant bleeding and vascular compromise of the intestine, associated with conventional surgical procedures and apparatus.

OBJECTS OF THE PRESENT INVENTION

Accordingly, it is a primary object of the present invention to provide a new and improved method of and apparatus for safely removing mesenteric fat in human patients to ameliorate the metabolic syndrome, or abdominal obesity, while avoiding the shortcomings and drawbacks of conventional surgical procedures and apparatus.

Another object of the present invention is to provide such an apparatus in the form of a laparoscopically-guided intra-abdominal visceral fat aspiration system including a powered hand-supportable fat aspiration instrument held by a surgeon and having an electro-cauterizing, irrigating and fiber-illuminating twin-cannula assembly for the safe removal of visceral fat from the mesenteric region of a patient, through a small incision in the patient's body.

Another object of the present invention is to provide such a laparoscopically-guided intra-abdominal visceral fat aspiration system, designed for safely removing visceral fat from the mesenteric region of a patient.

Another object of the present invention is to provide such a laparoscopically-guided intra-abdominal visceral fat aspiration system, wherein twin-cannula assembly support bipolar electro-cauterization about the aspiration aperture of a moving inner cannula, supported in a stationary outer cannula connected to the hand-supportable housing of the instrument.

Another object of the present invention is to provide a novel method of and apparatus for performing laparoscopic mesenteric visceral fat aspiration for ameliorating the metabolic syndrome, or abdominal obesity of the patient.

Another object of the present invention is to provide such a method comprising the steps of inserting a laparoscopic instrument and an electro-cauterizing visceral fat aspiration instrument into the mesenteric region of a patient, for the purpose of safely removing visceral fat to ameliorate the metabolic syndrome, or abdominal obesity of the patient.

Another object of the present invention is to provide a novel method of laparoscopically-guided intra-abdominal visceral fat aspiration, involving the simultaneously infusion of a tumescent solution into the mesenteric region of treatment, while synchronizing that infusion with the forward or return ("action") stroke of the inner cannula of the twin (dual) cannula assembly of the instrument.

Another object of the present invention is to provide a novel system for removing both subcutaneous and visceral fat deposits in a minimally invasive manner.

A further object of the present invention is to provide a novel method of minimally invasive visceral fat aspiration which is equally applicable to both subcutaneous and visceral fat deposits.

Yet a further object of the present invention is to provide a novel method of a lowering of the waist-to-hips circumference ratio, a treatment for and amelioration of type II diabetes mellitus, effect a favorable effect on metabolism as may be comprised of an increased insulin sensititivity, lowered fasting blood sugar, a lowering of blood pressure (particularly diastolic), an improvement in the lipid profile (lowered cholesterol, raising HDL, lowered triglycerides, lowered serum adipocytokine (Leptin) and inflammatory markers (TNF-α=tumor necrosis factor, resitin, IL-6 and IL-9), and by doing so effect a decrease in insulin resistance and reduce the risk of coronary artery disease associated with metabolic syndrome.

Another object of the present invention is to provide a method of treating type II diabetes by way of selected removal of visceral fat cells and components contained therein (e.g. fat, adipocytokine (Leptin) and inflammatory markers (TNF-α=tumor necrosis factor, resitin, IL-6 and IL-9), to improve the sensitivity of tissue cells to insulin.

Another object of the present invention is to provide a powered visceral fat aspiration instrument employing a twin (dual) cannula assembly, having a moving aspiration aperture that reciprocates over a range of about ¼" to about 1" which is appropriate to the thickness of mesenteries and omental fat deposits.

Another object of the present invention is to provide a powered visceral fat aspiration instrument employing a twin-cannula assembly supporting bipolar electro-cauterization of targeted visceral fat target being aspirated through the reciprocating inner aspiration aperture, in a safe and effective manner.

Another object of the present invention is to provide a powered visceral fat aspiration instrument employing a twin-cannula assembly which is driven is such as manner to substantially reduce vibration or disturbances which might be caused by the positioning of the instrument and thus its associated vacuum tubing, when repositioning of the aspirating cannula within visceral fat tissue.

Another object of the present invention is to provide a powered visceral fat aspiration instrument having a small size and footprint thereby facilitating its use in a laparascopic procedure where multiple viewing and retracting instruments are inserted into key hole incisions in the patient abdomen and the added bulk would be detrimental and impede adoption.

Another object of the present invention is to provide a powered visceral fat aspiration instrument employing a twin-cannula assembly which supports simultaneous fluid irrigation and visceral fat aspiration about the moving aspiration aperture, in order to achieve a sump affect facilitating aspiration through the twin-cannula assembly.

Another object of the present invention is to provide a powered visceral fat aspiration instrument employing a twin-cannula assembly during a laparascopic visceral fat aspiration procedure, which prevents the escape of compressed carbon dioxide (used to distend the patient's abdomen during the procedure) through the instrument, or its cannula assembly, or through the incision through which it is placed, other than through the inner cannula itself as a result of fat aspiration through the inner cannula aperture(s).

Another object of the present invention is to provide a coaxially-driven visceral fat aspiration instrument employing a twin-cannula assembly that performs visceral fat aspiration operations in a mechanically assisted manner.

Another object of the present invention to provide a visceral fat aspiration instrument system which comprises a hand-supportable fat aspiration instrument having a hand-supportable housing with a stationary tubing connector provided at the rear of the housing and receiving a length of flexible tubing connected to a vacuum source, and including a twin-cannula assembly coupled to a cannula drive mechanism disposed within the hand-supportable housing and powered by an external power source (e.g. electrical power signals, pressurized air-streams, etc) so as to periodically exert forces on the cannula base portion along the longitudinal axis of the the cannula assembly (i.e. coaxially exerted on the cannula base portion) and cause the hollow inner cannula base portion to reciprocate within the cylindrical (inner cannula base portion) guide tube, while tissue is being aspirated along the cannula lumen, through the lumen formed in the cannula base portion, through the cylindrical guide tube and through the stationary tubing connector, along the flexible tubing towards the vacuum source.

Another object of the present invention is to provide a visceral fat aspiration instrument system which comprises a hand-supportable fat aspiration instrument and a single-type cannula assembly, wherein the hand-supportable fat aspiration instrument includes (i) a hand-supportable housing having (i) a front portion and a rear portion aligned along a longitudinal axis, (ii) an interior volume and a cylindrical guide tube mounted within the interior volume, (iii) a cannula drive mechanism disposed adjacent the cylindrical guide tube, and (iv) a stationary tubing connector coaxially mounted to the rear portion of the hand-supportable housing along the longitudinal axis, connected to the cylindrical guide tube, and having an exterior connector portion permitting a section of flexible aspiration tubing to be connected at its first end to the exterior connector portion, and where the second end of the section of flexible tubing is connected to a vacuum source.

Another object of the present invention is to provide a visceral fat aspiration instrument system which comprises a hand-supportable fat aspiration instrument and a twin-type cannula assembly.

An even further object of the present invention is to provide such a fat aspiration instrument which can be driven by pressurized air or electricity.

A further object of the present invention is to provide such a visceral fat aspiration instrument, in which the cannula assembly is disposable.

An even further object of the present invention is to provide an improved method of performing visceral fat aspiration, in which one of the cannulas of the cannula assembly is automatically reciprocated back and forth relative to the hand-holdable housing, to permit increased control over the area of subcutaneous tissue where fatty and other soft tissue is to be aspirated.

Another object of the present invention is to provide a power-assisted visceral fat aspiration instrument, with a means along the cannula assembly to effect hemostasis during visceral fat aspiration procedures and the like, using RF-based electro cauterization.

Another object of the present invention is to provide an air-powered tissue-aspiration (e.g., visceral fat aspiration) instrument system, wherein the powered visceral fat aspiration instrument has an inner cannula that is automatically reciprocated within a stationary outer cannula by electronically controlling the flow of pressurized air streams within a dual-port pressurized air cylinder supported within the hand-supportable housing of the instrument.

Another object of the present invention is to provide such an air-powered visceral fat aspiration instrument system, wherein digital electronic control signals are generated within an instrument controller unit and these control signals are used to generate a pair of pressurized air streams within the instrument controller which are then supplied to opposite ends of the dual-port pressurized air cylinder within the powered visceral fat aspiration instrument.

Another object of the present invention is to provide such an air-powered visceral fat aspiration instrument system, wherein the rear end of the powered visceral fat aspiration instrument has a pressurized air-power supply-line connector, and an electrical control signal connector.

Another object of the present invention is to provide such an air-powered visceral fat aspiration instrument system, wherein the hollow inner cannula base portion of cannula assembly inserts into a front accessible port in the hand-supportable housing, while the aspiration tubing is connected to the stationary tube connector provided at the rear portion of the hand-supportable housing.

Another object of the present invention is to provide such an air-powered tissue-aspiration instrument system, wherein an intelligent instrument controller is used to supply air-power to the inner cannula reciprocation mechanism within the hand-supportable instrument, while communicating control signals between the instrument and its intelligent controller.

Another object of the present invention is to provide such an tissue-aspiration instrument system with an alternative electro-cauterizing dual cannula assembly, wherein a stream of irrigation fluid is automatically pumped from the base portion of the outer cannula to the distal portion thereof, along a micro-sized fluid conduit formed along the surface walls of the outer cannula, and released into the interior distal portion of the outer cannula through a small opening formed therein, for infiltration and irrigation of tissue during aspiration in order to facilitate pump action.

These and other objects of the present invention will be described in greater detail hereinafter in the claims to invention appended hereto.

BRIEF DESCRIPTION OF THE DRAWINGS

The above Objects of the Present Invention will be more fully understood when taken in conjunction with the following Figure Drawings, wherein like elements are indicated by like reference numbers, wherein:

FIG. 2A1 is a perspective view of the air-powered fat aspiration instrument shown in FIG. 2, having an twin-cannula assembly supporting three-functions (i.e. tumescent infusion, electro-cautery and variable-spectrum illumination) about the aspiration aperture during visceral fat aspiration operations;

FIG. 2A2 is a partially exploded diagram of the fat aspiration instrument shown in FIG. 2A1, showing its hand-supporting housing, in which its cylindrical (cannula base portion) guide tube and air-powered driven mechanism are installed, while its cannula base portion, cannula and cannula lock nut are shown disassembled outside of the hand-supportable housing;

FIG. 2C is a perspective view of the multi-function twin-cannula assembly of the present invention employed on the instrument shown in FIGS. 2A and 2A1;

FIG. 2D1 is a perspective view of the outer cannula component of the twin-cannula assembly of FIG. 2C, constructed of stainless steel tubing coated with a white-colored PFA (Dupont Teflon®) coating, and showing its integrated irrigation port and irrigation channel, and its integrated fiber-optic port and fiber-optic channel;

FIG. 2D2 is an elevated side view of the outer cannula component of the twin-cannula assembly of FIG. 2D1, showing electro-cautery contacts on the base portion of the outer cannula to which RF signal signal cables are connected;

FIG. 2D3 is a first partially cut-away perspective view of the distal (tip) portion of the outer cannula component of the twin-cannula assembly of FIGS. 2D1 and 2D2, illustrating that the fiber carrying the illumination source terminates at the outer aspiration aperture to the field of aspiration about the aspiration aperture, and irrigation enters into the bullet tip area of the outer cannula;

FIG. 2D4 is a second partially cut-away perspective view of the distal (tip) portion of the outer cannula component of the twin-cannula assembly of FIGS. 2D1 and 2D2, illustrating that the fiber carrying the illumination source terminates at the outer aspiration aperture to the field of aspiration about the aspiration aperture, and irrigation enters into the bullet tip area of the outer cannula;

FIG. 2E1 is a first perspective view of the base portion of the outer cannula component of the bipolar electro-cauterizing cannula assembly shown in FIG. 2C;

FIG. 2E2 is a second perspective view of the inner cannula base portion of the outer cannula component employed in the bipolar electro-cauterizing cannula assembly shown in FIG. 2C;

FIG. 2E3 is a plan view of the base portion of the electrically-conductive outer cannula component of the bipolar electro-cauterizing cannula assembly shown in FIG. 2C, revealing its set of radially arranged electrical contacts disposed about the central axis of the outer cannula base portion, while the inner cannula base portion is slidably received within the cylindrical guide structure within the housing, so as to enable electrical contact between the electrically-conductive inner cannula and radially-arranged electrical contacts;

FIG. 2E4 is a perspective view of the outer cannula base portion shown in FIG. 2E3;

FIG. 2E5 is an exploded view of the outer cannula base portion shown in FIGS. 2E1 through 2E4;

FIG. 2H shows a cautery control program written in programming language, describing when to open and close the cautery relay switch employed within the electro-cautery RF power signal generation module of the system controller;

FIG. 3 is a perspective view of a second illustrative embodiment of the bipolar electro-cauterizing twin-cannula visceral fat aspiration instrumentation system of the present invention, depicted in the system of FIG. 1, and shown comprising (i) a hand-supportable fat aspiration instrument having (i) a hand-supportable housing with a stationary tubing connector provided at the rear of the housing and receiving a length of flexible tubing connected to a vacuum source and connecting to the cylindrical cannula base portion guide tube, and a twin tumescent-type cannula assembly having an inner cannula coupled to an electrically-powered cannula drive mechanism disposed within the hand-supportable housing and powered by a source of electrical power, while its stationary outer cannula is releasably connected to the front portion of the hand-supportable housing, and (ii) a system controller for controlling the electro-cautery, irrigation and illumination functions supported by the fat aspiration instrument;

FIGS. 3D1 through 3D8 show a series of exploded views of the bipolar electro-cauterizing fat aspiration instrument of the present invention, showing its components disassembled;

FIG. 3F1 is a perspective view of the back housing plate employed in the hand-supportable instrument;

FIG. 3F2 is a perspective view of the cylindrical guide tube supporting its first and second electromagnetic coils;

FIG. 3F3 is an elevated side view of the cylindrical guide tube supporting its first and second electromagnetic coils;

FIG. 3F4 is a perspective partially-cutaway view showing the connection of the two electromagnetic coils to the contact plug employed in the hand-supportable fat aspiration instrument of the present invention illustrated in FIG. 3A;

FIG. 3F5 is schematic diagram of a two coil push-pull type of circuit for enabling the cannula drive mechanism employed in the hand-supportable fat aspiration instrument of the present invention illustrated in FIG. 3A;

FIG. 3G1 is a sectional-view of a second embodiment of the hand-supportable fat aspiration instrument of FIG. 3A, showing a cylindrical (cannula base portion) guide tube supporting three electromagnetic coils used to realize the cannula drive mechanism employed in the fat aspiration instrument;

FIG. 3G2 is schematic diagram of a three coil push-pull type of circuit for enabling the cannula drive mechanism employed in the second embodiment of the hand-supportable fat aspiration instrument of the present invention illustrated in FIG. 3A;

FIG. 3I shows a cautery control program written in programming language, describing when to open and close the cautery relay switch employed within the electro-cautery RF power signal generation module;

FIG. 4 is a perspective view of the in-line fat sampling device of the present invention connected between the vacuum source and the twin-cannula visceral fat aspiration instrument of the present invention, shown in FIGS. 2A and 3A;

FIG. 4C is a first exploded view of the in-line fat sampling device of the present invention, shown comprising a collection chamber, a lid with barbed connector for connection to the suction tubing, a suction plate having six projections for supporting six sample syringes, a selector with a passage from center to periphery to control flow of aspirated fat sample into the selected syringe, and a barbed connector for connecting to tubing extending to the hand-supportable fat aspiration instrument, and a spring pushing up the turning knob and keeping the selector at the bottom of the collection chamber;

FIG. 4F1 is a cross-sectional view of the in-line fat sampling device of the present invention shown in FIGS. 4A through 4E, illustrating the passage within the selector component, extending from the center of the device to the periphery thereof to control the flow of aspirated fat samples into the selected syringe;

FIG. 4F2 is a cross-sectional view of the in-line fat sampling device shown in 4F1, illustrating the flow of an aspirated fat sample from the patient, through the fat aspiration instrument of the present invention, to the selector component of the fat sampling device, through the passageway/flow director, into the selected syringe, whereupon fat cells are collected within the selected syringe while excess fluid is expressed through holes in the selected syringe, and passed out through the barded connector towards to vacuum source;

FIG. 4G is a graphical representation illustrating the process of removing collected visceral fat samples contained in syringes from the collection container of the in-line fat sampling device of the present invention;

FIG. 4H is a perspective view of a syringe removed from the collection container of the in-line fat sampling device of the present invention, and arranged in proximity with a hole excluder and syringe plunger, for use together when desiring to eject a visceral fat sample collected in a selected syringe within collection container of the in-line fat sampling device of the present invention;

FIGS. 4I1 and 4I2 set forth a graphical representation illustrating the process of using the hole exclude and syringe plunger to eject a visceral fat sample that has been collected in a syringe removed from the collection container of the in-line fat sampling device of the present invention;

DETAILED DESCRIPTION OF THE ILLUSTRATIVE EMBODIMENTS OF THE PRESENT INVENTION

Figure 1:
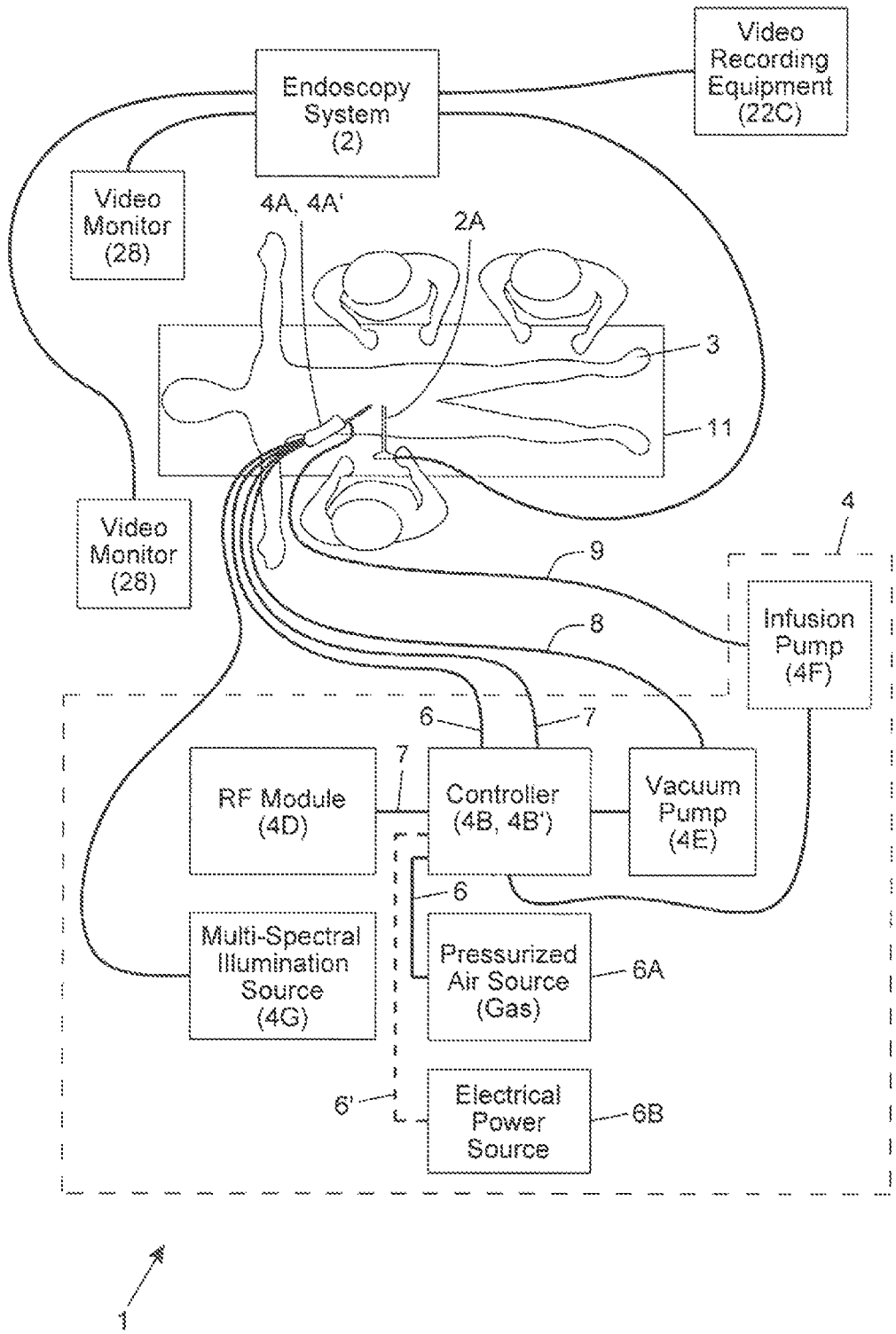
FIG. 1 is a system block diagram of the laparoscopically-guided bipolar power-assisted twin-cannula visceral fat aspiration system of the present invention, showing an obese patient in an operating room undergoing a mesenteric visceral fat aspiration procedure carried out using the same in accordance with the principles of the present invention.

Referring to the figures in the accompanying Drawings, the various illustrative embodiments of the present invention will be described in great detail, wherein like elements will be indicated using like reference numerals.

Overview on Methods of Treatment According to Principles of the Present Invention In general, the method of treatment according to the present invention involves performing vacuum-assisted aspiration of mesenteric fat from a patient in the intra-abdominal region, using either an "open direct-viewing" based laparotomy procedure, or preferably, a minimally-invasive, "laparoscopic" based procedure using the new and improved fat aspiration instruments of the present invention.

The open direct-viewing based procedure involves a surgical team making a direct laparotomy incision into the abdomen of the patient using their own direct human vision to guide their surgical instruments, while performing a visceral fat aspiration procedure/method in accordance with the principles of the present invention.

The laparoscopic-based procedure involves a surgical team making one or more limited access portals into the patient's abdomen and using laparoscopic and/or camera monitor assistance for their human vision, while performing the visceral fat aspiration procedure/method in a minimally invasive fashion according to the principles of the present invention.

Using either method, visceral fat is safely removed from the mesenteric region of a patient to help to ameliorate the metabolic syndrome, abdominal obesity and/or type II diabetes.

Specification of the Laparoscopically-Guided Intra-Abdominal Visceral Fat Aspiration Instrument System of the Present Invention, Designed for Safely Removing Visceral Fat from the Mesenteric Region of a Patient In FIG. 1A, there is shown a preferred laparoscopically-guided intra-abdominal visceral fat aspiration instrument system 1 for performing the mesenteric visceral fat aspiration methods of the present invention, typically in an operating room environment. The system 1 comprises: an endoscopy (e.g. laparoscopy) subsystem, or laparoscope 2 having (i) a video probe 2A provided with an embedded 2D high-resolution digital color image sensor with a field of view (FOV) for insertion into the abdomen of the patient 3, (ii) one or more video monitors (e.g. LCD displays and controller) 2B for displaying to surgeons and assistants, real-time digital color video images of the patient's abdominal region captured along the field of view (FOV) of the video probe 2A, and (iii) digital recording equipment 2C for recording captured digital video during the operation and marking the same by the surgeons, as required; a bipolar electro-cauterizing twin-cannula powered visceral fat aspiration system 4 having (i) a powered hand-supportable fat aspiration instrument 4A provided with a self-irrigating, bipolar electro-cauterizing and fiber-illuminating twin-cannula assembly 5, (ii) a system controller 4B connected to the hand-supportable instrument 4A by way of a flexible multi-lumen cable assembly 4C, for supplying (i) pressurized air streams 6 from pressurized gas source 6A to drive the inner cannula of the hand-supportable instrument 4A (shown in FIGS. 2A through 2H), or (ii) electrical power signals 6' from electrical power source 6B to drive hand-supportable instrument 4A' (shown in FIGS. 3 through 3I), and optionally (iii) RF-power signals 7 generated by an RF signal generating module 4D for powering the self-irrigating bipolar electro-cauterizing and illuminating twin cannula assembly 5, as taught in U.S. Pat. No. 7,384,417 B2; a vacuum pump 4E operably connected to the inner cannula via a flexible tubing and other components, for aspirating visceral fat through the aspiration aperture 9 of the twin cannula assembly 5 during system operation; an infusion pump 4F controlled by the system controller 4B, for periodically or continuously pumping irrigation fluid through irrigation tube 12 and into an irrigation port on the cannula assembly for infusing solution near the distal portion of the cannula assembly 5 during system operation; an operating table 11 for supporting a patient; a multi-spectral illumination source 4G providing the surgeon with selectable spectrum control, to deliver a desired spectrum of illumination along an optical fiber 12 to the outer cannula and produce a field of illumination spatially-overlapping the field of aspiration about the reciprocating inner aspiration aperture 9 at the distal portion of the twin-cannula assembly 9; in-line fat sampling device 14 installed in-line along the flexible tubing 9A, 9B, for collecting and indexing samples of visceral fat while the surgeon samples the abdomial region of the patient, for subsequent analysis and testing/measurment for compounds indicative of obesity, metabolic syndrome and/or type II diabetes; and other operating room equipment including high intensity lighting apparatus, retraction clips, stitches etc.

In addition, the laparoscopically-guided visceral fat aspiration system 1 of the present invention further includes instruments such as trochars for penetrating the abdomen, laparoscopic graspers, laparoscopic scissors, and a CO2 infusion tube (supplied from CO2 gas source 6A), as described in detail in U.S. Pat. No. 7,384,417 B2, incorporated herein by reference.

Typically, infusion pump 4F will include a roller pump which compresses the tubing to create forward flow, as disclosed in U.S. Pat. No. 7,384,417 B2 incorporated herein by reference. The infusion pump 4F supplies a pulsatile flow of irrigation fluid through the distal tip portion of the twin-cannula assembly of the present invention, as shown in FIGS. 2D3 and 2D4, so that controlled amounts of fluid are delivered under short periods of time to facilitate synchronization with either the forward or return stroke of the inner cannula 5B. This feature will be described in great detail hereinafter.

In the illustrative embodiment of the present invention, the multi-spectral illumination source 4G can be constructed from a white light source producing a white light beam that is filtered by a selectable color filter wheel, with associated optics, interfaced with a fiber-optic delivery cable, to provide the surgeon with selectable spectrum control, to deliver a desired spectrum of illumination (e.g. red, blue and/or yellow) at and about the aspiration aperture of the fat aspiration instrument 4A. Alternatively, the illumination source 4G can be realized using a multi-spectral LED array with associated optics, interfaced with a fiber-optic delivery cable, to provide the surgeon with selectable spectrum control, to deliver a desired spectrum of illumination (e.g. red, blue and/or yellow) at and about the aspiration aperture of the fat aspiration instrument 4A. The multi-spectral illumination source 4G can also be adapted to generate and deliver a bright red light beam at the time of, and at the location of visceral fat aspiration about the distal portion of the twin-cannula assembly 5. Also, in addition to white-type light being supplied by the laparoscopic light source during operations, the multi-spectral illumination source 4G can supply red/blue/yellow light (i.e. illumination) through the fiber-optic channel along the twin-cannula assembly, to illuminate tissue about the aspiration aperture, to help visually distinguish and accentuate arterial vessels, veins and fat itself, and facilitate visculation of arterial blood vessels, portal and systemic veins, and fat. In yet alternative embodiments, the color wheel may be rotated continuously, offering a 3-D emphasis of the treatment area.

In FIGS. 2A through 2G, a hand-supportable multi-function visceral fat aspiration instrument 4A is shown for use with system 1 depicted in FIG. 1A. This embodiment of the instrument of the present invention is powered by a source of pressured air or gas (e.g. a pressurized-air cylinder driven by source of pressurized gas (e.g. $CO_2$)). In FIGS. 3A through 3J, an alternative embodiment of the hand-supportable multi-function visceral fat aspiration instrument 4A' is shown for use with system 1 depicted in FIG. 1A. This alternative embodiment of the instrument is powered by an electromagnetic motor driven by electrical current delivered through coil windings at a given voltage. Both instruments 4A and 4A' employ the multi-function twin-cannula assembly 5 of the present invention shown in FIGS. 2C through 2D4, and supporting its multiple functions, namely: bipolar electro-cauterization, fluid irrigation, and spectrum-controlled illumination at and about the reciprocating aspiration aperture 9 of the twin-cannula assembly.

Figure 2:
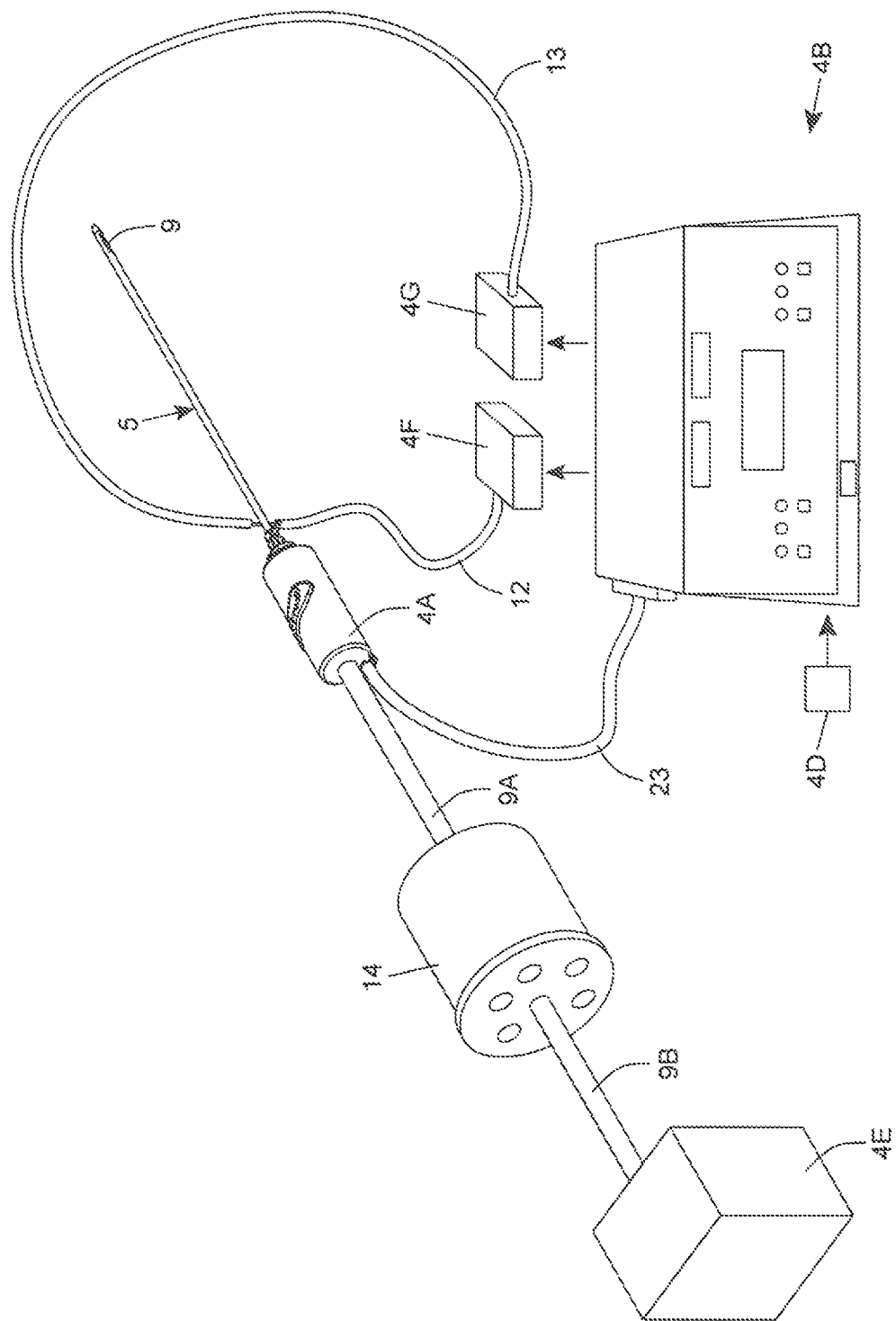
FIG. 2 is a perspective view of a first illustrative embodiment of the bipolar electro-cauterizing twin-cannula visceral fat aspiration instrumentation system of the present invention, depicted in the system of FIG. 1, and shown comprising (i) a hand-supportable fat aspiration instrument having (i) a hand-supportable housing with a stationary tubing connector provided at the rear of the housing and receiving a length of flexible tubing connected to a vacuum source and connecting to the cylindrical cannula base portion guide tube, and a twin tumescent-type cannula assembly having an inner cannula coupled to an pneumatically-powered cannula drive mechanism disposed within the hand-supportable housing and powered by a source of pressurized air or other gas, while its stationary outer cannula is releasably connected to the front portion of the hand-supportable housing, and (ii) a system controller for controlling the electro-cautery, irrigation and illumination functions supported by the fat aspiration instrument.
Figure 3:
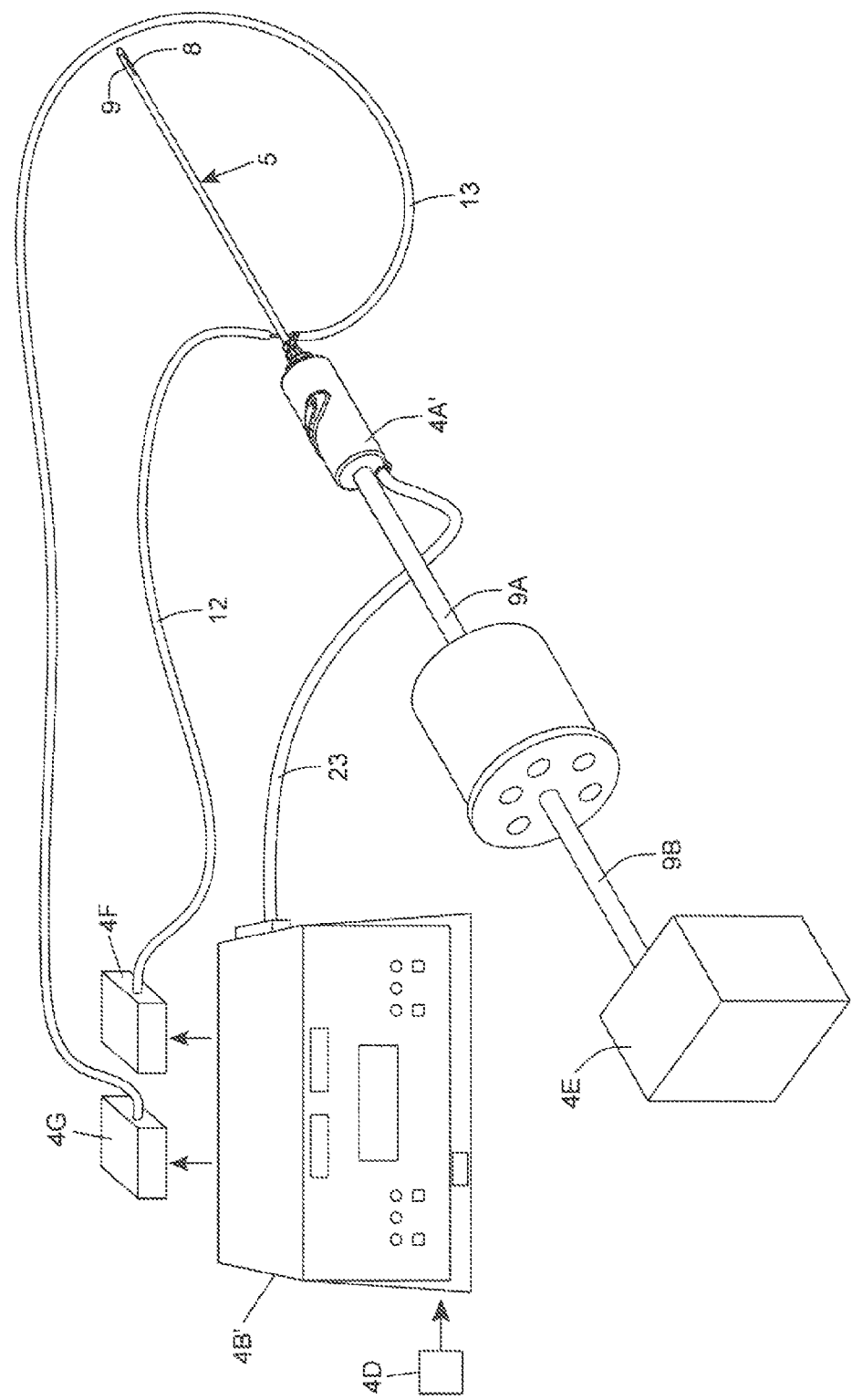

In FIGS. 4 through 4I2, an in-line visceral fat sampling device 14 for use with the fat aspiration instruments of the present invention, is described in technical detail. This in-line fat sampling device allows the surgeon to easily collect and index samples of visceral fat aspirated in particular regions of the patient's abdominal cavity, for subsequent analysis that may be informative during subsequent serial fat aspiration procedures during a particular course of treatment.

It is appropriate at this junction, to now describe in greater detail the coaxially-driven multi-function visceral fat aspiration instruments 4A and 4B of the present invention.

Specification of the First Illustrative Embodiment of the Twin-Cannula Multi-Function Co-Axially Driven Visceral Fat Aspiration Instrument of the Present Invention In FIG. 2A, the first illustrative embodiment of the twin-cannula visceral fat aspiration instrumentation system 1 is shown comprising: a hand-supportable fat aspiration instrument 4A having (i) a hand-supportable housing 15 with a stationary tubing connector 16 provided at the rear of the housing and receiving a length of flexible tubing 9A connected to a vacuum source 4E and connecting to the cylindrical cannula base portion guide tube 20, and (ii) a multi-function twin-cannula assembly 5 having an inner cannula 5B with a inner cannula base portion 20 disposed within the cylindrical cannula base portion guide tube 21, and coupled to an pneumatically-powered cannula drive mechanism (as illustrated in FIG. 2A2) housed within the hand-supportable housing and powered by a source of pressurized air or other gas, while its stationary outer cannula 5A is releasably connected to the front portion of the hand-supportable housing 14; system controller 4B for controlling the electro-cautery, irrigation and illumination functions supported by the fat aspiration instrument; an aspiration source 4E; a pneumatic power source 6A; and a flexible multi-core cable assembly 20 connecting the system controller 4B and the hand-supportable instrument 4A; and an infusion pump 4F for supplying irrigation fluid to an infusion port 35 on the outer cannula via flexible tubing, and connected to the system controller 4B for sychronized pulse control, and operational to synchronize the release of irrigation fluid (i.e. infusion) with inner cannula motion.

As shown in FIG. 2A, the air-powered fat aspiration instrument 4A comprises a single-button quick connect plug 22 provided on the rear portion of the hand-supportable housing, for connecting the multi-core cable assembly 23 and supporting two gas lines and three electric wires between the instrument and the system controller in a single bundle, as taught in U.S. Pat. No. 7,381,206 to Cucin, incorporated herein by reference, with appropriate modifications for the application at hand. While RF power signals can also be supplied through the multi-core cable assembly, and routed as necessary to the cautery leads 30A and 30B provided on the outer cannula base portion, as shown in FIGS. 2A and 2A1, RF power signals can be supplied through power cables 31 that are separate from the multi-core cable assembly 23.

Figure 2B:
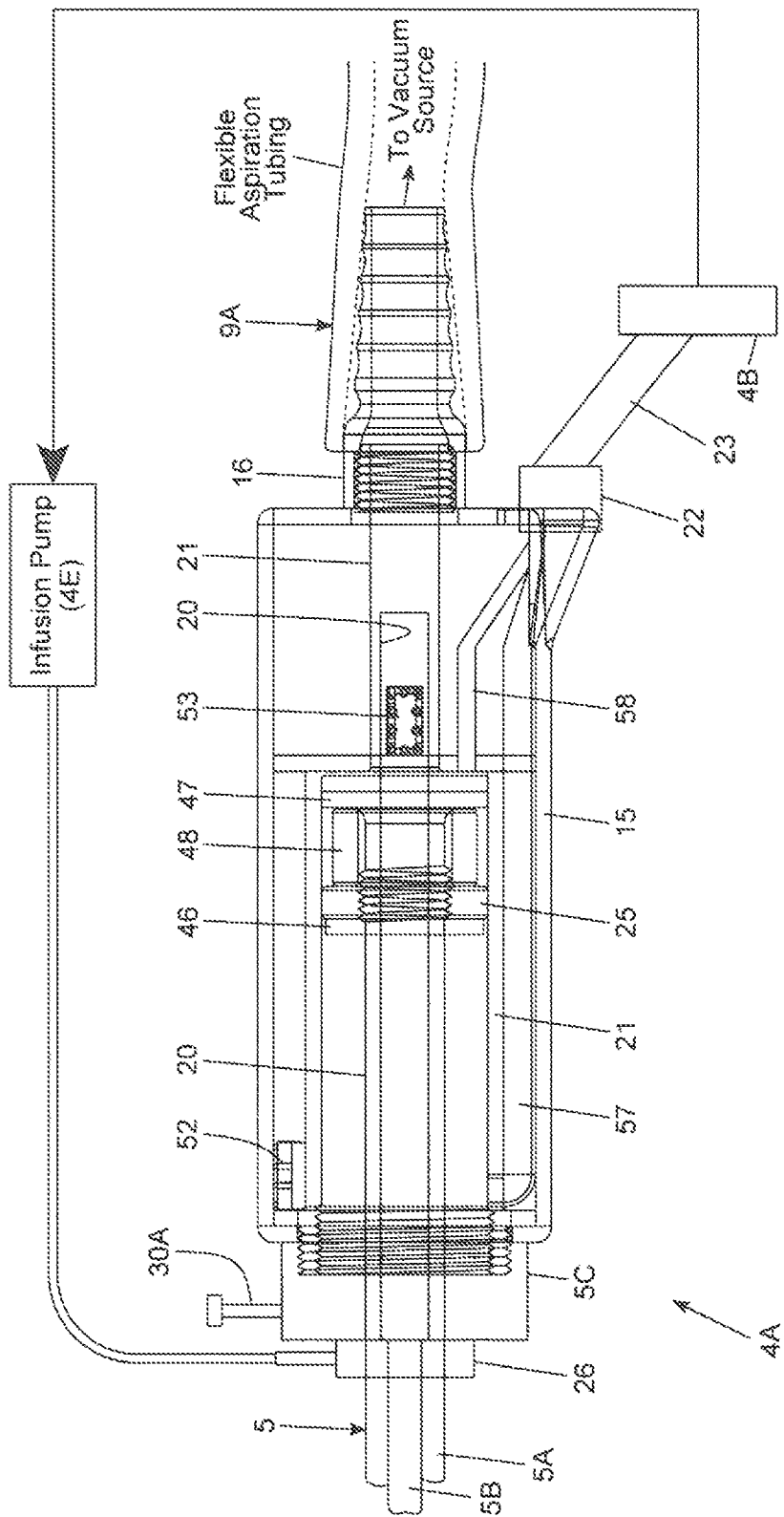
FIG. 2B is a cross-sectional view of the hand-supportable fat aspiration instrument shown in FIG. 2A1.

As shown in FIGS. 2B and 2C, the twin-cannula assembly 5 comprises an inner cannula component 5B that is slidably received within an outer cannula component 5A. The inner cannula component 5B has a distal end and a proximal end and an inner aspiration aperture 8, and is provided with a Leur-lock fitting 25 at its proximal end so as to be able to connect to a matched fitting provided on the inner cannula base portion 20 which reciprocates within the cylindrical cannula base portion guide tube 21, mounted within the hand-supportable housing 15. The outer cannula component 5A also has a distal end and a proximal end and an elongated outer aspiration aperture 9, and is provided with a Leur-lock fitting 26 at its proximal end so as to be able to connect to a matched fitting provided on the outer cannula base portion 5C which connects to the front portion of the housing 15 by way of a threaded hole formed therein as shown in FIG. 2A2. The inner and outer cannulas are keyed to ensure that the inner aspiration aperture 8 is always in registration (i.e. cannot rotate within the outer cannula, and remains in constant alignment) with the elongated aspiration aperture (i.e. slot) during instrument operation.

The outer cannula component 5A is shown detailed in FIGS. 2D1 through 2D4, the outer cannula base portion 5C is detailed in FIGS. 2E1 through 2E5, and the inner cannula component 5B is detailed in FIGS. 2A2 and 2B. When fully assembled, and configured with its hand-supportable instrument housing, and the other components of the system 1, the twin-cannula assembly 5 of the present invention simultaneously performs a number of important functions during visceral fat aspiration operations, namely: tumescent infusion of an irrigation fluid, electro-cauterization of aspirated fat passing through the inner aspiration aperture 9, and variable-spectrum fiber-illumination delivered across the field of irrigation, about the outer aspiration aperture 9. These functions will be described in greater detail hereinafter.

As shown in FIGS. 2D1 and 2D2, the outer cannula component 5A is realized as a thin tube made from stainless steel tubing (No. 304) and then coated with a white-colored PFA (Dupont Teflon®) coating. Also, the inner cannula component 5B is realized as a thin tube (of slightly smaller outer diameter dimensions than the outer cannula) made from stainless steel tubing (No. 304) and then coated with a black-colored PFA (Dupont Teflon®) coating. These high contrast coatings will serve to render the moving "white" (reflective and bright) inner cannula aspiration aperture 9 highly visible against the "black" (absorptive and dark) outer cannula, in digital video images captured, buffered and displayed (in real-time) during video-guided fat aspiration operations carried out in accordance with the principles of the present invention. While PFA coatings are applied over the outer surfaces of the inner and outer cannulas, PFA coating material should be removed from the peripheral edges of the outer cannula aspiration aperture 8 and the inner cannula aspiration aperture 9 where electrical field potentials are to be generated during bipolar electro-cauterization operations about the relatively moving outer aspiration apertures. Also, PFA coating material should be removed from the outer surface of the proximal portion of the inner cannula so that electrical contact can be established between the radially extending contacts (brushes) 30 supported within the non-conducting outer cannula base portion 5C, shown in FIGS. 2E2 and 2E3, and electrically connected to the bipolar RF signal supply port 30A provided on the exterior of the outer cannula base portion 5C.

As shown in FIGS. 2D1 through 2D4, an irrigation supply port 31 is provided on the proximal end of the outer cannula before its Leur-lock fitting, and an irrigation channel 32 is formed along the wall of the outer cannula component (via longitudinal brazing) and terminates at an irrigation release port 33 located at the distal tip portion of the cannula, for suppling irrigation fluid on the inside of the bullet-shaped distal portion of the outer cannula, adjacent its outer aspiration aperture/slot 8, as clearly shown in FIGS. 2D3 and 2D4, to provide continuity with the interior of the outer cannula at the tip to maximize sump effects and directed irrigation.

By delivering the irrigation fluid into the very tip of the inside region of outer cannula the following benefits are achieved: (1) maximal sump effect to help aspiration of fat; and (2) hydrostatic dissection every time the inner cannula advances and push the irrigation solution that has collected inside the outer cannula between the back-stroked inner cannula and the dome of the outer cannula into the tissues (mesentery) to facilitate dissection. Tumescent solution may be employed, e.g. lactated Ringers and a very dilute solution of epinephrine may be employed to minimize bleeding.

On the opposite side of the outer cannula component, a fiber optic supply port 35 is integrated fiber-optic port is provided on the proximal end of the outer cannula before its Leur-lock fitting 30B, and an fiber optic channel 36 is formed along the wall of the outer cannula component (via longitudinal brazing) and terminates at an illumination port 37 located at the distal tip portion of the cannula. An optical fiber 38 is installed through the fiber optic supply port 35 and along the fiber channel 36, and provided with a conventional fiber optic cable connector at the fiber optic supply port 35, so as to supply an illumination signal that is delivered to the illumination port 37 to illuminate tissue in the region outer aspiration aperture 8 of the outer cannula 5A during fat imaging and aspiration operations. Notably, the end of the optical fiber will be shaped appropriately at the illumination port 37 to provide a field of illumination that spatially overlaps the field of aspiration about the outer aspiration aperture, to ensure that tissue within and about the field of aspiration is optimally illuminated while digital video images of the distal portion of the twin-cannula assembly 5 are being captured, buffered and display on video display units mounted in the operating room, for the surgeon to view and use while manually guiding the distal portion of the cannula within the patient's abdominal region during surgery, to remove visceral fat in the patient's mesentery region.

In order to supply bipolar RF signals to the electrically conductive inner and outer cannula component of the twin-cannula assembly of FIG. 2D1, the non-conductive outer cannula base portion 5C is provided with first RF power signal port 30A to which a first RF signal cable is connected in a conventional manner, whereas the electrically conductive outer cannula is provided with second RF power signal port 30B to which a second RF signal cable is connected in a conventional manner A first electrical connection is established between the RF power signal port 30B and the electrically-conductive outer cannula tubing 5B, which may be realize using electrical wiring and soldering in a manner known in the art, or other techniques known in the art. Also, a second electrical connection is established between the RF power signal port 30A and the array of radially-projecting electrical contacts (i.e. brushes) 30 mounted within the inside bore of the outer cannula base portion 5C, as shown in FIG. 2E4 and 2E5. The second electrical connection may also be realized using electrical wiring and soldering in a manner known in the art, but other techniques may be used as well.

During twin-cannula operation, the set of radially arranged electrical contacts 30 establish low-friction electrical contact with the exposed non-coated portion of the outer surface of the electrically conductive inner cannula 5B. With this arrangement, a first polarity of the supplied RF power signal is conducted to the electrode region 32B formed about the peripheral edge of the inner cannula aspiration aperture 8, while the second polarity of the RF power signal is conducted to the electrode region 32A formed about the peripheral edge of the outer cannula aspiration aperture 5A, to thereby provide bipolar electro-cauterization about the moving inner aspiration aperture, within the fields of aspiration, irrigation and illumination.

As shown in FIG. 2A2, the reciprocating inner cannula 5B has luer lock fitting 25 to mate to luer lock fitting 25' on the inner cannula base portion 20; magnet 48 is affixed to inner cannula base portion 20 using a screw-on nut 45; front and rear gas tubes 57 and 58 run to from the front of the housing to the rear multi-core quick connect plug 22; the quick connect multi-core plug 22 connects to multi-core cable containing two fluidic (gas) channels and at least three low voltage electrical circuits; the cable 23 runs to controller 4B within which the gas channels directly attached to the compressed gas source (not shown); the front and rear Hall sensors 22 and 23 are provided within the hand-supportable housing, for detecting the excursion of the cannula base portion 20 within the cylindrical guide tube 1; front and rear flat sealing washers 46 and 47 are provided for slidably supporting the inner cannula base portion 20 along the cylindrical guide tube 21; threaded chamber cover 10 is provided with a hole, through which the inner cannula 5B protrudes; sufficiently large through-and-through vents are formed in the threaded chamber cover 10 to allow any gas that leaks past the front washer 46, to exit the chamber. Such air venting to the ambient is less critical because the concentric tube-with-a-tube structure, and the sliding of the cannula base portion 20 inside the rear tubing connector assembly, provides effective seals in and of themselves. Also, in this embodiment, the walls of at least the front (pneumatic) chamber portion of housing should be made from a non-magnetizable metal (e.g. SS 304) or other material that will support the necessary gas pressure of actuation (e.g. ~100 PSI).

During instrument operation, the Hall effect sensors 52 and 53 sense the position of the inner cannula base portion 20 within cylindrical guide tube 21 by sensing the magnetic field of its magnetic ring 8. As the inner cannula base portion 20 reciprocates within the cylindrical guide tube 21, the aspiration/vacuum tubing 9A connected to the barb connector 16 on the stationary tubing connector, remains stationary and thereby preventing any jerking action on the surgeon's hands and reducing image jitter during video image capture and display operations. Also, the inner and outer cannulas 5A, 5B are provided with luer-lock fittings 25, 26 respectively, while the inner cannula base portion 20 is typically realized or provided as a sterile single-use disposable item, made from plastic or metal, and having a low cost magnet and silicone washers to provide fluid seals between the inner cannula base portion 20 and the cylindrical guide tube 21 within the hand-supportable housing 15.

Figure 2F:
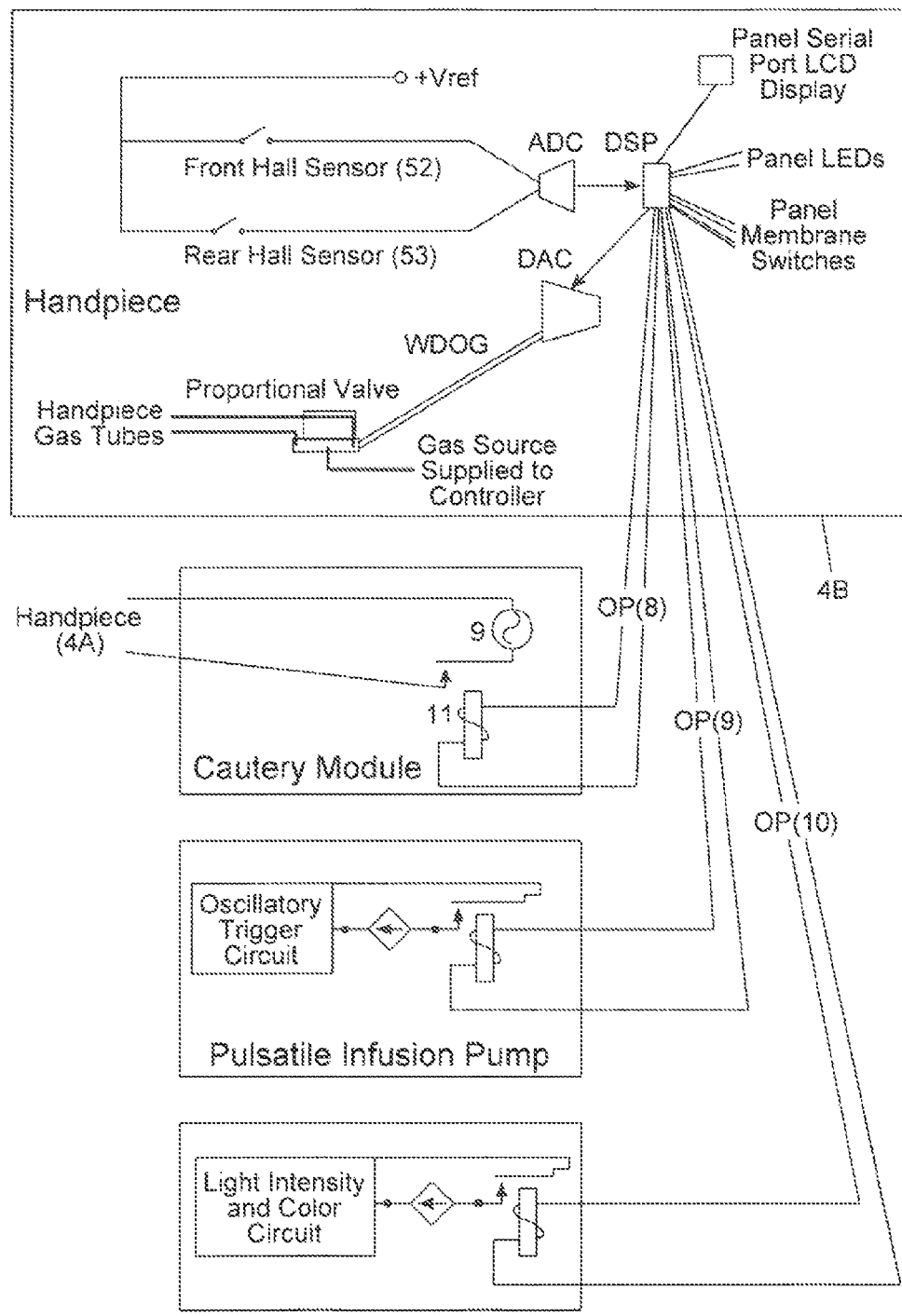
FIG. 2F is a schematic diagram for the system controller employed by the first illustrative embodiment of the fat aspiration instrumentation system of FIG. 2A, supporting electro-cauterizing, irrigation and illuminating functions about the outer aspiration aperture of the fat aspiration instrument.

In FIG. 2F, the system controller 4B is shown comprising a number of components, namely: an analog-to-digital converter (ADC) receiving signals generated by the front and rear Hall-effect cannula base position sensors installed within the hand-supportable housing of the instrument; a LCD panel; communication ports; LED indicators; and panel membrane switches supported on the controller console housing; digital signal processor (DSP); and a digital-to-analog converter (DAC) and proportional valve contained within the controller console housing, and supplying gas tubes (via the multi-core cable assembly); and ports for receiving a supply of pressurized gas, for controlled supply to the inner cannula drive mechanism of this embodiment of the present invention. For further details on constructing a system controller, such as system controller 4B, reference should be made to U.S. Pat. No. 7,381,206 to Cucin, incorporated herein by reference.

Figure 2G:
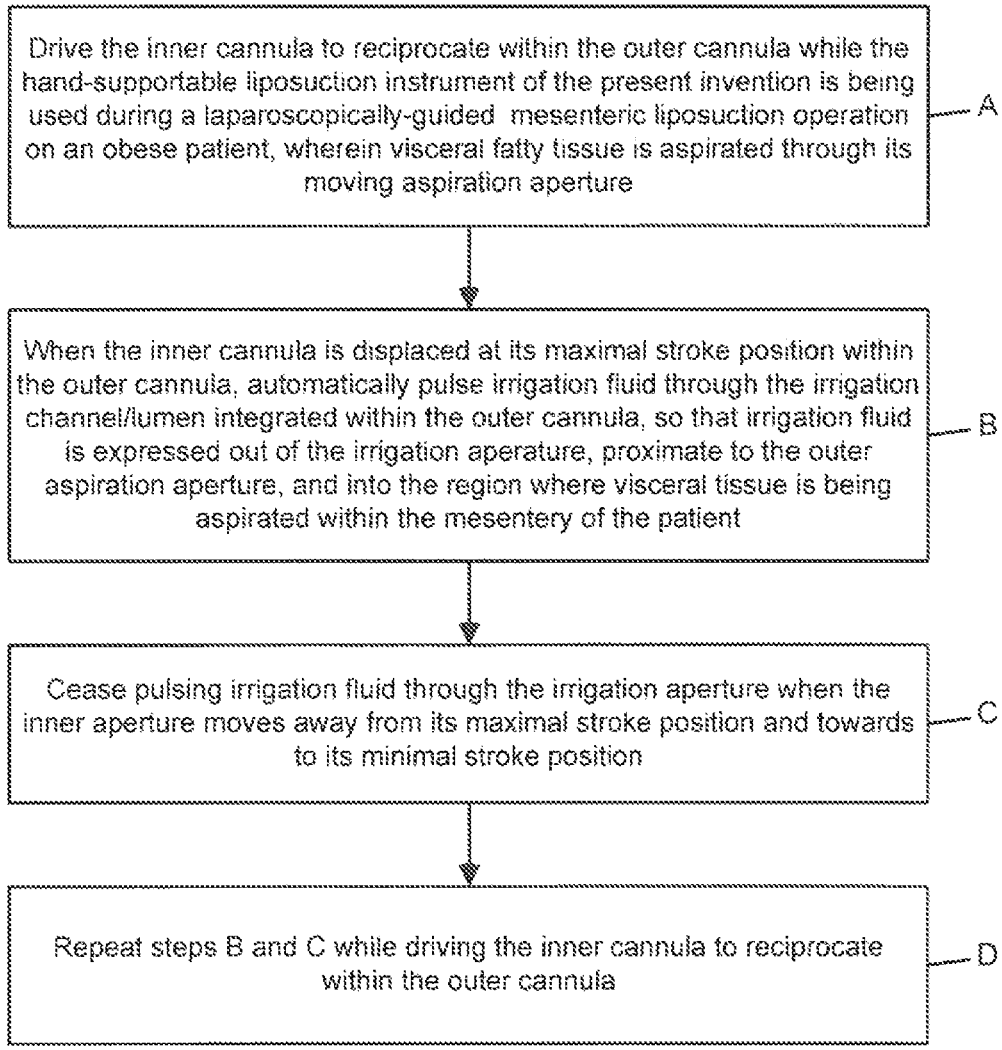
FIG. 2G is a flow chart describing the operation of the infusion pump of FIG. 2A in cooperation with irrigating electro-cauterizing visceral fat aspiration instrument illustrated in FIGS. 2A through 2F.

The flow chart of FIG. 2G describes the operation of the infusion pump 4F in cooperation with irrigating electro-cauterizing visceral fat aspiration instrument illustrated in FIGS. 2A through 2E. The cautery control program written set forth in FIG. 2H describes when to open and close the cautery relay switch employed within the electro-cautery RF power signal generation module of the system controller. Such control operations are carried out by the DSP in the system controller. A control program is also provided within the DSP for activating the illumination source when the twin-cannula assembly is being driven by its integrated pneumatic motor.

During system operation, the inner cannula base portion 20 reciprocates within the cylindrical guide tube 21, while the aspiration/vacuum tubing 9A connected to the barb connector 16 on the stationary tubing connector, remains stationary and thereby preventing jerking action on the surgeon's hands and reducing image jitter and blurring during video capture and display operations during surgery. Also, the infusion pump 4F delivers controlled amounts of fluid through the irrigation channel 32 and out the irrigation port 33, over short periods of time, in synchronization with either the forward or return stroke of the inner cannula 5B within the outer cannula 5A. Such irrigation faciliates fluid flows out of the irrigation aperture 33 and proximate to the elongated aperture 8, while visceral fat is being electro-cauterized by electrodes 32A, 32B and aspirated through the reciprocating aspiration aperture 9 of the hand-supportable visceral fat aspiration instrument. At the same time, the fiber optic supply port 35 and fiber delivery channel 36 illuminates tissue within the field of aspiration, while a high resolution digital imager 2A with a field of view (FOV) on the distal portion of the twin-cannula assembly captures high contrast images of the white (reflective) and black (absorptive) colored PFA-coatings on the outer and inner cannulas 5A and 5B respectively, to assist the surgeon in practicing the method of the present invention.

FIG. 2C describes the primary control operations performed by system controller 4B during fluid irrigation delivery operations using the surgical system of FIG. 1. Specifically, as indicated at Step A in FIG. 2C, the inner cannula 5B is driven to reciprocate within the outer cannula 5A while the hand-supportable visceral fat aspiration instrument is being used during a laparoscopically-guided mesenteric visceral fat aspiration operation on an obese patient, wherein visceral fatty tissue is aspirated through its moving aspiration aperture. As indicated at Step B, when the inner cannula is displaced at its maximal stroke position within the outer cannula, irrigation fluid is automatically pulsed through the irrigation channel/lumen integrated within the outer cannula, so that irrigation fluid is expressed out of the irrigation aperture, proximate to the outer aspiration aperture, and into the region where visceral tissue is being aspirated within the mesentery of the patient. As indicated at Step C, the automatic pulsing of irrigation fluid through the irrigation aperture is ceased when the inner aperture moves away from its maximal stroke position and towards its minimal stroke position. As indicated at Step D, the operations of Steps B and C are repeated while driving the inner cannula to reciprocate within the outer cannula. The control routine of FIG. 2F will be realized using computer programming techniques well known in the art.

Specification of the Second Illustrative Embodiment of the Twin-Cannula Multi-Function Co-Axially Driven Visceral Fat Aspiration Instrument of the Present Invention In FIG. 3, the second illustrative embodiment of the multi-function twin-cannula visceral fat aspiration instrument 4A' is shown for use in the system 1 of FIG. 1. As shown, this visceral fat aspiration instrument 4A' comprises: a hand-supportable housing 15 with a stationary tubing connector provided at the rear of the housing and receiving a length of flexible tubing 9 connected to vacuum source 4E and connecting to the cylindrical cannula base portion guide tube 50, and (ii) the twin tumescent-type cannula assembly 5 employed in the first illustrative embodiment 4A (FIGS. 2D1 through 2E5) having an inner cannula 5B coupled to an electrically-powered cannula drive mechanism disposed within the hand-supportable housing and powered by a source of electrical power, while its stationary outer cannula 5B is releasably connected to the front portion of the hand supportable housing; (ii) a system controller 4B' for controlling the electro-cautery, irrigation and illumination functions supported by the fat aspiration instrument 4A' of the present invention.

FIGS. 3D1 through 3D8 show how the components of the visceral fat aspiration instrument of the present invention are assembled, in a step wise manner.

Figure 3A:
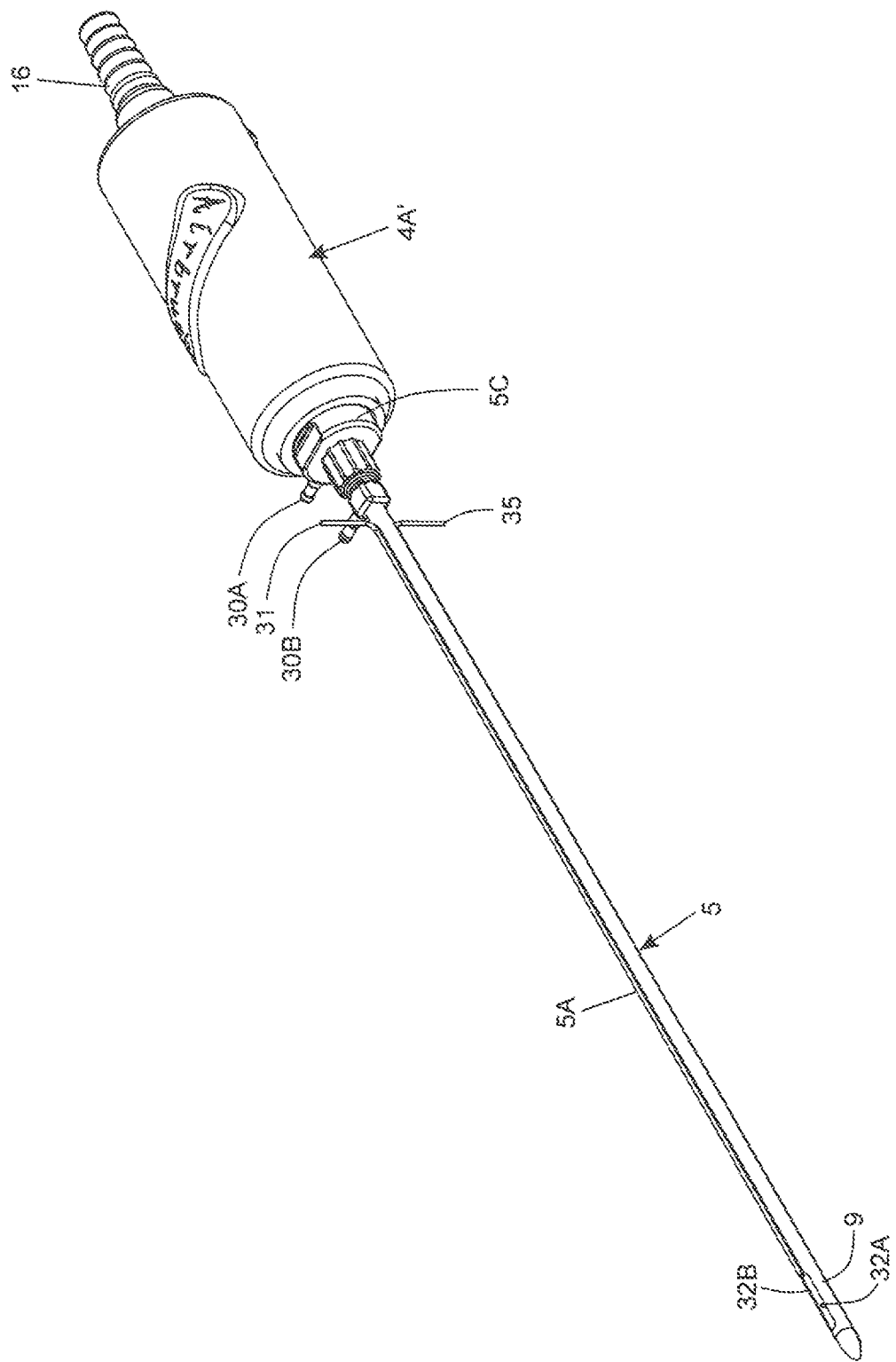
FIG. 3A is a perspective view of the electromagnetically-powered fat aspiration instrument shown in FIG. 3, having an twin-cannula assembly supporting three-functions (i.e. tumescent infusion, electro-cautery and variable-spectrum illumination) about the aspiration aperture during visceral fat aspiration operations.
Figure 3B:
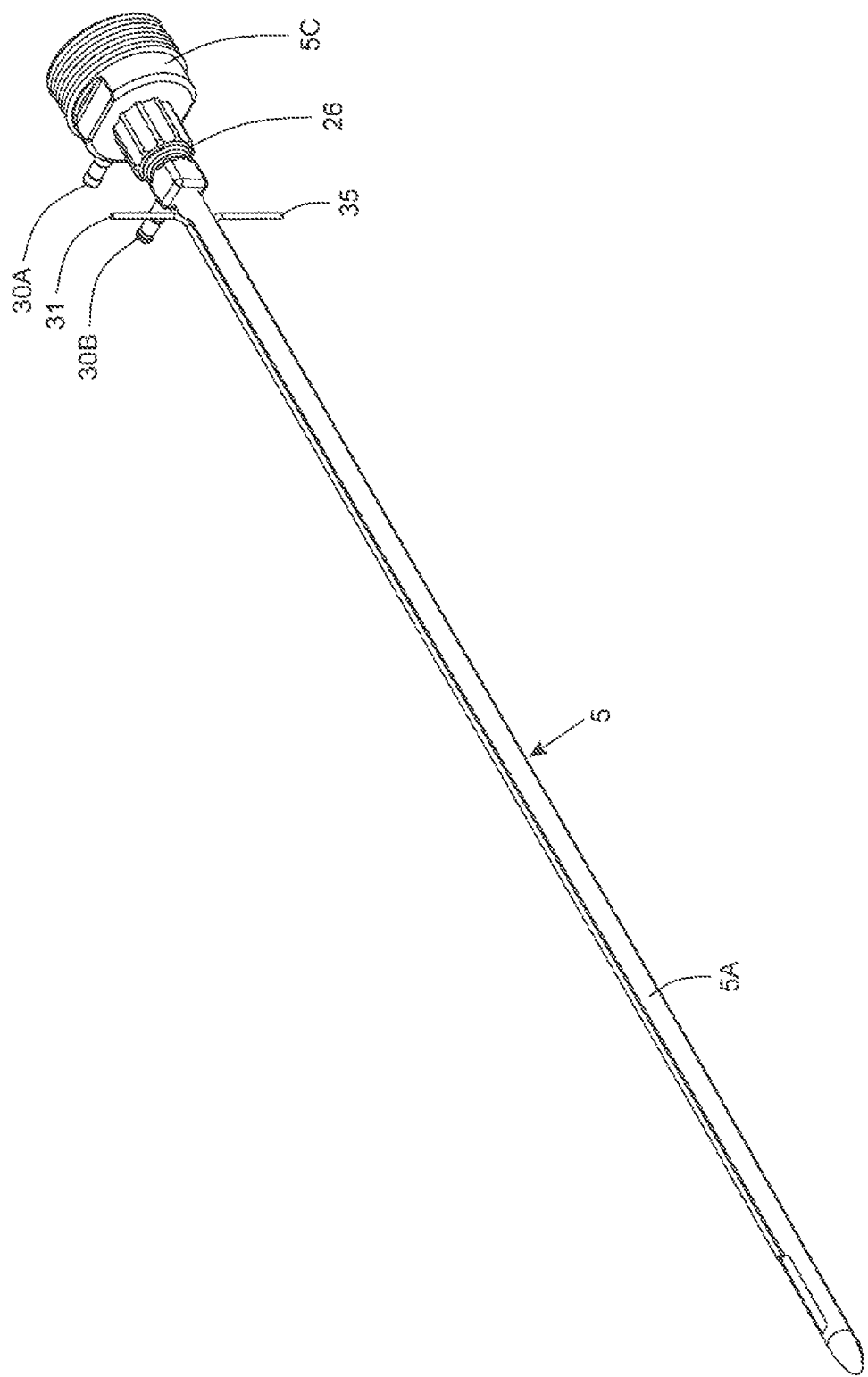
FIG. 3B is a perspective view of the multi-function twin-cannula assembly of the present invention employed on the instrument shown in FIGS. 2A and 3A, showing electro-cautery contacts on the base portion of the outer cannula to which RF signal signal cables are connected.
Figure 3C:
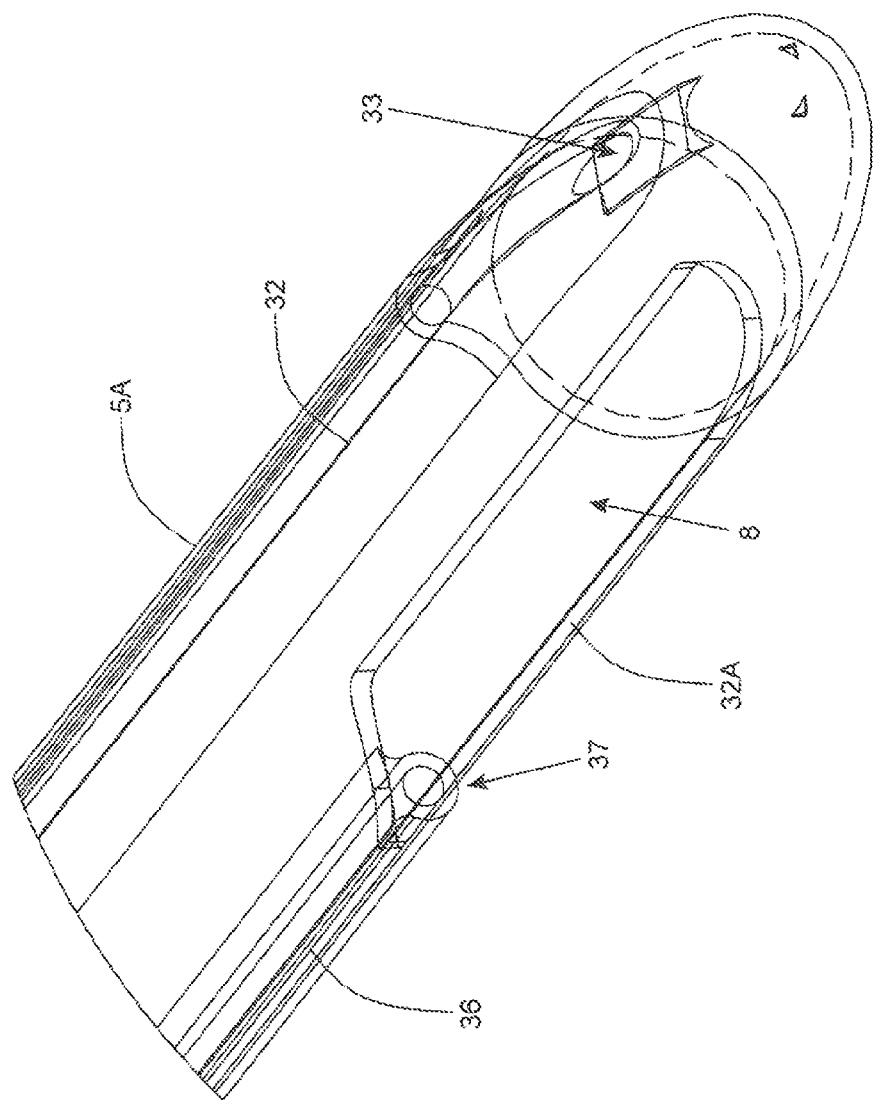
FIG. 3C is a first partially cut-away perspective view of the distal (tip) portion of the outer cannula component of the twin-cannula assembly of the present invention, illustrating its fiber carrying the illumination source to the field about the outer aspiration aperture, and irrigation channel conducting irrigation fluid to the bullet tip area of the outer cannula.
Figure 3E:
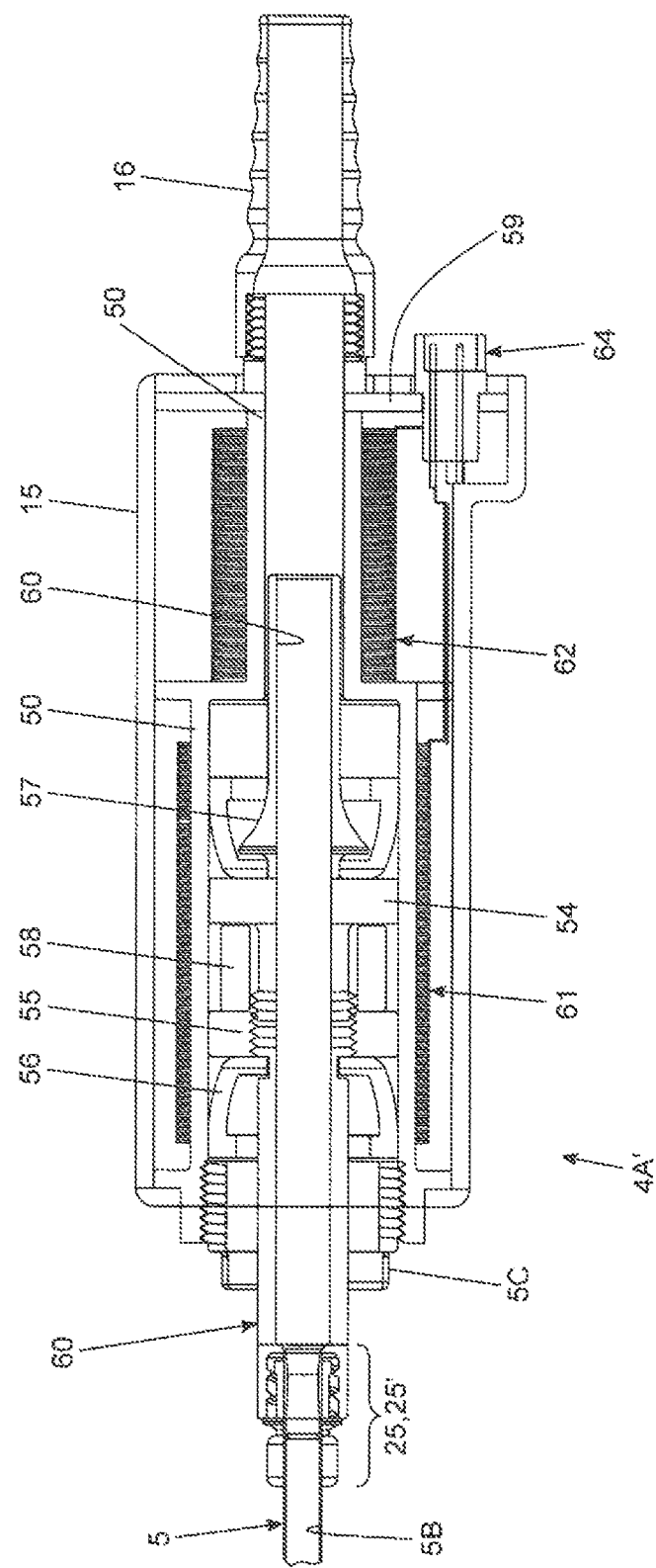
FIG. 3E is a partially-cutaway cross-sectional view of the bipolar electro-cauterizing fat aspiration instrument taken along line 3F-3F in FIG. 3A.
Figure 3H:
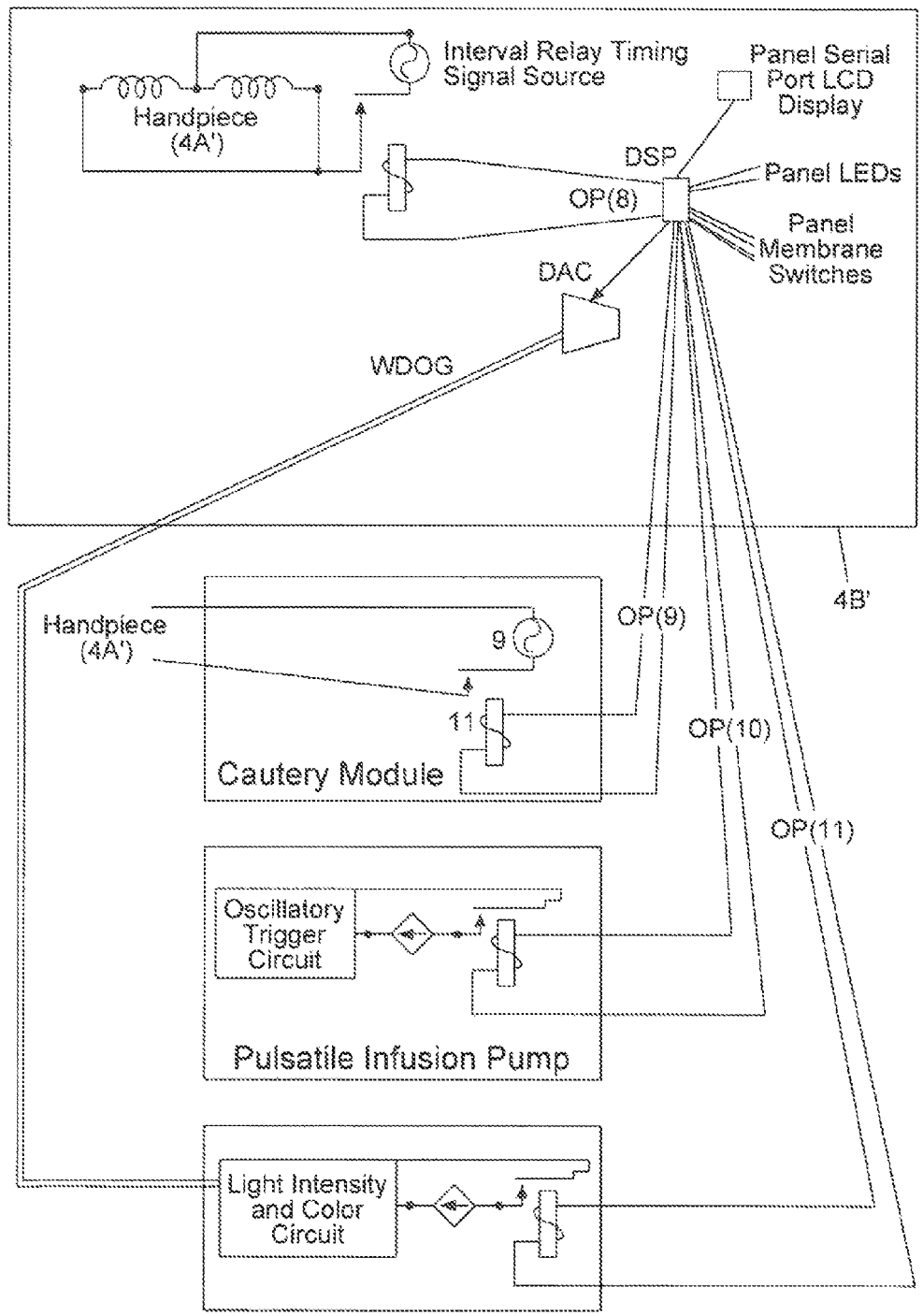
FIG. 3H is a schematic diagram for the system controller employed by the second illustrative embodiment of the fat aspiration instrumentation system of FIG. 3A, supporting electro-cauterizing, irrigation and illuminating functions about the outer aspiration aperture of the fat aspiration instrument.

As shown in FIG. 3E, the hand-supportable visceral fat aspiration instrument 4A' comprises: a cylindrical guide tube 1 mounted within the hand-supportable housing 2, and the (disposable) inner cannula base portion 50 carries a permanent magnetic ring 58 between a set of fluid seals 56 and 7 that slidably support the cannula base portion 60 within the cylindrical guide tube 50. The inner cannula 5B is coupled to the cannula base portion 60 by way of a mated leur-lock coupling 25, 25' and the lumen extending within the cannula and its inner cannula base portion 60 is in fluid communication with the stationary tubing connector 16, by way of the interior volume of the cylindrical guide tube 50 between the cannula base portion 60 and the stationary tubing connector 16. The stationary tubing connector 16 (having a barbed tubing connector portion) is adapted to unscrew from the rear portion of the hand-supportable housing so that housing back plate 59 can be removed so that the cylindrical guide tube 50 (i.e. the wound bobbin) can be slid into the hand-supportable housing 15. The top and bottom of the hollow cylindrical ring magnet 58 produce opposing magnetic poles, and magnet 58 is secured onto the inner cannula base portion 60 and against flange 54 by way of nut 55 which screws onto a set of threads form on other surface of the cannula base portion 60. In the illustrative embodiment, the fluid seals 56, 57 are realized as a pair of thin-walled, collapsable (i.e. invertible) bell-shaped silicone sealing washers which act as front and rear diaphragms allowing motion of the cannula base portion within the cylindrical guide tube. By setting mid-point geometry, one washer can effect a return stroke without need of coil polarity reversal, simply pulsing sufficing. Mounted about outer surface of the cylindrical guide tube, front and rear coil windings 61 and 62 are formed, respectively, and electrically connected to the connector plug 64 formed on the rear end of the hand-supportable housing.

FIG. 3D2 clearly reveals the components of the instrument 4A' as comprising: cylindrical guide tube 50 with flanges for containing electromagnetic coil windings (61, 62); hand-supportable housing 15; housing back plate 59; stationary tubing connector 16 with a vacuum tubing barb; flange 54 on inner cannula base portion 60; magnet fastening nut 55; front washer 56; back washer 57; ring magnet 58; inner cannula 5B provided with a luer lock fastener 25; front chamber screw cap 10; back electromagnetic coil 61; front electromagnetic coil 62; disposable inner cannula base portion 60 provided with as luer lock fastener 25'; and contact/connector plug 59 (e.g. Binder 719).

FIGS. 3D1 through 3D8 show how these components are assembled in step order fashion, in a front-loading manner, and the twin-cannula assembly 5 is simply connected to the (disposable) inner cannula base portion 60, using luer lock coupling mechanisms 25, 25' well known in the art, to completely assemble the instrument and prepare it for use in surgery.

Taken together, FIGS. 3F1 through 3F4 shows how the first and second electromagnetic coils 61, 62 are wound about the cylindrical guide tube 50, and then how wiring of these coils are electrically connected to the electrical connector mounted on the housing back plate 59, employed in the first illustrative embodiment shown in FIGS. 2A through 5E. FIG. 3F5 shows a schematic diagram depicting how the two coil 61 and 62 are driven by a push-pull type of circuit, for the purpose of enabling the inner cannula drive mechanism employed in the hand-supportable fat aspiration instrument 4A' illustrated in FIG. 3A.

Third Illustrative Embodiment of the Visceral Fat Aspiration Instrument System of the Present Invention In FIG. 3G1, an alternative embodiment of the hand-supportable fat aspiration instrument of FIG. 3A, depicted as 4A" is shown, comprising: a cylindrical (inner cannula base portion) guide tube 50" adapted to support three electromagnetic coils, rather than two coils used in the first illustrative embodiment 4A', for the purpose of implementing the inner cannula drive mechanism employed in the fat aspiration instrument. FIG. 3G2 shows a schematic diagram for this three coil push-pull type of circuit, driven by a 1-30 HS AC electrical signal, for enabling the inner cannula drive mechanism employed in the alternative embodiment of the hand-supportable fat aspiration instrument 4A" in FIG. 6A. In all other respects, the fat aspiration instrument of the third illustrative embodiment 4A" is like the fat aspiration instrument 4A'.

Specification of the In-Line Visceral Fat Sampling Device of the Present Invention Referring to FIGS. 4 through 4I2, the in-line fat sampling device 14 of the present invention will now be described.

Figure 4A:
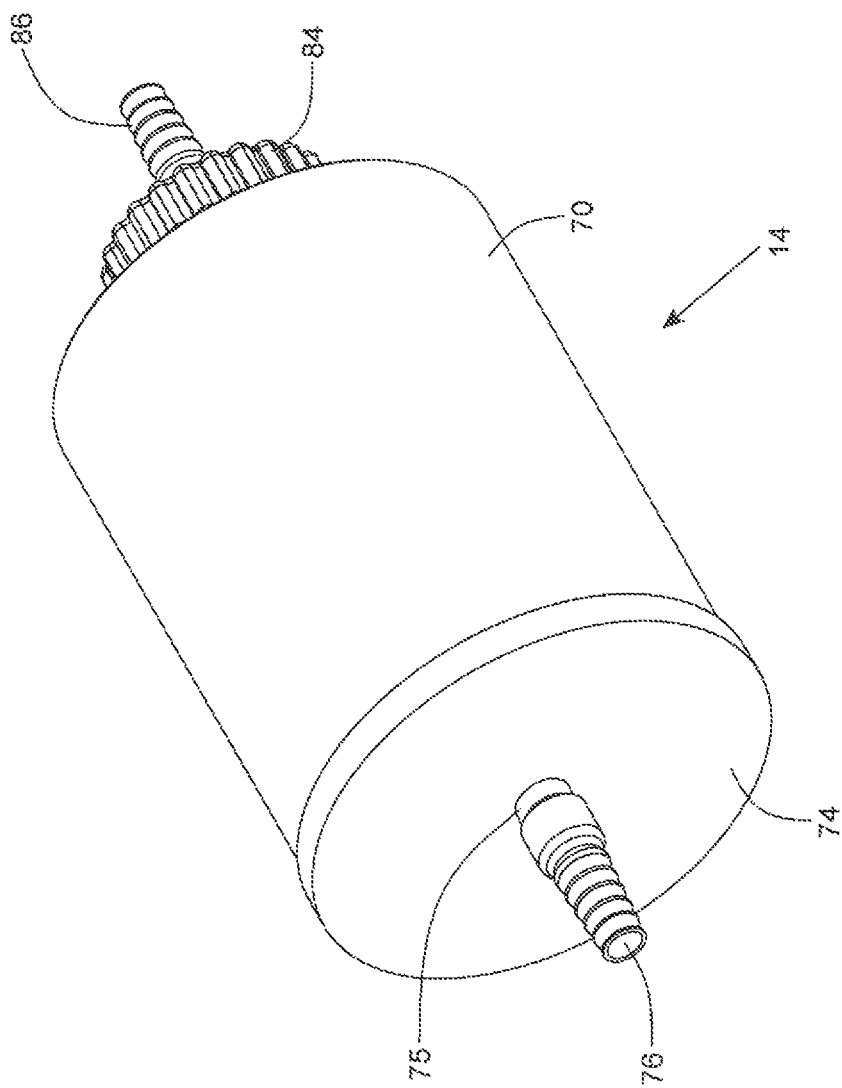
FIG. 4A is a first perspective view of the in-line fat sampling device of the present invention.
Figure 4B:
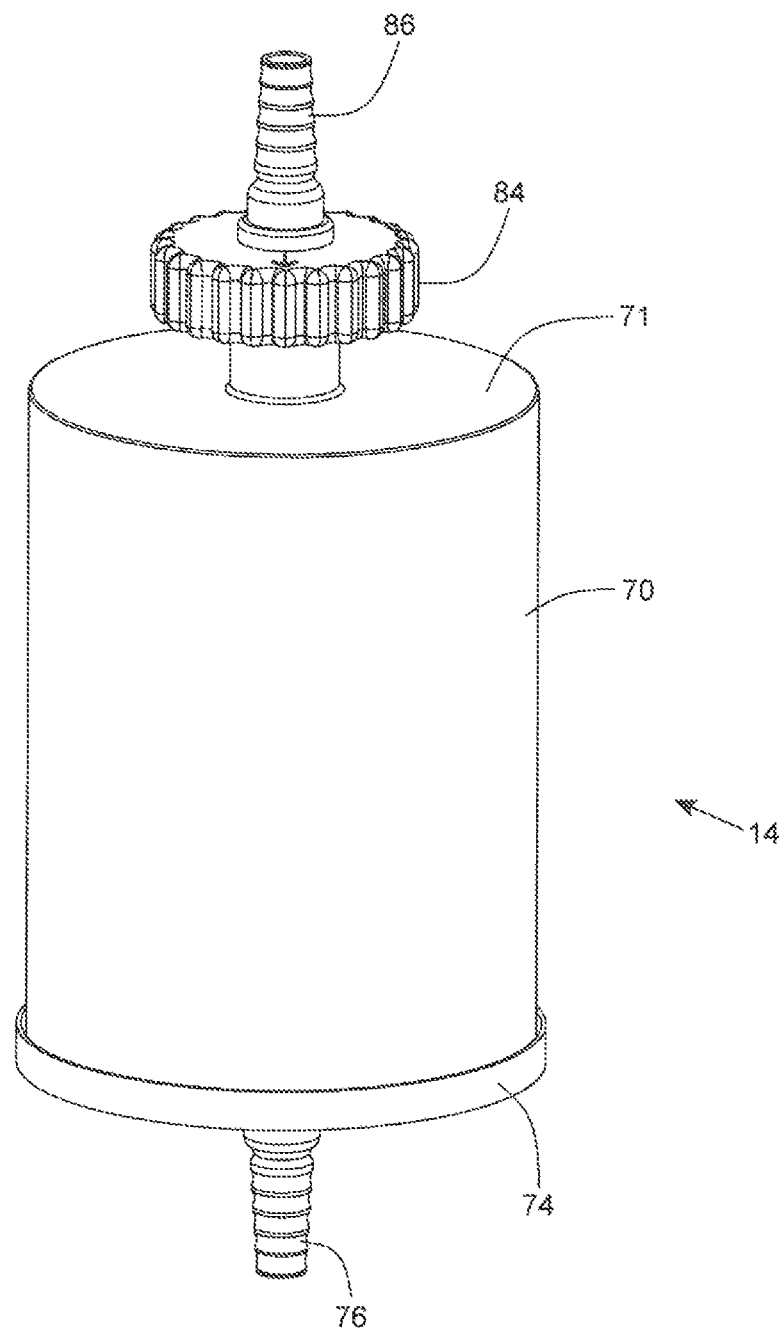
FIG. 4B is a second perspective view of the in-line fat sampling device of the present invention.
Figure 4D:
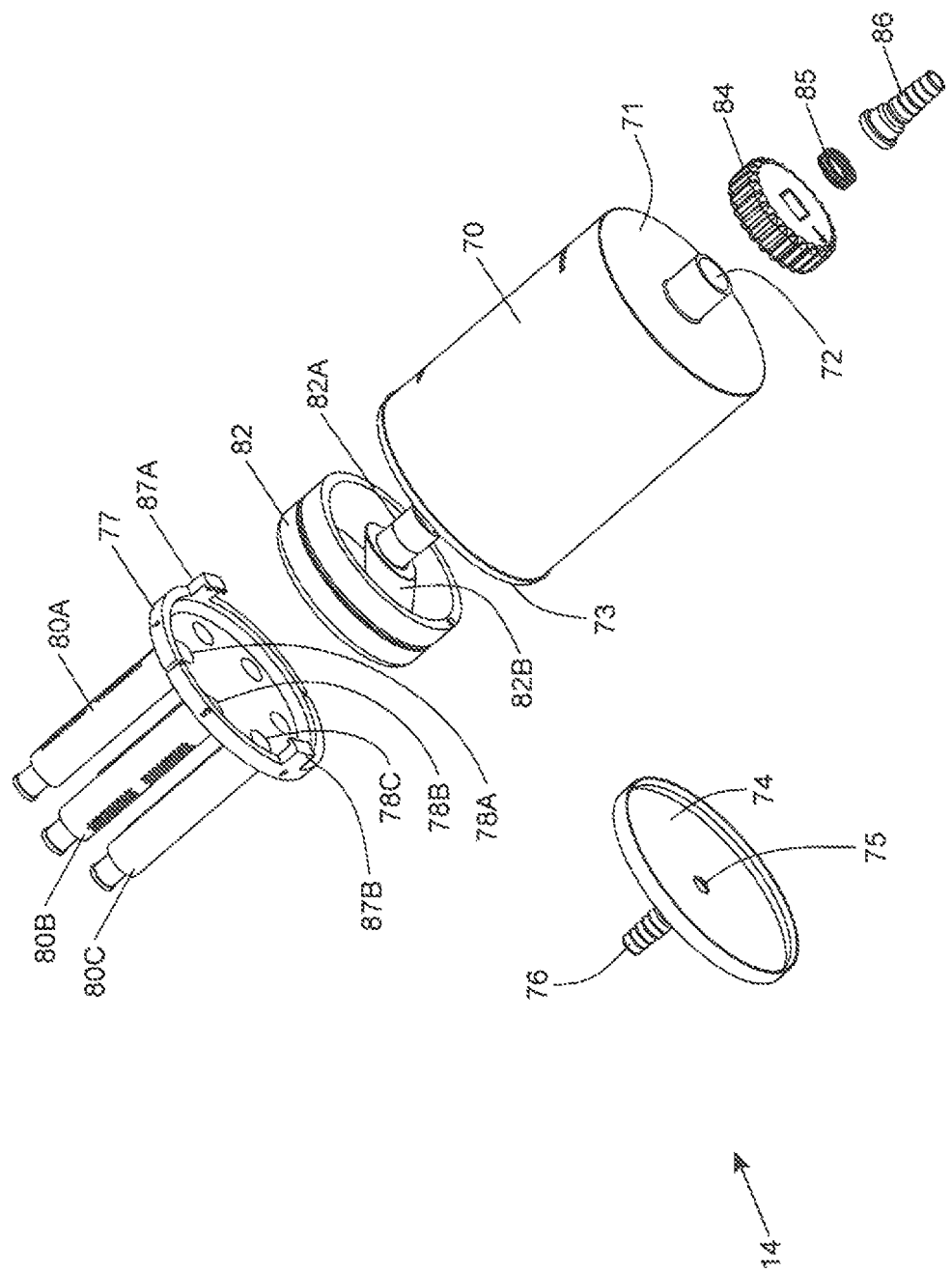
FIG. 4D is a second exploded view of the in-line fat sampling device of the present invention.
Figure 4E:
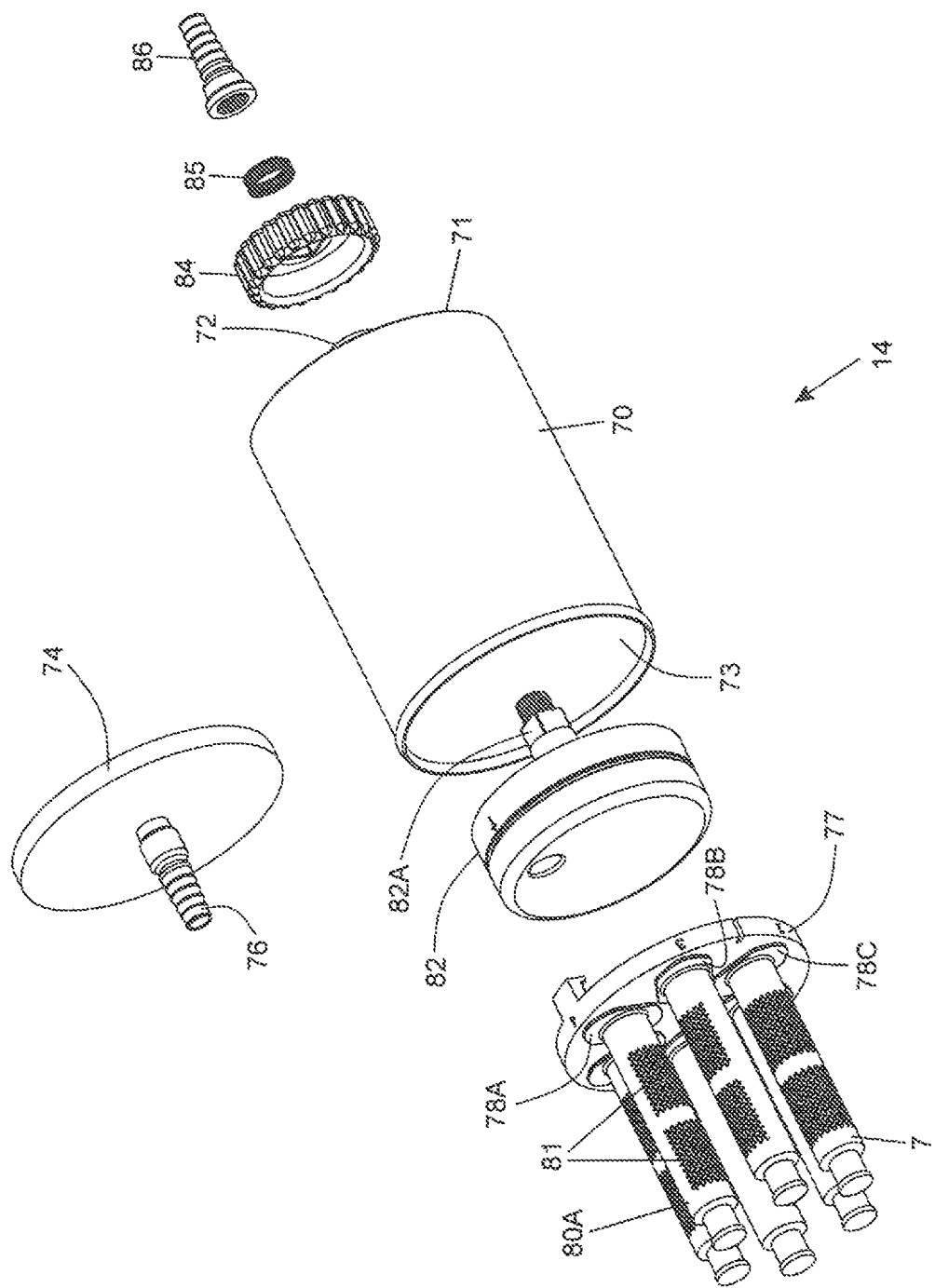
FIG. 4E is a third exploded view of the in-line fat sampling device of the present invention.
Figure 412:
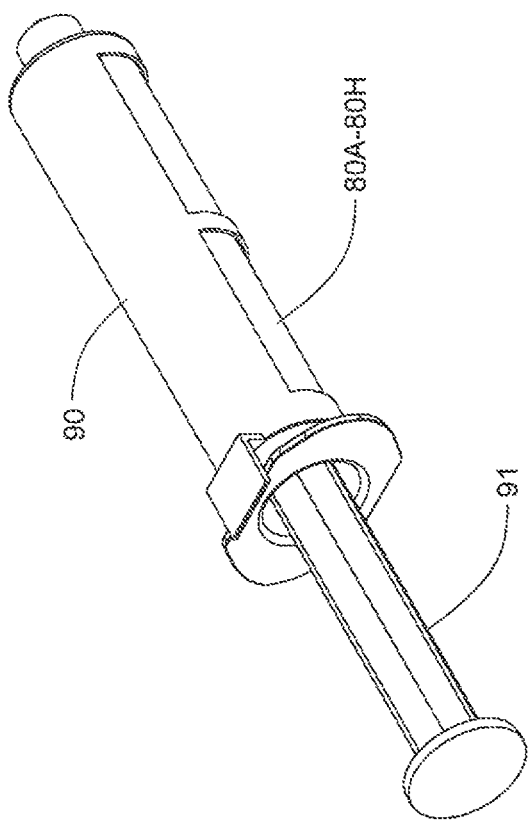

As shown in FIGS. 4C through 4E, the in-line fat sampling device 14 comprises: a optically-transparent collection chamber 70 having closed end 71 with a central aperture 72, and an open end 72 with hollow inner chamber/space disposed between the closed end 71 and the open end 73; a removable lid 74 for threaded connection to the open end of the collection chamber, and having a central flow channel 75 terminated in a first barbed connector 76 for connecting the device to vacuum source 4E by way of a section of flexible vacuum tubing 9B; a stationary suction plate 77 having six hollow projections 78A through 78H for supporting the open ends of six sample syringes 80A through 80H, each having perforations 81 in the walls thereof (to allow fluid to flow therethrough while in the collection chamber) and being keyed for registration with the collection chamber (to prevent rotation); a rotatable selector 82 (shown in FIG. 4F1) for rotational engagement with the suction plate 77 and having a hollow central post section 82A that passes through central aperture 72 and establishes fluid communication with a passage/conduit 82B that extends from center of the to periphery to control the flow of aspirated fat sample from the instrument 4A, 4A', 4A" through the first section of tubing 9A, through the selector 82 and into the selected syringe/projection 80 combination; a turning knob 84 mounted on and engaging with the hollow selector post 82A and enabling the turning of the rotatable selector 82 relative to the stationary suction plate 77 to select the syringe/projection combination into which an aspirated fat sample should flow for collection and indexing purposes during surgery; a spring 85 mounted between the turning knob 84 and hollow selector post 82A to push up the turning knob and keeping the selector 82 at the bottom of the collection chamber; and a second barbed connector 86 connected by threads to the hollow selector post 82A allowing the fat sampling device 14 to be connected to the fat aspiration instrument 4A, 4A' by way of a second section of flexible vacuum tubing 9B.

Surgeon installs the fat sampling device 14 inline between the fat aspiration instrument 4A, 4A' and the vacuum source 4E as shown in FIG. 4A. The collection chamber 70 is labeled for orientation, indicating the side to patient and the side to vacuum source. The turning knob 84 has an arrow on it. The suction plate 77 has numbers 1-6 for each of the stoppered perforated syringe barrels 80A-80H connected to it. The surgeon then pushes down on turning knob 84 against the biasing force of spring 85 and that pushes the selector slightly forward so the knob can be turned to select which syringe to collect to, until it is full, counting from 1 to six. The selector 82 has a detente dome extrusion which fits into the corresponding dimple below the selected syringe. The spring 85 maintains the selector 82 in its selected position. As shown in FIG. 4E and 4F1, suction plate 77 has two flanges 87A and 87B which snap over the selector 82, and grip a groove that runs around it to secure it in place relative to the selector 82.

When practicing the method of treatment according to the present invention, the surgeon initially performs sampling of visceral fat in the SB mesentery of the small bowel, starting at the duodenum, the beginning, middle and distal jejunum and the ileum before returning to the proximal jejunum to begin the first defatting treatment, with the circulating nurse noting into which syringe the aspirated fat from each area is being collected. When all syringes are full with fat, unit is disconnected and vacuum source is connected directly to the hand piece. The fat sampling device may be replaced with another one for sampling at shorter distances if desired.

As shown in FIG. 4F2, during fat aspiration operation using the system of the present invention, an aspirated fat sample flows from the abdominal region of the patient, through the fat aspiration instrument of the present invention, through tubing 9A and the hollow selector post 82A, through passageway/flow director 82B, into the selected collection syringe 80A-80H supported on the stationary suction plate 77 and capped with cap portion 80A-80H, respectively. Fat cells are collected within the selected syringe while excess fluid is expressed through holes in the selected syringe, and passed out through the barded connector 76 towards to vacuum source 4E.

FIG. 4G shows a process of removing collected visceral fat samples contained in syringes in the in-line fat sampling device of the present invention. This involves removing the lid portion 74, and withdrawing the syringes supported on the suction plate assembly 77. Then as shown in FIGS. 4H and 4I, a capped fat containing syringe 80A is removed from the suction plate 77 and snapped into an syringe hole occluder 90 and rotated to as to occlude the holes/perforations 81 formed in the walls of the syringe, as shown in FIG. 4A1. Then a plunger 91 is inserted into the syringe, and the indexed fat samples is expressed out for testing and analysis purposes, typically in one or more of the laboratory methods described below.

In general, the kind of tests/measurements to be performed on a visceral fat sample will depend on the condition being treated. However, it would be helpful to measure concentrations of particular _____ per gm of aspirated fat per region, using the following laboratory methods: measure resistin levels using the Resistin human ELISA kit (VinciBiochem, Vinci-FI, Italy]; determine adiponectin levels using a radioimmunoassay method [Linco Research, St. Charles, Mo., USA; and quantify TNF-a, interleukin-6 (IL-6), and IL-10 using an enzyme-linked immunoassay (ELISA) method [BioSource Cytoscreen, ELISA UltraSensitive Kits, Camarillo, USA].

Subsequent serial defattings will target the region showing the highest (measured) levels of leptin, and resistin, TNF-alpha, and Interleukin 6 (IL-6) and lowest levels of adipopectin. IL-6 is aninflammatory markers associated with increased risk of coronary artery disease and insulin resistance.

The Science Underlying the Methods of Treatment According to the Present Invention The science underlying the visceral fat aspiration based methods of the present invention is represented in the schematic illustrations set forth in FIGS. 5A through 5D.

Figure 5A:
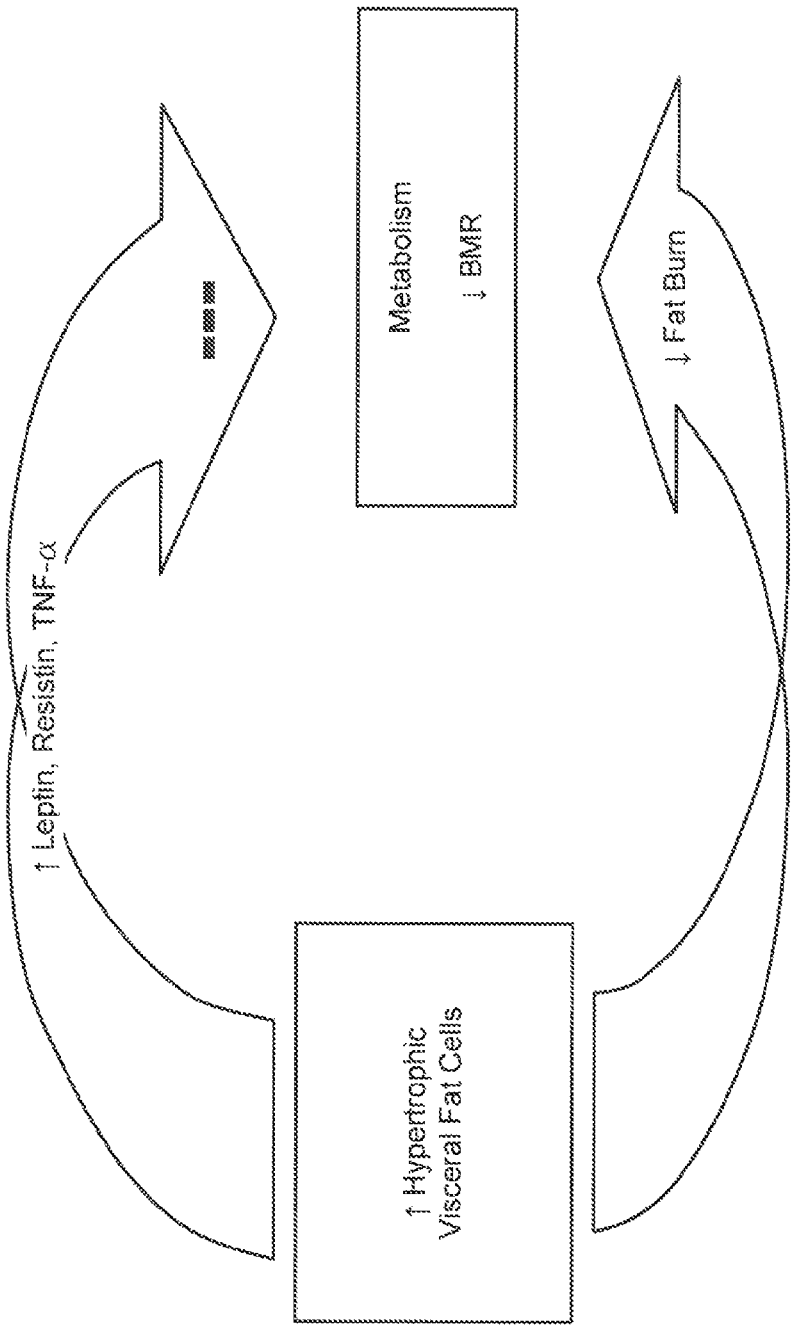
FIG. 5A is a schematic diagram of the process illustrating the increased negative feedback effect (i.e. decrease in fat burn) which an increase in hypertropic visceral fat cells have upon the basal metabolic rate (BMR) within a human being's metabolism, by the increased secretion of Leptin, Resistin and TNF-α—prior to treatment according to the principles of the present invention.

FIG. 5A illustrates the increased negative feedback effect (i.e. decrease in fat burn) which an increase in hypertropic visceral fat cells have upon the basal metabolic rate (BMR) within a human being's metabolism, by the increased secretion of Leptin, Resistin and TNF-α—i.e. prior to treatment according to the principles of the present invention.

Figure 5B:
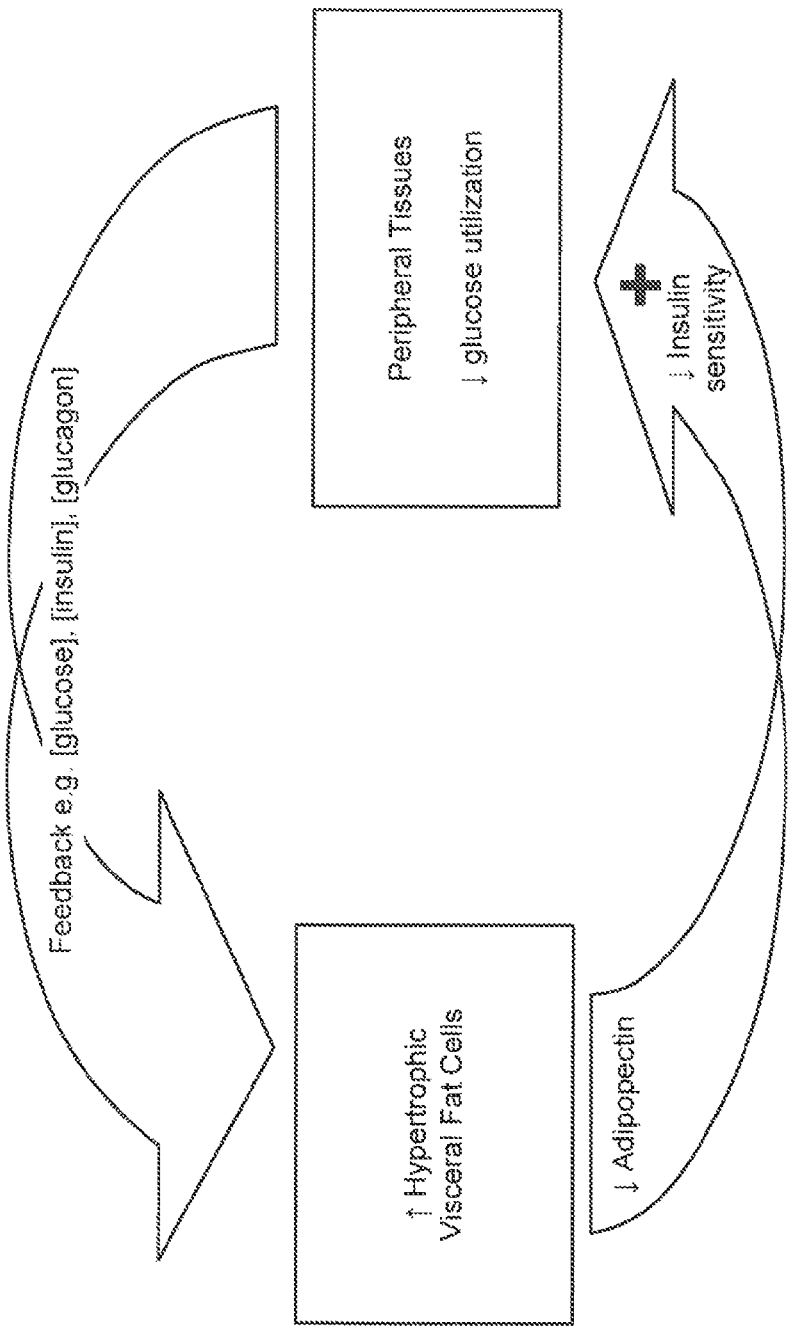
FIG. 5B is a schematic diagram of the process illustrating a decreased secretion of Cytokines (i.e. Adipopectin) in response to an increase in hypertropic visceral fat cells, favoring a decrease in sensitivity of peripheral tissues to insulin and thus a decrease in glucose utilization thereby—prior to treatment according to the principles of the present invention.

FIG. 5B illustrates a decreased secretion of Cytokines (i.e. Adipopectin) in response to an increase in hypertropic visceral fat cells, favoring a decrease in sensitivity of peripheral tissues to insulin and thus a decrease in glucose utilization thereby—i.e. prior to treatment according to the principles of the present invention.

Figure 5C:
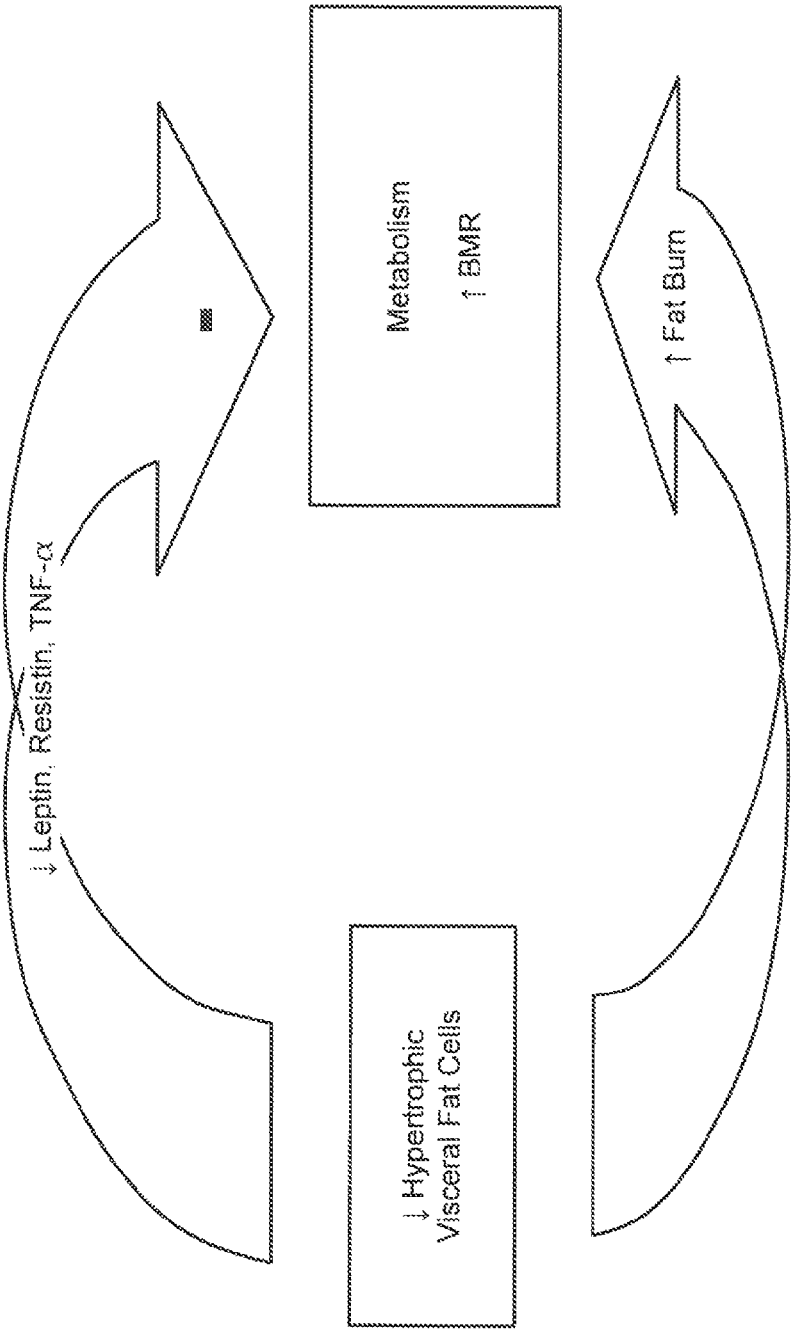
FIG. 5C is a schematic diagram of a process illustrating a reduction in the number of hypertropic fat cells and their harmful secretions (i.e. Leptin, Resistin and TNF-α) by the method of treatment according to the present invention, and the favorable impact on the patient's metabolism by increasing fat burn and the basal metabolic rate (BMR)

FIG. 5C illustrates a process caused by reducing the number of hypertropic fat cells and their harmful secretions (i.e. Leptin, Resistin and TNF-α) by the method of treatment according to the present invention, and the favorable impact on the patient's metabolism by increasing fat burn and the basal metabolic rate (BMR).

Figure 5D:
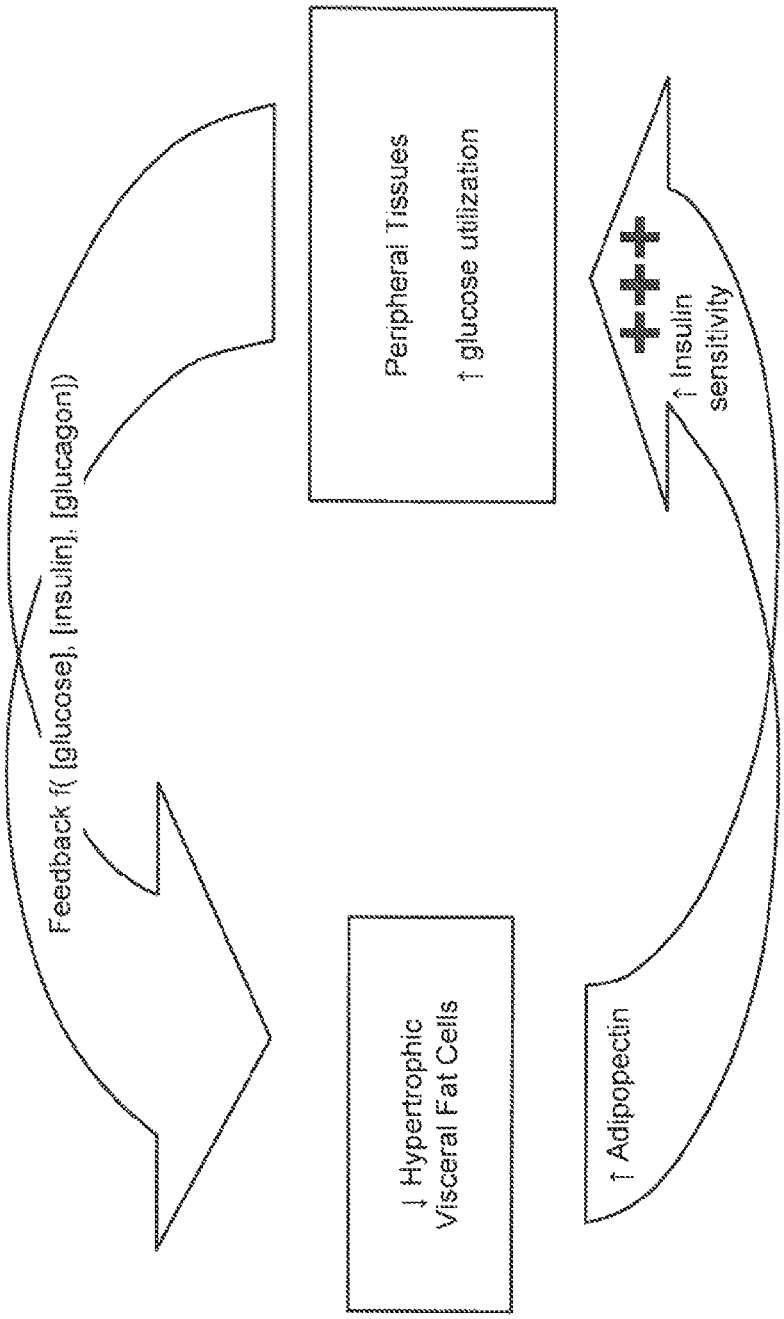
FIG. 5D is a schematic diagram of the process illustrating an increased circulation of secretion of Cytokines (i.e. Adipopectin) in response to a decrease in hypertropic visceral fat cells by practicing the method of treatment according to the present invention, and the favorable increase in sensitivity of peripheral tissues to insulin and thus an increase in glucose utilization thereby.

FIG. 5D illustrates a process of increased circulation of secretion of Cytokines (i.e. Adipopectin) in response to a decrease in hypertropic visceral fat cells by practicing the method of treatment according to the present invention, and the favorable increase in sensitivity of peripheral tissues to insulin and thus an increase in glucose utilization thereby.

Figure 10:
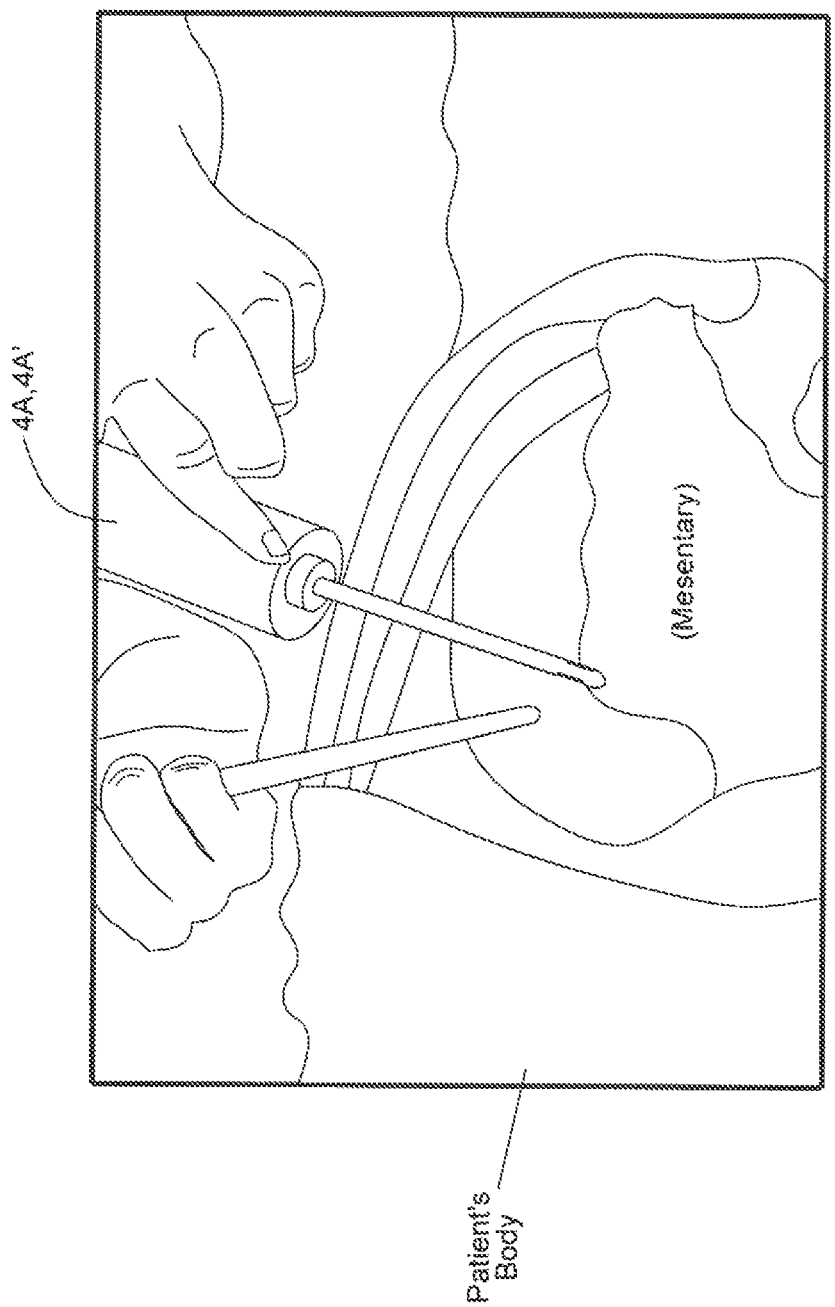
FIG. 10 is a graphical illustration of the cross-section partially cut away view of the patient's abdominal region during a later phase of the mesenteric visceral fat aspiration procedure of the present invention, showing the aspiration and electro-cauterization of visceral fatty tissue in the mesentery, using the laparoscopically-guided irrigating bipolar electro-cauterizing twin-cannula visceral fat aspiration instrumentation of the present invention.

In FIG. 10, a cross-sectional view of the patient's abdominal region is provided during a later phase of the mesenteric visceral fat aspiration procedure of the present invention, showing the aspiration and electro-cauterization of visceral fatty tissue in the mesentery, using the laparoscopically-guided irrigating bipolar electro-cauterizing twin-cannula visceral fat aspiration instrumentation of the present invention.

Figure 11:
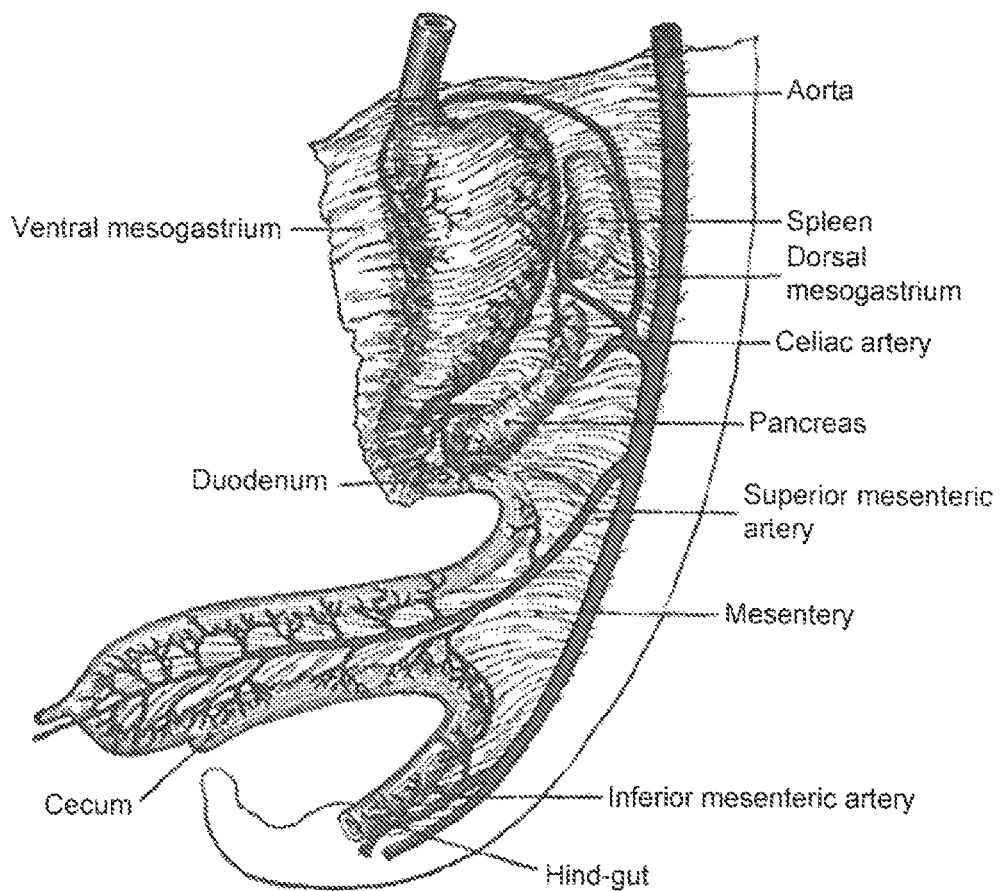
FIG. 11 is a graphical illustration of the abdominal region of a patient, showing areas where visceral fat is to be removed in the middle ⅓ of the mesentery, while avoiding the major vessels at the root of the mesentery near the aorta and the smaller direct supply vessels (vasa recti) near the bowel itself (i.e. where a great amount of visceral fat is located—in the fan-folded condensation of mesentery thickened with visceral fat).

FIG. 11 shows areas where visceral fat is to be removed in the middle ⅓ of the mesentery—i.e avoiding the major vessels at the root of the messentery near the aorta and avoiding the smaller direct supply veseels (vasa recti) near the bowel itself i.e. where most the fat is anyway—in the fan-folded condensation of mesentery thickened with visceral fat.

Method of Treating Obesity According to the Principles of the Present Invention

Figure 6A:
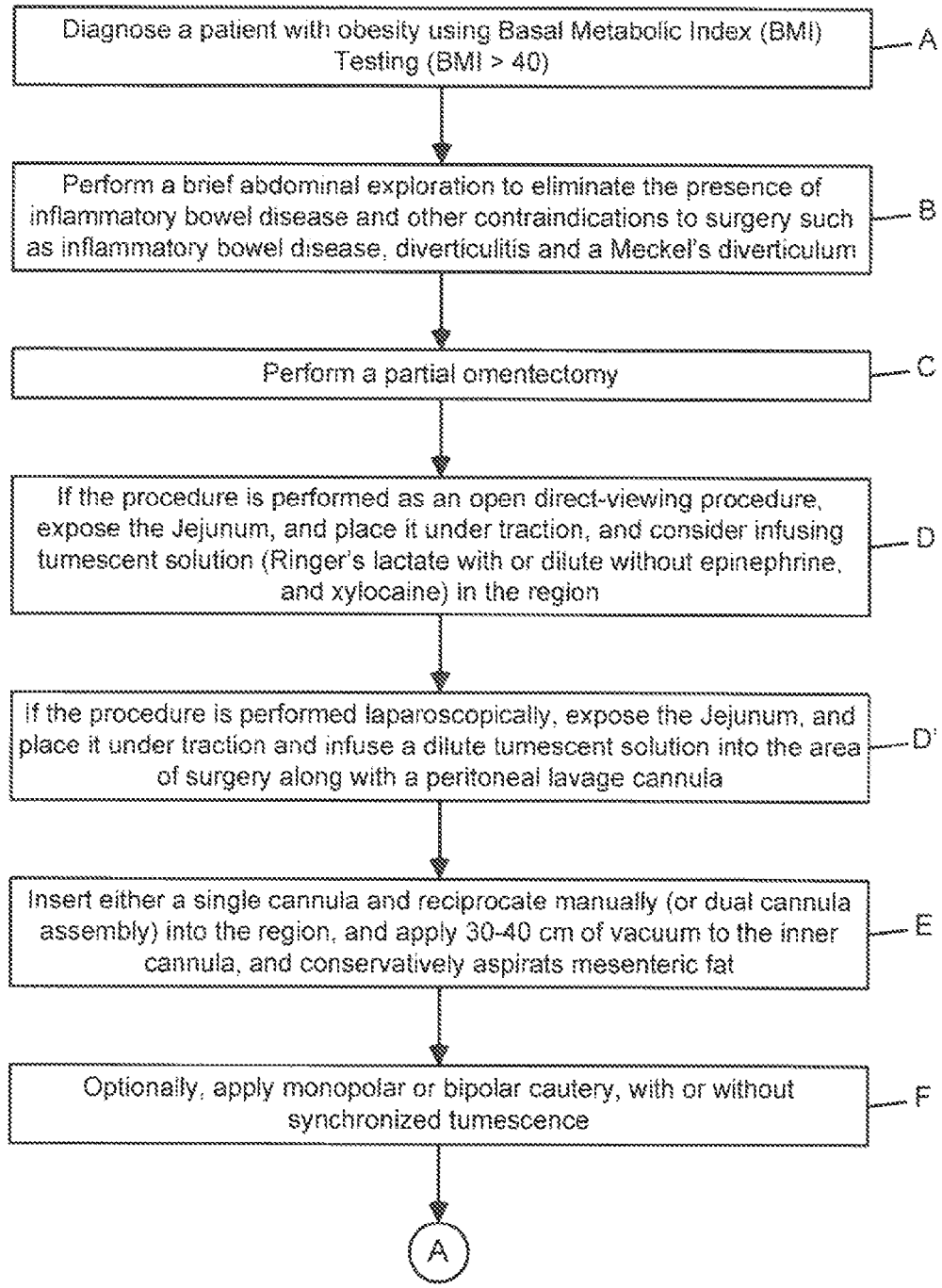
FIGS. 6A and 6B a flow chart illustrating the primary steps carried out during the illustrative embodiment of the method of treating obesity by mesenteric visceral fat aspiration according to the present invention, comprising diagnosis, exploration, partial omentectomy, small bowel mesenteric visceral fat aspiration, large bowel mesenteric visceral fat aspiration, followed by subcutaneous visceral fat aspiration, abdominal and dermatolipectomies as indicated.
Figure 6B:
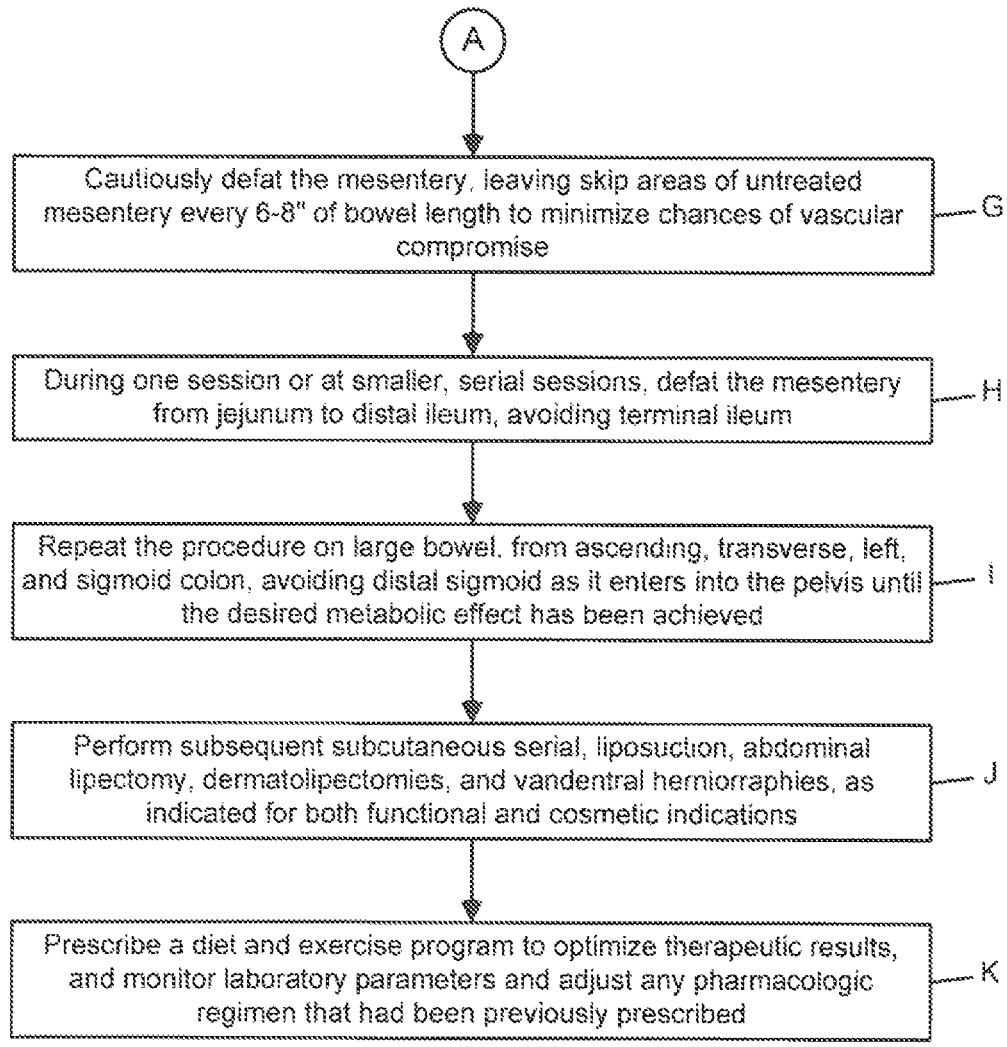

FIGS. 6A and 6B illustrate the primary steps carried out when practicing the method of treating morbid obesity by mesenteric visceral fat aspiration according to the illustrative embodiment of the present invention, comprising the steps: diagnosis, exploration, partial omentectomy, small bowel mesenteric visceral fat aspiration, large bowel mesenteric visceral fat aspiration, followed by subcutaneous visceral fat aspiration, abdominal and dermatolipectomies as indicated. Preferably, the fat aspiration operations indicated above are carried out using the apparatus described in FIGS. 1 through 4I2, although it is understood that other techniques and apparatus can be used.

As indicated in Step A in FIG. 6A, the surgeon diagnoses a patient with metabolic syndrome and/or obesity (morbid obesity) using the waist-to-hip ratio (WHR) and by physical measurements and lab tests. Morbid Obesity is defined as being 100 lbs over the ideal body weight or having a Body Mass Index (BMI) greater than or equal to 40.

As indicated in Step B in FIG. 6A, the surgeon performs a brief abdominal exploration or inspection to eliminate the presence of inflammatory bowel disease and other contraindications to surgery, such as, diverticulitis and a Meckel's diverticulum, or any other pathology. At her option, the surgeon may infuse a tumescent solution (Ringer's lactate with or without dilute epinephrine, and with or without xylocaine) as described above to prepare the area for treatment.

As indicated in Step C in FIG. 6A, the surgeon performs a partial omentectomy by removing the redundant omental apron.

As indicated in Step D in FIG. 6A, when performed as an open direct-viewing procedure, the omentum is retracted and the jejunum is exposed. Either by the hands of an assistant in an open procedure or with aid of atraumatic laparoscopic graspers [Endo Babcock or Dolphin Nose Grasper], the proximal jejunum is isolated and placed under gentle tension. One atraumatic grasper is inserted in the right upper quadrant for retraction of the jejunum towards the liver, and a second atraumatic grasper is inserted in the left lower quadrant, placed on a section of jejunum approximately 6 to 8 inches distal to the previously placed grasper, and retracted caudally towards the left lower quadrant. The jejunum is placed under tension and the mesentery exposed and straightened.

As indicated at Step D in FIG. 6A, when performed as a laparoscopic procedure, a pneumoperitoneum is created in the usual fashion and the trochars are inserted so the procedure may be performed under laparoscopic guidance with multiple monitors. A partial omentectomy may be carried out by removing the caudal portions of the omentum. When performed laparoscopically, omentum is removed in strips to facilitate removal through laparoscopic portals. Care is taken to obtain strict hemostasis and to preserve an apron of protective omentum while it is substantially shortened and defatted.

Figure 9A:
FIG. 9A is a perspective view of the patient's abdominal region during the first phase of a mesenteric visceral fat aspiration procedure of the present invention, showing the inspection of the small bowel and placing a region of proximal jejunum under tension between two graspers for treatment, following creation of routine laparoscopy portals and customary $CO_2$ infusion for abdominal distension.

FIG. 9A depicts the bowel grasped between two clamps to tent up the mesentery.

Figure 9B:
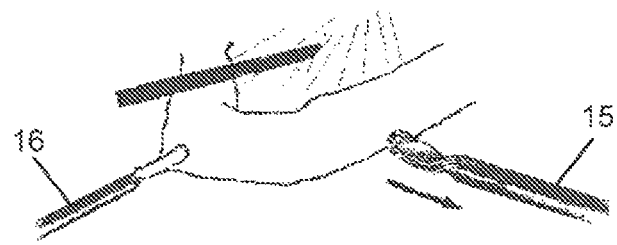
FIG. 9B is perspective view of the patient's abdominal region during a second phase of the mesenteric visceral fat aspiration procedure of the present invention, showing the insertion of a cannula into the mesentery for infusion of tumescent solution.

FIG. 9B depicts a cannula inserted into the tented mesentery to infuse tumescent solution.

Figure 9C:
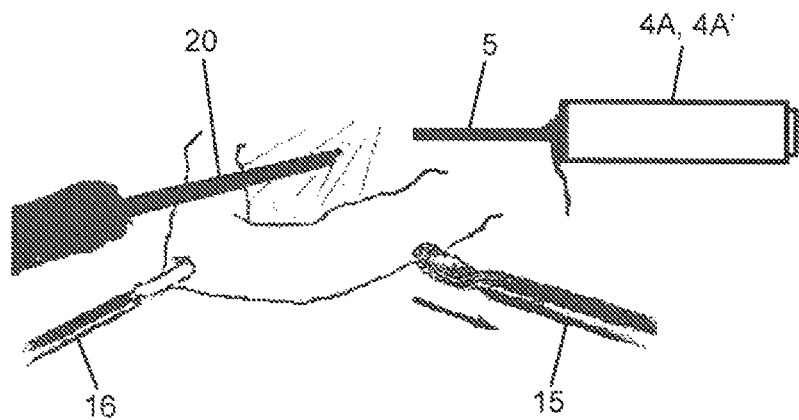
FIG. 9C is perspective view of the patient's abdominal region during a third phase of the mesenteric visceral fat aspiration procedure of the present invention, showing the insertion of the bipolar electro-cauterizing twin-cannula visceral fat aspiration instrument shown in FIG. 1, into the mesentery of the patient and fat removal by way of visceral fat aspiration under laparoscopy guidance with the laparoscope shown.

As indicated in Step E in FIG. 6A, a retractor is inserted through the right lower quadrant and placed posteriorly beneath the tented mesentery. An incision is made anteriorly in the mesentery, approximately ⅔ of the distance between its base and the bowel. The surgeon then inserts the power-assisted twin cannula assembly 5 into the region, and applies 30-40 cm Hg of vacuum to the inner cannula, and conservatively aspirates mesenteric fat. FIG. 9C depicts insertion of the twin cannula device 5 into the previously tumesced and tented mesentery.

When using the laparoscopically-guided twin-cannula visceral fat aspiration instrument system shown in FIGS. 1 and 2, there is much less risk of vascular disruption or visceral injury than when using single cannula instrument, because the twin-cannula instrument of the present invention protects the adventitia of the arboreal blood vessels from injury, and allows treatment of larger areas more rapidly and effectively.

As indicated in Step F in FIG. 6A, the surgeon optionally, applies bipolar electro-cautery, with or without synchronized tumescence. By including a separate fluidic channel in the outer cannula, extending from its base to its tip, it is possible to synchronize a pulsed infusion of tumescent solutions or irrigation (e.g. lactated Ringer's solution with or without small amounts of epinephrine (e.g. 1:100,000-1:400,000) through this additional channel in the tip of the twin cannula assembly with the advancement of the inner cannula, to facilitate fat aspiration with a sump effect. Alternatively, a totally separate cannula may be placed with the mesentery and used for pulsatile or non-pulsatile, synchronized or unsynchronized infusion near the tip of the twin cannula assembly 5.

By eliminating the battering ram effect of a reciprocating cannula and the need for tumescent solution for hemostasis, twin cannula visceral fat aspiration allows the minimally invasive removal of soft tissue in any location, including the intestinal mesentery by either open or laparoscopic approaches. Unlike single cannula visceral fat aspiration cannulas, the tube-within-a-tube construction of the twin cannula assembly 5 is particularly suited to a laparoscopic approach as all viscera are spared disruption from the moving member except the limited area of fat being aspirated in the mesentery adjacent to the outer cannula slot. The relatively stationary outer cannula reduces friction caused by the continually reciprocating inner cannula and the laparoscopy portal. Placement of the outer cannula 5A is positional, rather than actively reciprocating, to avulse particles of fat.

Twin cannula mesenteric visceral fat aspiration according to the principles of the present invention described above, thus allows direct correction of abdominal obesity, and in a less invasive and dramatically immediate fashion without the untoward nutritional consequences, hepatic, or renal complications of gastric bypass or banding procedures.

The use of twin cannula visceral fat aspiration, with or without bipolar cautery hemostasis and with or without a synchronized pulsed infusion of tumescent or irrigation solution through the cannula, offers a controlled, rapid, and safer way of treating a length of intestine with much less risk of bleeding or vascular injury.

Although bipolar hemostasis obviates the need for tumescence with epinephrine containing solutions, small amounts of epinephrine could be added to small pulses of lactated Ringer's solution, with or without small quantities of local anaesthetic, which are synchronized with the advancement of the inner cannula within the outer cannula.

Since the irrigation solution is immediately aspirated through the aspiration aperture 55 of the twin (twin) cannula assembly 5 of FIGS. 2A and 3A, the systemic effects of vasopressor and local anesthetics during twin cannula synchronized tumescence (TCST) would be more limited than an alternative means, such as infusion of a similarly dilute epinephrine and xylocaine in lactated Ringer's solution with a Tenckoff catheter via peritoneal lavage.

Epidural or general anaesthesia could replace or augment synchronized infusion or peritoneal lavage. Although TCST is the preferred embodiment of the described method, the present invention contemplates choosing modalities that are optimized for each individual patient's physiologic and cardiovascular status, and concentrations of xylocaine and epinephrine in the employed solutions from zero to therapeutic, as the situation dictates.

As indicated in Step G in FIG. 6B, the surgeon cautiously defats the mesentery, leaving skip areas of untreated mesentery every 6-8" of bowel length to minimize chances of vascular compromise. This step can be achieved by applying a vacuum of 30-40 cm Hg, and defatting the mesentery by initiating mechanical reciprocation of the inner cannula 5B within the outer cannula 5A of the transiently stationary twin cannula assembly 5. Care is taken to retain some fat and avoid creating defects that might allow intestine to herniate through, and any perforations in the mesentery are closed to eliminate this hazard. The area of treatment is inspected for hemostasis and any defects in the mesentery repaired. The jejunum between clamps is inspected for good vascular supply.

As indicated in Step H IN FIG. 6B, during a single session or during smaller, serial sessions, the surgeon defats the mesentery from jejunum to distal ileum, avoiding terminal ileum. Then, as with the open approach, a small area is skipped much like a radiating spokes on a wheel to assure continuity of blood supply, and the next 8" area of jejunum is tented and the procedure repeated until the terminal ileum is reached and left untreated. Any difficulties with hemostasis or questionable vascular viability of the bowel indicate the necessity of a resection and possible conversion to an open procedure.

As indicated in Step I in FIG. 6B, the surgeon repeats the procedure on the large bowel and/or the small bowel for greatest effect. The mesentery of the large bowel would be approached from the ascending colon to the sigmoid colon, avoiding the area surrounding the ileocecal valve, and the distal sigmoid colon as it descends into the pelvis, and the mesentery to any areas of large bowel which appear grossly involved with diverticulitis.

As indicated in Step J in FIG. 6B, the surgeon performs subsequent subcutaneous serial, visceral fat aspiration, abdominal lipectomy, dermatolipectomies, and ventral herniorraphies, as indicated for both functional and cosmetic indications. Large volume subcutaneous visceral fat aspiration, panniculectomy, abdominoplasty, repair of any ventral hernias or diastasis recti could be carried out in serial sessions to obtain a much tightened abdominal corset for both functional and cosmetic improvement. The majority of these procedures can be performed under conscious sedation and on an ambulatory basis on these patients with minimal complications because of their improved metabolic profiles.

As indicated in Step K in FIG. 6B, the surgeon prescribes a diet and exercise program to optimize therapeutic results, and monitors laboratory parameters and adjust any pharmacologic regimen that had been previously prescribed.

Figure 7A:
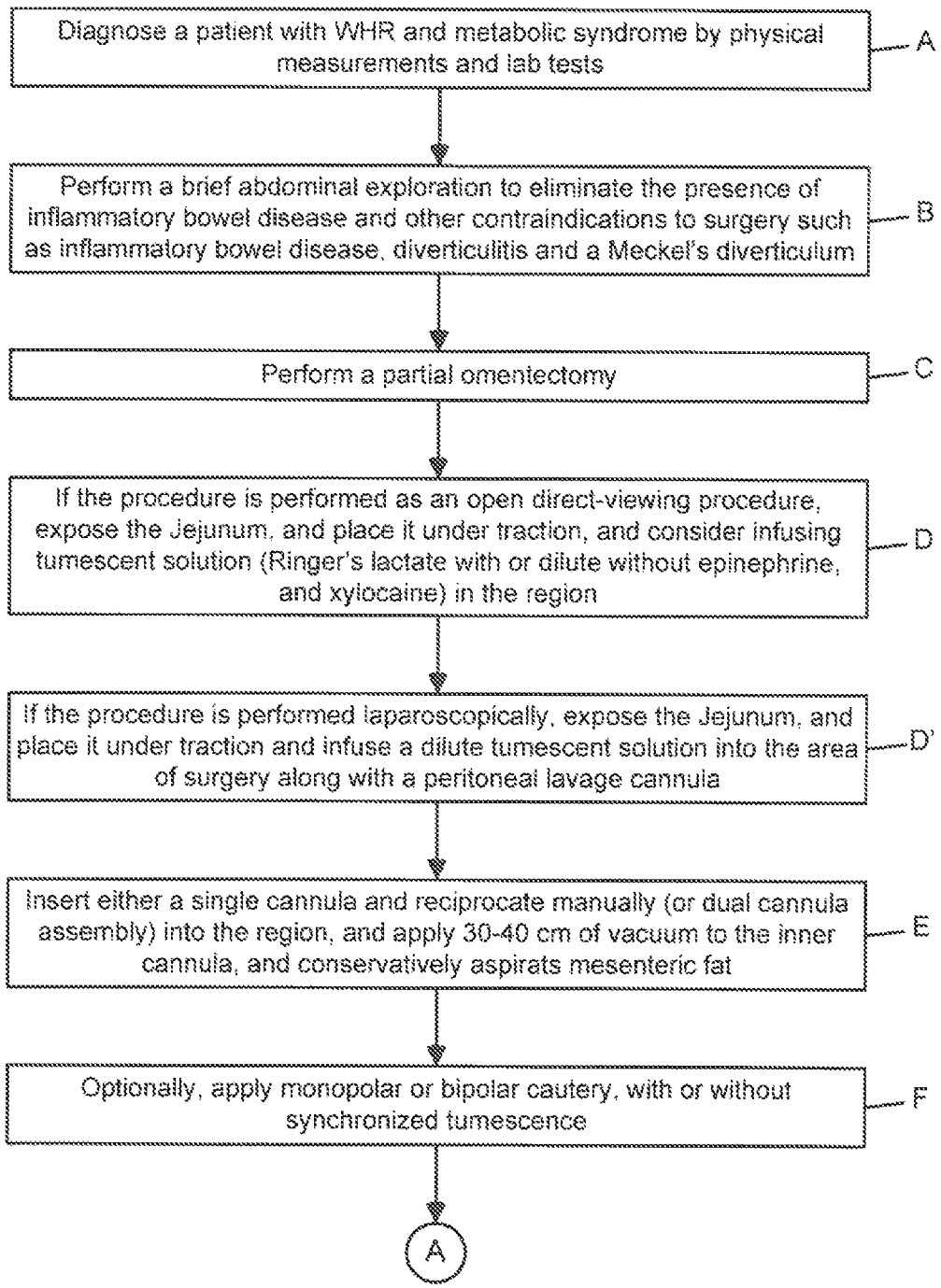
FIGS. 7A and 7B a flow chart illustrating the primary steps carried out during the illustrative embodiment of the method of treating WHR and metabolic syndrome by mesenteric visceral fat aspiration according to the present invention, comprising diagnosis, exploration, partial omentectomy, small bowel mesenteric visceral fat aspiration, large bowel mesenteric visceral fat aspiration, followed by subcutaneous visceral fat aspiration, abdominal and dermatolipectomies as indicated.
Figure 7B:
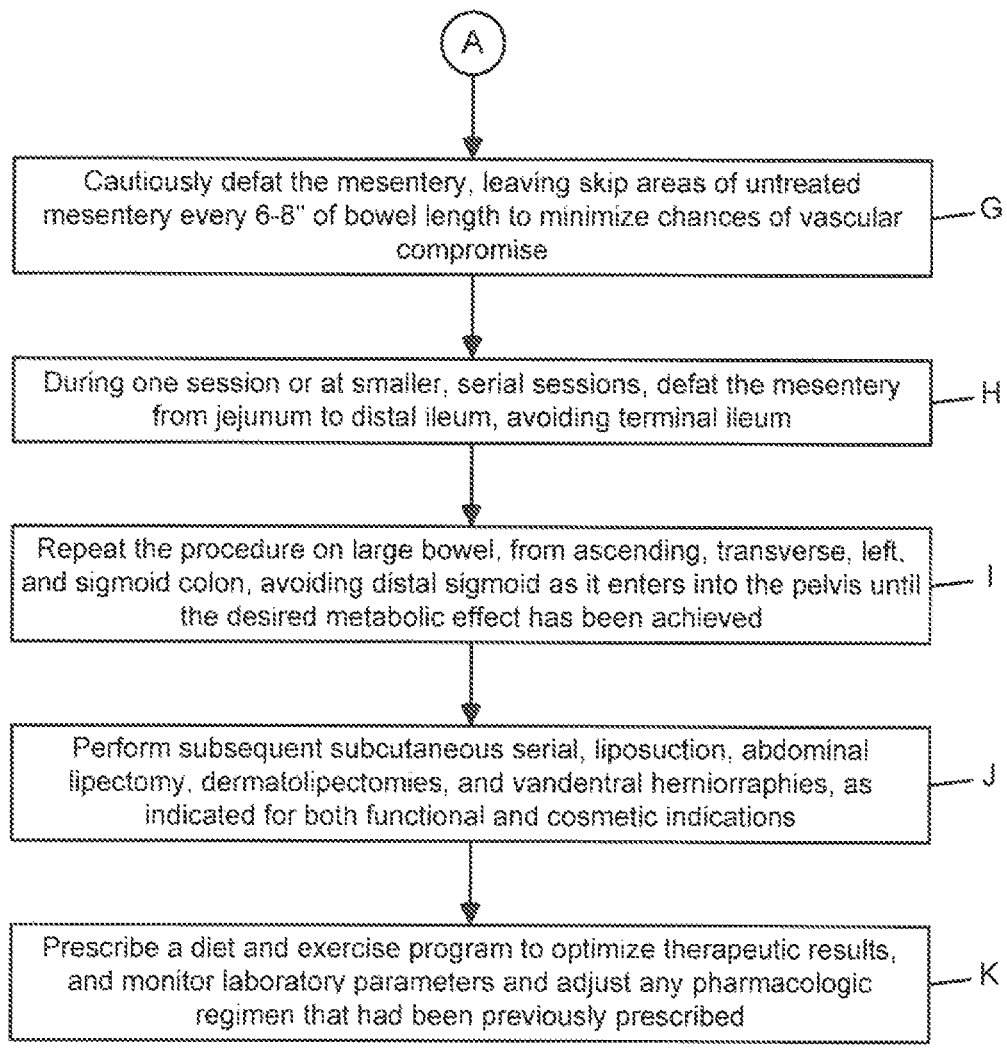

Method of Treating WHR and Metabolic Syndrome According to the Principles of the Present Invention FIGS. 7A and 7B illustrates the primary steps carried out during the illustrative embodiment of the method of treating WHR and metabolic syndrome by mesenteric visceral fat aspiration according to the present invention, comprising diagnosis, exploration, partial omentectomy, small bowel mesenteric visceral fat aspiration, large bowel mesenteric visceral fat aspiration, followed by subcutaneous visceral fat aspiration, abdominal and dermatolipectomies as indicated.

As indicated in Step A in FIG. 7B, the surgeon diagnoses a patient with metabolic syndrome and/or obesity, using the waist-to-hip ratio (WHR), by physical measurements and lab tests. Metabolic Syndrome will be diagnosed upon the presence of any Three Risk Factors: Abdominal obesity; Triglycerides; HDL cholesterol; Blood Pressure; and FBS.
Defining levels for males and females are as follows:
Female >88 cm (>35")
Men: >102 cm.(>40")
≥150 ml/dl
Men <40 mg/dl
Women <50 mg/dl
≥130/≥85 mm Hg ≥110 mg/dl
??????

As indicated in Step B in FIG. 7A, the surgeon performs a brief abdominal exploration or inspection to eliminate the presence of inflammatory bowel disease and other contraindications to surgery, such as, diverticulitis and a Meckel's diverticulum, or any other pathology. At her option, the surgeon may infuse a tumescent solution (Ringer's lactate with or without dilute epinephrine, and with or without xylocaine) as described above to prepare the area for treatment.

As indicated in Step C in FIG. 7A, the surgeon performs a partial omentectomy by removing the redundant omental apron.

As indicated in Step D in FIG. 7A, when performed as an open direct-viewing procedure, the omentum is retracted and the jejunum is exposed. Either by the hands of an assistant in an open procedure or with aid of atraumatic laparoscopic graspers [Endo Babcock or Dolphin Nose Grasper], the proximal jejunum is isolated and placed under gentle tension. One atraumatic grasper is inserted in the right upper quadrant for retraction of the jejunum towards the liver, and a second atraumatic grasper is inserted in the left lower quadrant, placed on a section of jejunum approximately 6 to 8 inches distal to the previously placed grasper, and retracted caudally towards the left lower quadrant. The jejunum is placed under tension and the mesentery exposed and straightened.

As indicated at Step D in FIG. 7A, when performed as a laparoscopic procedure, a pneumoperitoneum is created in the usual fashion and the trochars are inserted so the procedure may be performed under laparoscopic guidance with multiple monitors. A partial omentectomy may be carried out by removing the caudal portions of the omentum. When performed laparoscopically, omentum is removed in strips to facilitate removal through laparoscopic portals. Care is taken to obtain strict hemostasis and to preserve an apron of protective omentum while it is substantially shortened and defatted.

FIG. 9A depicts the bowel grasped between two clamps to tent up the mesentery.

FIG. 9B depicts a cannula inserted into the tented mesentery to infuse tumescent solution.

As indicated in Step E in FIG. 7A, a retractor is inserted through the right lower quadrant and placed posteriorly beneath the tented mesentery. An incision is made anteriorly in the mesentery, approximately ⅔ of the distance between its base and the bowel. The surgeon then inserts either a single cannula through the right lower quadrant and into an anterior incision in the jejunal mesentery, and reciprocates it manually, or preferably inserts the power-assisted twin cannula assembly 5 into the region, and applies 30-40 cm Hg of vacuum to the inner cannula, and conservatively aspirates mesenteric fat. FIG. 9C depicts insertion of the twin cannula device 5 into the previously tumesced and tented mesentery.

When using a laparoscopically-guided electro-cauterizing twin-cannula visceral fat aspiration instrument system shown in FIG. 1, there is much less risk of vascular disruption or visceral injury than when using single cannula instrument, because the twin cannula instrument protects the adventitia of the arboreal blood vessels from injury, and allows treatment of larger areas more rapidly and effectively.

As indicated in Step F in FIG. 7A, the surgeon optionally, applies monopolar or bipolar cautery, with or without synchronized tumescence. By including a separate fluidic channel in the outer cannula, extending from its base to its tip, it is possible to synchronize a pulsed infusion of tumescent solutions or irrigation (e.g. lactated Ringer's solution with or without small amounts of epinephrine (e.g. 1:100,000-1:400,000) through this additional channel in the tip of the twin cannula assembly with the advancement of the inner cannula, to facilitate fat aspiration with a sump effect. Alternatively, a totally separate cannula may be placed with the mesentery and used for pulsatile or non-pulsatile, synchronized or unsynchronized infusion near the tip of the twin cannula assembly 5.

By eliminating the battering ram effect of a reciprocating cannula and the need for tumescent solution for hemostasis, twin cannula visceral fat aspiration allows the minimally invasive removal of soft tissue in any location, including the intestinal mesentery by either open or laparoscopic approaches. Unlike single cannula visceral fat aspiration cannulas, the tube-within-a-tube construction of the twin cannula assembly 5 is particularly suited to a laparoscopic approach as all viscera are spared disruption from the moving member except the limited area of fat being aspirated in the mesentery adjacent to the outer cannula slot. The relatively stationary outer cannula reduces friction caused by the continually reciprocating inner cannula and the laparoscopy portal. Placement of the outer cannula 5A is positional, rather than actively reciprocating, to avulse particles of fat.

Twin cannula mesenteric visceral fat aspiration (TCML) according to the principles of the present invention described above, thus allows direct correction of abdominal obesity, and in a less invasive and dramatically immediate fashion without the untoward nutritional consequences, hepatic, or renal complications of gastric bypass or banding procedures.

The use of twin cannula visceral fat aspiration, with or without bipolar cautery hemostasis and with or without a synchronized pulsed infusion of tumescent or irrigation solution through the cannula, offers a controlled, rapid, and safer way of treating a length of intestine with much less risk of bleeding or vascular injury.

Although bipolar hemostasis obviates the need for tumescence with epinephrine containing solutions, small amounts of epinephrine could be added to small pulses of lactated Ringer's solution, with or without small quantities of local anaesthetic, which are synchronized with the advancement of the inner cannula within the outer cannula.

Since the irrigation solution is immediately aspirated through the aspiration aperture 55 of the twin (twin) cannula assembly 5 of FIG. 2A or 3A, the systemic effects of vasopressor and local anesthetics during twin cannula synchronized tumescence (TCST) would be more limited than an alternative means, such as infusion of a similarly dilute epinephrine and xylocaine in lactated Ringer's solution with a Tenckoff catheter via peritoneal lavage.

Epidural or general anaesthesia could replace or augment synchronized infusion or peritoneal lavage. Although TCST is the preferred embodiment of the described method, the present invetntion contemplates choosing modalities that are optimized for each individual patient's physiologic and cardiovascular status, and concentrations of xylocaine and epinephrine in the employed solutions from zero to therapeutic, as the situation dictates.

As indicated in Step G in FIG. 7B, the surgeon cautiously defats the mesentery, leaving skip areas of untreated mesentery every 6-8" of bowel length to minimize chances of vascular compromise. This step can be achieved by applying a vacuum of 30-40 cm Hg, and defatting the mesentery by initiating mechanical reciprocation of the inner cannula 5B within the outer cannula 5A of the transiently stationary twin cannula assembly 5. Care is taken to retain some fat and avoid creating defects that might allow intestine to herniate through, and any perforations in the mesentery are closed to eliminate this hazard. The area of treatment is inspected for hemostasis and any defects in the mesentery repaired. The jejunum between clamps is inspected for good vascular supply.

As indicated in Step H IN FIG. 7B, during a single session or during smaller, serial sessions, the surgeon defats the mesentery from jejunum to distal ileum, avoiding terminal ileum. Then, as with the open approach, a small area is skipped much like a radiating spokes on a wheel to assure continuity of blood supply, and the next 8" area of jejunum is tented and the procedure repeated until the terminal ileum is reached and left untreated. Any difficulties with hemostasis or questionable vascular viability of the bowel indicate the necessity of a resection and possible conversion to an open procedure.

As indicated in Step I in FIG. 7B, the surgeon repeats the procedure on the large bowel and/or the small bowel for greatest effect. The mesentery of the large bowel would be approached from the ascending colon to the sigmoid colon, avoiding the area surrounding the ileocecal valve, and the distal sigmoid colon as it descends into the pelvis, and the mesentery to any areas of large bowel which appear grossly involved with diverticulitis.

As indicated in Step J in FIG. 7B, the surgeon performs subsequent subcutaneous serial, visceral fat aspiration, abdominal lipectomy, dermatolipectomies, and ventral herniorrhaphies, as indicated for both functional and cosmetic indications. Large volume subcutaneous visceral fat aspiration, panniculectomy, abdominoplasty, repair of any ventral hernias or diastasis recti could be carried out in serial sessions to obtain a much tightened abdominal corset for both functional and cosmetic improvement. The majority of these procedures can be performed under conscious sedation and on an ambulatory basis on these patients with minimal complications because of their improved metabolic profiles.

As indicated in Step K in FIG. 7B, the surgeon prescribes a diet and exercise program to optimize therapeutic results, and monitors laboratory parameters and adjust any pharmacologic regimen that had been previously prescribed.

Figure 8A:
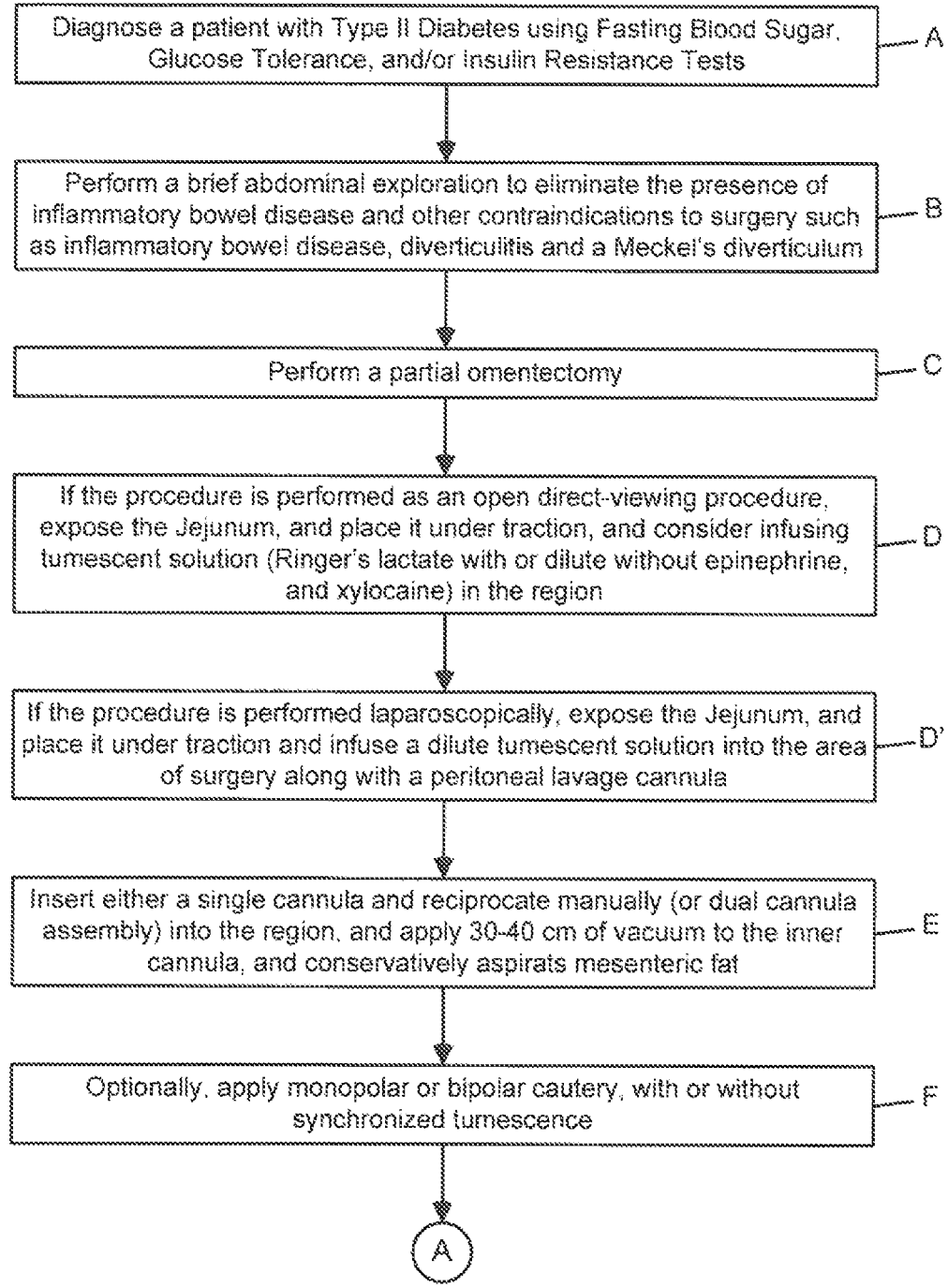
FIGS. 8A and 8B a flow chart illustrating the primary steps carried out during the illustrative embodiment of the method of treating type II diabetes by mesenteric visceral fat aspiration according to the present invention, comprising diagnosis, exploration, partial omentectomy, small bowel mesenteric visceral fat aspiration, large bowel mesenteric visceral fat aspiration, followed by subcutaneous visceral fat aspiration, abdominal and dermatolipectomies as indicated.
Figure 8B:
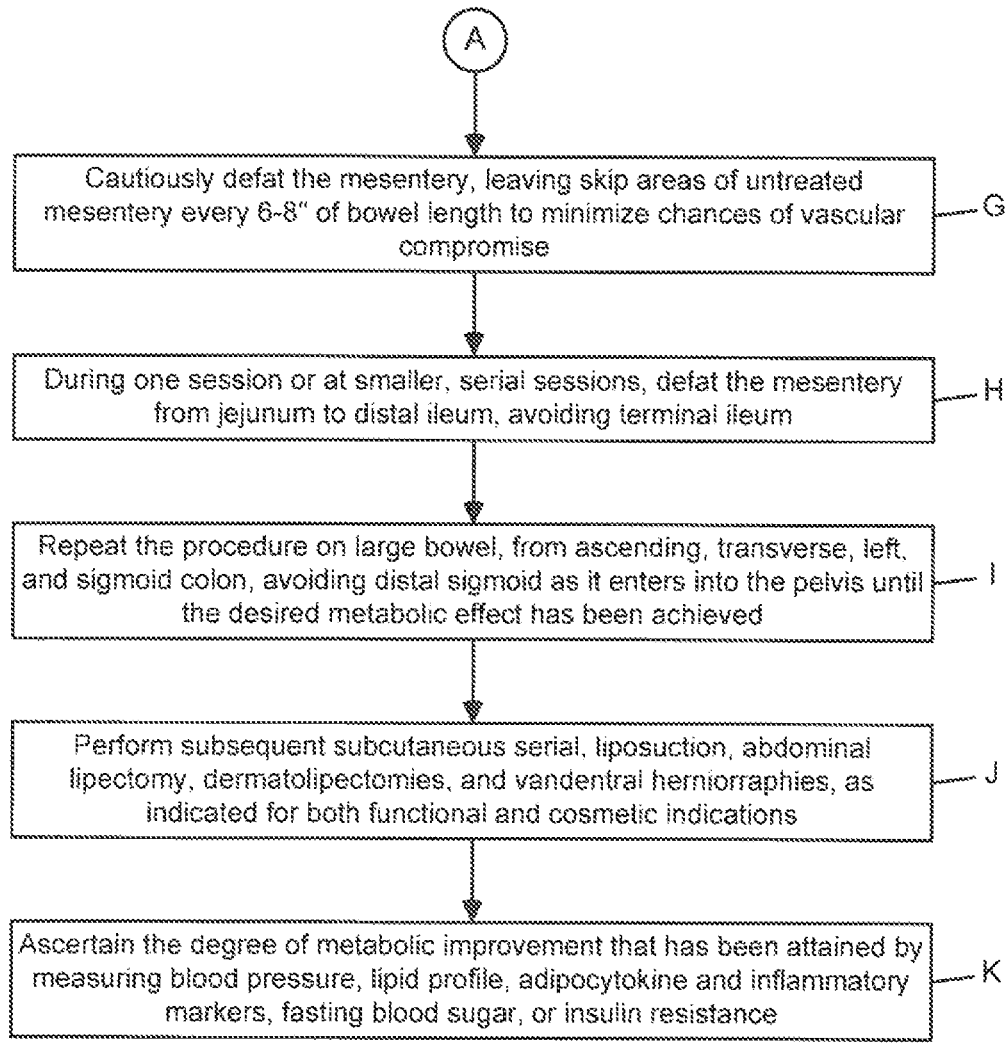

Method of Treating Type II Diabetes According to the Principles of the Present Invention FIGS. 8A and 8B illustrate the primary steps carried out during the method of treating type II diabetes by mesenteric visceral fat aspiration according to the illustrative embodiment of the present invention, comprising the steps of: diagnosis, exploration, partial omentectomy, small bowel mesenteric visceral fat aspiration, large bowel mesenteric visceral fat aspiration, followed by subcutaneous visceral fat aspiration, abdominal and dermatolipectomies as indicated.

As indicated in Step A in FIG. 8A, the surgeon diagnoses a patient with type II diabetes by physical measurements and lab tests. Typically, this diagnosis is made using Fasting Blood Sugar, Glucose Tolerance or Insulin resistance (hyperinsulinemic glucose clamp test, considered to be the gold standard technique for quantification of insulin sensitivity. [Halaas J L, Gajiwala K S, Ma ei M, Cohen S L, et al.: Weight-reducing e ects of the plasma protein encoded by the obese gene. Science 269:543,1995]. This test is based on infusing a known dose of insulin (1 mU/kg/min) and glucose (20% solution) at a constant speed to achieve astable plasma concen-tration of insulin. The plasma glucose level is continually determined using a bedside glucose analyzer, and the exogenous glucose infusion rate is adjusted continually to prevent hypoglycemia. Once the steady state is reached, the amount of infused glucose is the same as that used by the peripheral tissue. Therefore, insulin sensitivity can be calculated as the glucose infusionrate (mg/kg/min) over the last 60 min. A diagnosis of diabetes will be made if you have a fasting blood sugar level of 126 milligrams per deciliter or higher on two separate days.

Diabetes also may be diagnosed based on a random high glucose level of [3] 200 mg/dl and symptoms of the disease. The most common glucose tolerance test is the oral glucose tolerance test (OGTT). The patient cannot eat or drink anything after midnight before the test. For the test, the patient will be asked to drink a liquid containing a certain amount of glucose. The patient's blood will be taken before s/he does this, and again every 30 to 60 minutes after s/he drinks the solution. The test takes up to 3 hours.

Normal blood values for a 75-gram oral glucose tolerance test used to check for type 2 diabetes:
Fasting: 60 to 100 mg/dL
1 hour: less than 200 mg/dL
2 hours: less than 140 mg/dL. Between 140-200 mg/dL is considered impaired glucose tolerance or pre-diabetes.
This group is at increased risk for developing diabetes.
Greater than 200 mg/dL is diagnostic of diabetes mellitus As indicated in Step B in FIG. 8A, the surgeon performs a brief abdominal exploration or inspection to eliminate the presence of inflammatory bowel disease and other contraindications to surgery, such as, diverticulitis and a Meckel's diverticulum, or any other pathology. At her option, the surgeon may infuse a tumescent solution (Ringer's lactate with or without dilute epinephrine, and with or without xylocaine) as described above to prepare the area for treatment.

As indicated in Step C in FIG. 8A, the surgeon performs a partial omentectomy by removing the redundant omental apron.

As indicated in Step D in FIG. 8A, when performed as an open direct-viewing procedure, the omentum is retracted and the jejunum is exposed. Either by the hands of an assistant in an open procedure or with aid of atraumatic laparoscopic graspers [Endo Babcock or Dolphin Nose Grasper], the proximal jejunum is isolated and placed under gentle tension. One atraumatic grasper is inserted in the right upper quadrant for retraction of the jejunum towards the liver, and a second atraumatic grasper is inserted in the left lower quadrant, placed on a section of jejunum approximately 6 to 8 inches distal to the previously placed grasper, and retracted caudally towards the left lower quadrant. The jejunum is placed under tension and the mesentery exposed and straightened.

As indicated at Step D in FIG. 8A, when performed as a laparoscopic procedure, a pneumoperitoneum is created in the usual fashion and the trochars are inserted so the procedure may be performed under laparoscopic guidance with multiple monitors. A partial omentectomy may be carried out by removing the caudal portions of the omentum. When performed laparoscopically, omentum is removed in strips to facilitate removal through laparoscopic portals. Care is taken to obtain strict hemostasis and to preserve an apron of protective omentum while it is substantially shortened and defatted.

FIG. 9A depicts the bowel grasped between two clamps to tent up the mesentery.

FIG. 9B depicts a cannula inserted into the tented mesentery to infuse tumescent solution.

As indicated in Step E in FIG. 8A, a retractor is inserted through the right lower quadrant and placed posteriorly beneath the tented mesentery. An incision is made anteriorly in the mesentery, approximately ⅔ of the distance between its base and the bowel. The surgeon then inserts either a single cannula through the right lower quadrant and into an anterior incision in the jejunal mesentery, and reciprocates it manually, or preferably inserts the power-assisted twin cannula assembly 5 into the region, and applies 30-40 cm Hg of vacuum to the inner cannula, and conservatively aspirates mesenteric fat. FIG. 9C depicts insertion of the twin cannula device 5 into the previously tumesced and tented mesentery.

When using a laparoscopically-guided electro-cauterizing twin-cannula visceral fat aspiration instrument system shown in FIGS. 1A, there is much less risk of vascular disruption or visceral injury than when using single cannula instrument, because the twin cannula instrument protects the adventitia of the arboreal blood vessels from injury, and allows treatment of larger areas more rapidly and effectively.

As indicated in Step F in FIG. 8A, the surgeon optionally, applies monopolar or bipolar cautery, with or without synchronized tumescence. By including a separate fluidic channel in the outer cannula, extending from its base to its tip, it is possible to synchronize a pulsed infusion of tumescent solutions or irrigation (e.g. lactated Ringer's solution with or without small amounts of epinephrine (e.g. 1:100,000-1:400,000) through this additional channel in the tip of the twin cannula assembly with the advancement of the inner cannula, to facilitate fat aspiration with a sump effect. Alternatively, a totally separate cannula may be placed with the mesentery and used for pulsatile or non-pulsatile, synchronized or unsynchronized infusion near the tip of the twin cannula assembly 5.

By eliminating the battering ram effect of a reciprocating cannula and the need for tumescent solution for hemostasis, twin cannula visceral fat aspiration allows the minimally invasive removal of soft tissue in any location, including the intestinal mesentery by either open or laparoscopic approaches. Unlike single cannula visceral fat aspiration cannulas, the tube-within-a-tube construction of the twin cannula assembly 5 is particularly suited to a laparoscopic approach as all viscera are spared disruption from the moving member except the limited area of fat being aspirated in the mesentery adjacent to the outer cannula slot. The relatively stationary outer cannula reduces friction caused by the continually reciprocating inner cannula and the laparoscopy portal. Placement of the outer cannula 5A is positional, rather than actively reciprocating, to avulse particles of fat.

Twin cannula mesenteric visceral fat aspiration according to the principles of the present invention described above, thus allows direct correction of abdominal obesity, and in a less invasive and dramatically immediate fashion without the untoward nutritional consequences, hepatic, or renal complications of gastric bypass or banding procedures.

The use of twin cannula visceral fat aspiration, with or without bipolar cautery hemostasis and with or without a synchronized pulsed infusion of tumescent or irrigation solution through the cannula, offers a controlled, rapid, and safer way of treating a length of intestine with much less risk of bleeding or vascular injury.

Although bipolar hemostasis obviates the need for tumescence with epinephrine containing solutions, small amounts of epinephrine could be added to small pulses of lactated Ringer's solution, with or without small quantities of local anaesthetic, which are synchronized with the advancement of the inner cannula within the outer cannula.

Since the irrigation solution is immediately aspirated through the aspiration aperture 55 of the twin (twin) cannula assembly 5 of FIG. 2A or 3A, the systemic effects of vasopressor and local anesthetics during twin cannula synchronized tumescence (TCST) would be more limited than an alternative means, such as infusion of a similarly dilute epinephrine and xylocaine in lactated Ringer's solution with a Tenckoff catheter via peritoneal lavage.

Epidural or general anaesthesia could replace or augment synchronized infusion or peritoneal lavage. Although TCST is the preferred embodiment of the described method, the present invetntion contemplates choosing modalities that are optimized for each individual patient's physiologic and cardiovascular status, and concentrations of xylocaine and epinephrine in the employed solutions from zero to therapeutic, as the situation dictates.

As indicated in Step G in FIG. 8B, the surgeon cautiously defats the mesentery, leaving skip areas of untreated mesentery every 6-8" of bowel length to minimize chances of vascular compromise. This step can be achieved by applying a vacuum of 30-40 cm Hg, and defatting the mesentery by initiating mechanical reciprocation of the inner cannula 5B within the outer cannula 5A of the transiently stationary twin cannula assembly 5. Care is taken to retain some fat and avoid creating defects that might allow intestine to herniate through, and any perforations in the mesentery are closed to eliminate this hazard. The area of treatment is inspected for hemostasis and any defects in the mesentery repaired. The jejunum between clamps is inspected for good vascular supply.

As indicated in Step H in FIG. 8B, during a single session or during smaller, serial sessions, the surgeon defats the mesentery from jejunum to distal ileum, avoiding terminal ileum. Then, as with the open approach, a small area is skipped much like a radiating spokes on a wheel to assure continuity of blood supply, and the next 8" area of jejunum is tented and the procedure repeated until the terminal ileum is reached and left untreated. Any difficulties with hemostasis or questionable vascular viability of the bowel indicate the necessity of a resection and possible conversion to an open procedure.

As indicated in Step I in FIG. 8B, the surgeon repeats the procedure on the large bowel and/or the small bowel for greatest effect. The mesentery of the large bowel would be approached from the ascending colon to the sigmoid colon, avoiding the area surrounding the ileocecal valve, and the distal sigmoid colon as it descends into the pelvis, and the mesentery to any areas of large bowel which appear grossly involved with diverticulitis.

As indicated in Step J in FIG. 8B, the surgeon performs subsequent subcutaneous serial, visceral fat aspiration, abdominal lipectomy, dermatolipectomies, and ventral herniorraphies, as indicated for both functional and cosmetic indications. Large volume subcutaneous visceral fat aspiration, panniculectomy, abdominoplasty, repair of any ventral hernias or diastasis recti could be carried out in serial sessions to obtain a much tightened abdominal corset for both functional and cosmetic improvement. The majority of these procedures can be performed under conscious sedation and on an ambulatory basis on these patients with minimal complications because of their improved metabolic profiles.

As indicated in Step K in FIG. 8B, the surgeon ascertains the degree of metabolic improvement that has been attained by measuring blood pressure, lipid profile, adipocytokine and inflammatory markers, fasting blood sugar, or insulin resistance via the hyperinsulimic glucose clamp test previously described, repeating testing at 2 mos/6 mos/9 mos/1 yr/1.5 yrs/2 yrs.

Alternative Embodiments Which Readily Come to Mind

While the multi-function twin-cannula assembly described above has been shown used with a twin cannula assembly, it is understood that in alternate embodiments, the inner cannula can be adapted to provide a similar fluid infusion channel that terminates proximal to the luer fitting and allows for fluid infusion. As indicated, in twin cannula embodiments, infusion can be either synchronized. However, in single cannula embodiments, infusion can be unsynchronized as there will be less advantage and practicality in providing synchronization in a more rapidly reciprocating, short stroke single cannula instrument design.

While a barb Christmas-tree type connector is shown on the stationary tubing connector, of each hand-supportable housing, it is understood that the stationary tubing connector may also be realized as a snap-lock type connector for establishing and maintaining a connection with the end portion of flexible aspiration tubing.

Further, the powered fat aspiration instrument of the present invention can be designed so that its cylindrical guide tube is made very simple, inexpensively and is disposable so as to eliminate the need for a magnet which can loose its strength with autoclaving. The cannula base portion can be made so as to use washers that are wafer thin, for only one day of surgery. Such washers can function as diaphragms, staying in place and deforming to allow to-fro motion of the cylindrical guide tube within the cylindrical guide tube. Also, these washers can have an umbrella-shape, or be have a thin cylindrical geometry.

Also, while not shown, any embodiment of the power-assisted visceral fat aspiration instrument of the present invention can be provided with various means along the cannula assembly to effect hemostasis during liposuction procedures and the like using, for example, RF-based electro cauterization, as taught in Applicant's prior U.S. Pat. Nos. 6,872,199 and 7,381,206, incorporated herein by reference.

Several modifications to the illustrative embodiments have been described above. It is understood, however, that various other modifications to the illustrative embodiment of the present invention will readily occur to persons with ordinary skill in the art. All such modifications and variations are deemed to be within the scope and spirit of the present invention as defined by the accompanying Claims to Invention.

What is claimed is:

1. A method of collecting and in situ processing of aspirated fat tissue sampled from a human patient, said method comprising the steps:
   (a) providing a surgeon with a powered-assisted hand-held fat tissue aspiration instrument having a cannula, and a fat tissue sampling, processing and collection device installed between said power-assisted hand-held fat aspiration instrument and a vacuum source, wherein said fat tissue sampling, collection and processing device includes a suction plate, mounted within a collection chamber, and for supporting the open proximal ends of a plurality of tissue collection and processing tubes, wherein each said tissue collection and processing tube has micro-pores formed in the side walls thereof, and its distal end opening is capped;
   (b) selecting a first tissue collection and processing syringe in said tissue sampling, processing and collection device to be filled with a first sample of fat tissue aspirated by said cannula from a first specified location in the body of said patient;
   (c) using said powered hand-held fat tissue aspiration instrument to aspirate fat tissue from said human patient, collect said first sample of aspirated fat tissue in said first tissue collection and processing syringe selected in step (b), and allow fluid to flow and filter through said micro-pores as aspirated fat tissue flows through the cannula of said power-assisted hand-held fat aspiration instrument, and one or more selected tissue collection and processing tubes mounted on said suction plate, during tissue aspiration operations;
   (d) selecting a second tissue collection and processing syringe in said tissue sampling, processing and collection device to be filled with a second sample of fat tissue aspirated by said cannula from a second specified location in the body of said patient;
   (e) using said hand-held powered fat tissue aspiration instrument to aspirate fat tissue from said human patient and collecting said second sample of aspirated fat tissue in said second tissue collection and processing tube selected in step (d), and allow fluid to flow and filter through said micro-pores as aspirated fat tissue flows through the cannula of said power-assisted hand-held fat aspiration instrument, and one or more selected tissue collection and processing tubes mounted on said suction plate, during tissue aspiration operations; and
   (f) removing said first and second fat tissue collection and processing tubes from said fat tissue sampling, processing and collection device, after completion of fat tissue aspiration operations.

2. The method of claim 1, which further comprises:
   (g) testing the fat samples contained in said first and second fat tissue collection and processing tubes, for levels of particular types of biochemical secretions capable of indicating the patient's risk of a particular disease.

3. The method of claim 2, wherein the levels of said biochemical secretions are selected from the group consisting of resistin level, adiponectin level, TNF-a marker level, interleukin-6 (IL-6) inflammatory marker level, and IL-10 inflammatory marker level.

4. The method of claim 1, wherein said collection chamber has a closed end with a central aperture, and an open end with a hollow inner chamber disposed between said closed end and said open end; and wherein said tissue sampling, processing and collection device further comprises: a removable lid for connection to the open end of said collection chamber, and having a central flow channel terminated in a first connector connecting said tissue sampling, processing and collection device to a vacuum source by way of vacuum tubing; and a selector for engagement with said suction plate and having a hollow central post section that passes through said central aperture and establishes fluid communication with a flow path that extends from center to periphery to control the flow of aspirated fat from said hand-held power-assisted tissue aspiration instrument through said selector and into a selected one of said tissue collection and processing tubes mounted on said suction plate.

5. The method of claim 4, wherein said tissue sampling, processing and collection device includes a knob engaging with said hollow central post and enabling the rotation of said selector, relative to said suction plate, to select (i) said first tissue collection and processing tube during step (b), into which the first sample of aspirated fat is directed to flow for collection and indexing purposes during tissue sampling, and (ii) said second tissue collection and processing tube during step (d), into which the second sample of aspirated fat is directed to flow for collection and indexing purposes during tissue sampling.

6. The method of claim 1, wherein said collection chamber is labeled for orientation, indicating the side facing towards said patient and the side facing towards said vacuum source.

7. The method of claim 1, wherein said suction plate comprises multiple hollow projections for supporting the open proximal ends of a plurality of tissue collection and processing tubes, and wherein said suction plate has numbers identifying each said tissue collection and processing tube mounted on the hollow projections of said suction plate.

8. The method of claim 4, wherein when said knob is pushed down against a biasing force, said knob can be rotated to select which one or more of said plurality of tissue collection and processing tubes, into which a sampled of aspirated fat tissue to is be collected and processed in situ during tissue aspiration operations.

9. The method of claim 4, wherein said flow path extends to the selected tissue collection and processing tube to complete the fluid communication channel, set up by said selector.

10. The method of claim 1, wherein said collection chamber is made from an optically-transparent material.

11. The method of claim 4, wherein said removable lid is threaded for connection to the open end of said collection chamber.

\* \* \* \* \*